(12) United States Patent
Angehrn et al.

(10) Patent No.: US 6,740,642 B2
(45) Date of Patent: May 25, 2004

(54) MACROLIDES WITH ANTIBACTERIAL ACTIVITY

(75) Inventors: Peter Angehrn, Boeckten (CH); Daniel Hunziker, Moehlin (CH); Pierre-Charles Wyss, Therwil (CH)

(73) Assignee: BAsilea Parmaceutica AG (CH)

( * ) Notice: Subject to any disclaimer, the term of this patent is extended or adjusted under 35 U.S.C. 154(b) by 11 days.

(21) Appl. No.: 10/362,526

(22) PCT Filed: Aug. 20, 2001

(86) PCT No.: PCT/EP01/09560
§ 371 (c)(1), (2), (4) Date: Feb. 21, 2003

(87) PCT Pub. No.: WO02/16380
PCT Pub. Date: Feb. 28, 2002

(65) Prior Publication Data
US 2003/0199459 A1 Oct. 23, 2003

(30) Foreign Application Priority Data
Aug. 22, 2000 (EP) .............................. 00117971

(51) Int. Cl.⁷ .................... A61K 31/70; C07H 17/08
(52) U.S. Cl. .................... 514/29; 536/7.2; 536/7.3; 536/7.4
(58) Field of Search .............. 536/7.2, 7.4, 7.3; 514/29

(56) References Cited

FOREIGN PATENT DOCUMENTS

EP          680 967          11/1995

OTHER PUBLICATIONS

Or et al., J. Med. Chem., 43, pp. 1045–1049 (2000).

Primary Examiner—Elli Peselev

(74) Attorney, Agent, or Firm—Gibbons, Del Deo, Dolan, Griffinger & Vecchione

(57) ABSTRACT

The invention provides new macrolides antibiotics of formula I with improved biological properties and improved stability of the formula

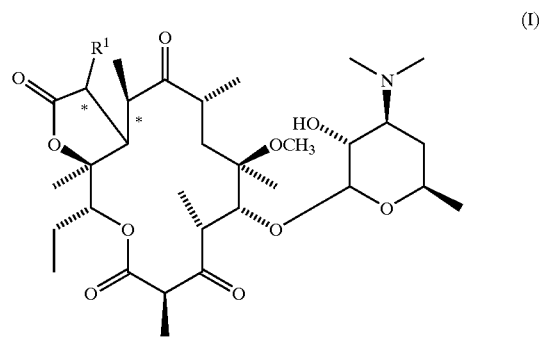

(I)

wherein
R¹ is hydrogen, cyano, —S(L)$_m$R², —S(O)(L)$_m$R², or —S(O)$_2$(L)$_m$R²;
L represents —(CH$_2$)$_n$— or —(CH$_2$)$_n$Z(CH$_2$)$_{n'}$—;
m is 0 or 1;
n is 1, 2, 3, or 4;
n' is 0, 1, 2, 3, or 4;
Z is O, S or NH;
R² is hydrogen, alkyl, heterocyclyl or aryl; which heterocyclyl and the aryl groups may be further substituted;
* indicates a chiral center which is in the (R) or (S) form, as well as a pharmaceutically acceptable acid addition salts or in vivo cleavable esters thereof.

14 Claims, No Drawings

MACROLIDES WITH ANTIBACTERIAL ACTIVITY

This application is a 371 of PCT/EP01/0950 filed Aug. 20, 2001.

This invention relates to new macrolide antibiotics with improved activity and stability, to the use of such antibiotics for the treatment of infectious diseases and to compositions containing such macrolides.

The interest in macrolide antibiotics is increasing because these compounds are a very effective and safe class of agents against gram positive pathogens. Extensive spread of erythromycin A resistance among gram positive cocci isolates raised the urgent need for novel derivatives with improved activity, stability and antimicrobial spectra. The two most successful second generation agents derived from erythromycin A (1) through semisynthesis were its 6-O-methyl derivative clarithromycin (2) and the 15-membered azalide azithromycin (3) arising from a Beckman rearrangement as shown below. However, while featuring improved pharmacokinetics, none of these agents possessed a significant activity against bacterial isolates showing macrolide-lincosamide-streptogramine B (MLS B) cross resistance.

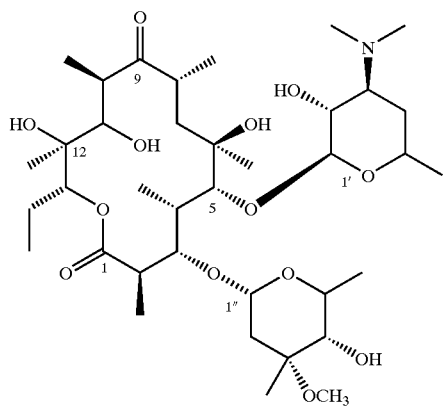

1

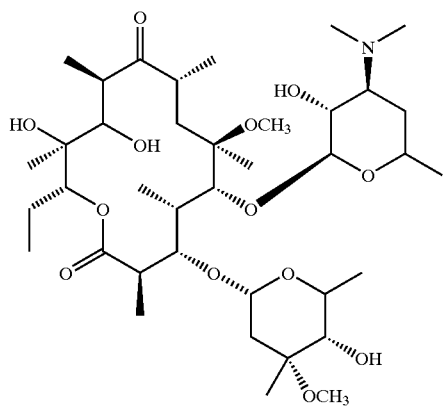

2

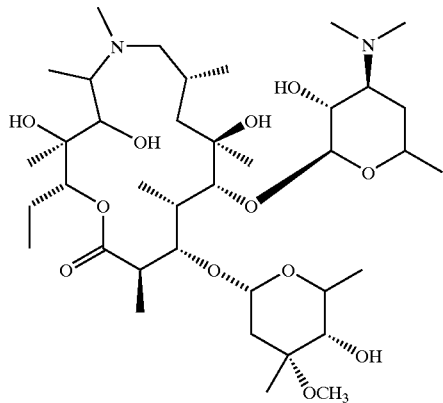

3

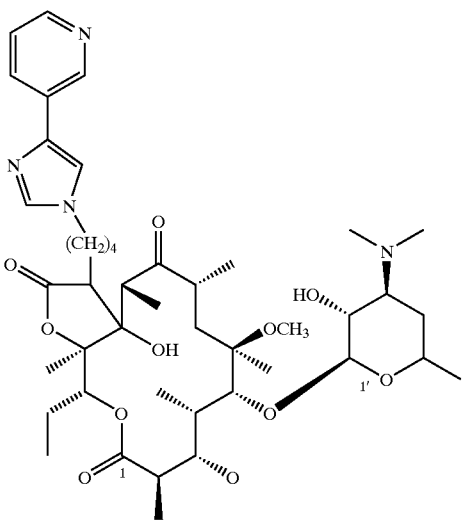

4

Many different semisynthetic third generation derivatives of the ketolide class of macrolide antibiotics have been described, the most potent being HMR 3647 or telithromycin (4) (EP 680967 A1 (1995); FR 2732684 A1 (1996); Bioorg. Med. Chem. Lett. (1999), 9(21), 3075–3080.) and ABT 773 (WO 9809978 (1998); J. Med. Chem. 2000, 43, 1045). However, none of these agents described thus far have been able to overcome constitutive MLS B resistance in *Staphylococcus aureus*.

The invention provides new macrolide antibiotics of formula I with improved biological properties and improved stability.

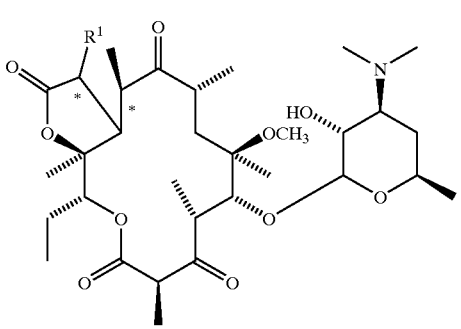

I wherein
R¹ is hydrogen, cyano, —S(L)ₘR², —S(O)(L)ₘR², or —S(O)₂(L)ₘR²;
L represents —(CH₂)ₙ— or —(CH₂)ₙZ(CH₂)ₙ'—;
m is 0 or 1;
n is 1, 2, 3, or 4;
n' is 0, 1, 2, 3, or 4;
Z is O, S or NH;
R² is hydrogen, alkyl, heterocyclyl or aryl; which heterocyclyl and the aryl groups may be further substituted;
* indicates a chiral center which is in the (R) or (S) form.
and pharmaceutically acceptable acid addition salts or in vivo cleavable esters thereof.

These compounds are new and possess potent antimicrobial properties against gram positive and selected gram negative organisms. Therefore, they are useful as agents against gram positive pathogens such as staphylococci, streptococci and pneumococci as well as some gram negative strains such as *H. influenzae* and may be used in human or veterinary medicine for treatment or prevention of infections caused by susceptible organisms.

The chiral center in position 3 is preferably in the (S) whereas the center in 4 are is preferably in the (R) configuration.

As used herein the term "alkyl" refers to straight or branched chain saturated hydrocarbon group having 1 to 12 carbon atoms, preferably 1 to 6 carbon atoms. Such groups are for example methyl, ethyl, n-propyl, isopropyl, tertiary butyl, pentyl, hexyl, and the like.

The term "halogen" refers to chlorine, bromine or iodine.

The term "aryl" refers to 6-membered, aromatic groups with one or more nuclei from 6 to 14 carbon atoms. Examples are phenyl, naphthyl, anthryl and phenanthryl. These groups may be further substituted with, for example, phenyl, alkyl, lower alkoxy such as methoxy, ethoxy, propyloxy or n-butoxy, halogen, hydroxy, amino, alkylamino, dialkylamino or nitro.

As used herein the term "heterocyclyl" refers to an unsaturated or saturated, unsubstituted or substituted 5-, 6-, or 7-membered (mono- or bicyclic) heterocyclic ring system containing at least one hetero atom selected from the group consisting of oxygen, nitrogen, and/or sulfur. Exemplary heterocyclic substituents include, but are not limited to, for example, the following groups:
piperidinyl, morpholinyl, 2-, 3- or 4-pyridyl, pyrrolidinyl, piperazinyl, 1H-pyrazol-1-yl, 1H-[1,2,4]triazol-1-yl, 1H-imidazol-1-yl, pyrazinyl, pyrimidyl, pyridazinyl, pyrazolyl, triazinyl, thiazolyl, thiadiazolyl, oxadiazolyl, triazolyl, 1H-tetrazolyl, 2H-etrazolyl; thienyl, furyl, 1H-azepinyl, tetrahydrothiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, 1,6,3,4-dioxadithiopanyl, oxazolidinyl, tetrahydrothienyl, and the like, or condensed heterocyclic ring systems such as quinolinyl, isoquinolinyl, quinazolinyl, 1H-benztriazolyl, 1H-imidazo[4,5-c]pyridinyl, 5H-imidazo[4,5-c]pyridinyl, 1H-imidazo[4,5-b]pyridin-1-yl, 3H-imidazo[4,5-b]pyridin-3-yl, 1,2,3,4-tetrahydroisoquinolinyl, thieno[2,3-b]pyridinyl, benzothiazolyl, 1H-benzoimidazolyl, 1H-indolyl, 1,2,3,4-tetrahydroquinolinyl, purinyl, e.g. 9H-purin-9-yl, 6-amino-9H-purin-9-yl, and others.

The aryl or heterocyclyl groups may be further substituted by one or more substituents. Such substituents include, for example, alkyl groups as defined above, alkoxy groups such as methoxy, ethoxy, propyloxy or butyloxy, halogen such as fluorine, chlorine, bromine or iodine, halogen substituted alkyl groups such as trifluoromethyl, trichloroethyl, nitro, amino, alkylamino, dialkylamino, alkylthio, mercapto, hydroxy, carbamoyl, a carboxyl group, an oxo group; or unsubstituted or substituted aryl as defined above; or heterocyclyl.

Especially preferred substituents for the heterocyclic groups are alkyl, alkoxy, oxo, amino, alkylamino or dialkylamino. Examples of preferred substituted heterocyclic rings are 1H-pyrimidin-2,4-dione-1-yl, 1H-pyrimidin-2,4-dione-5-methyl-1-yl, 1H-pyrimidin-4-amino-2-one-1yl, 6-amino-9H-purine-9-yl, 6-dimethylamino-9H-purine-9-yl, 3-(pyridin-3-yl)-1H-pyrazol-1-yl, 3-(pyridin-4-yl)-1H-pyrazol-1-yl, 3-(pyridin-3-yl)-1H-imidazol-1-yl, 3-(pyridin-4-yl)-1H-imidazol-1-yl, 3-(pyridin-3-yl)-1H-[1,2,4]triazol-1-yl, or 3-(pyridin-4-yl)-1H-[1,2,4]triazol-1-yl.

Preferred compounds of formula I are compounds, wherein L is —(CH₂)ₙ and n is 0, 1, 2 or 3. Further preferred are compounds of formula I, wherein R² is aryl or heterocyclyl, especially, wherein R² is phenyl, dialkoxyphenyl, 6-amino-9H-purin-9-yl or pyridinyl-1H-pyrazol-1-yl.

Especially preferred compounds of formula I are in Table 1 below:

| Compound no. | R¹ | Example no. |
|---|---|---|
| I-1 |  | 1 |
| I-2 |  | 2 |
| I-3 |  | 3 |
| I-4 |  | 4 |
| I-5 | CH₃S— | 5 |
| I-6 |  | 6 |
| I-7 |  | 7 |

| Compound no. | R¹ | Example no. |
|---|---|---|
| I-8 | 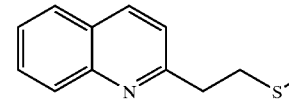 | 8 |
| I-9 | 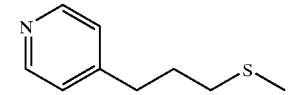 | 9 |
| I-10 | 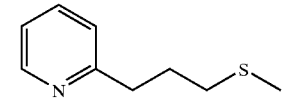 | 10 |
| I-11 | 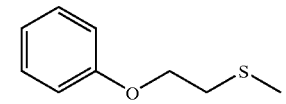 | 11 |
| I-12 | 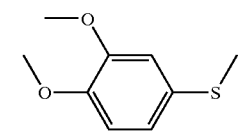 | 12 |
| I-13 | 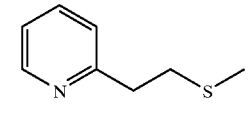 | 13 |
| I-14 | 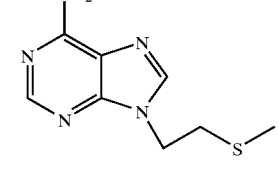 | 14 |
| I-15 | 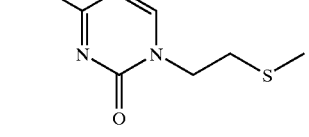 | 15 |
| I-16 | 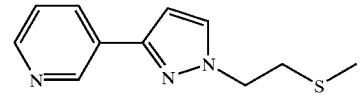 | 16 |
| I-17 | 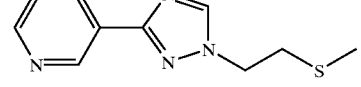 | 17 |
| I-18 | 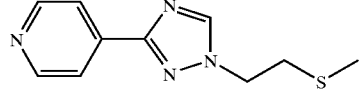 | 18 |
| I-19 | 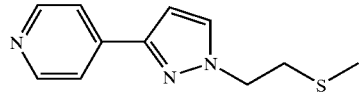 | 19 |
| I-20 |  | 20 |
| I-21 |  | 21 |
| I-22 |  | 22 |
| I-23 | CN | 23 |
| I-24 |  | 24 |
| I-25 | H | 25 |
| I-26 |  | 26 |
| I-27 |  | 27 |
| I-28 |  | 28 |
| I-29 |  | 29 |

-continued

| Compound no. | R¹ | Example no. |
|---|---|---|
| I-30 | 4-methoxyphenyl-pyrazole-N-(CH₂)₃-SMe | 30 |
| I-31 | 4-acetylphenyl-pyrazole-N-(CH₂)₃-SMe | 31 |
| I-32 | adenin-9-yl-(CH₂)₄-SMe | 32 |
| I-33 | 4-amino-pyrazolo[3,4-d]pyrimidin-1-yl-(CH₂)₂-SMe | 33 |
| I-34 | 2,6-diamino-purin-9-yl-(CH₂)₂-SMe | 34 |

-continued

| Compound no. | R¹ | Example no. |
|---|---|---|
| I-35 | 3-(pyridin-3-yl)-pyrazol-1-yl-(CH₂)₃-SMe | 35 |
| I-36 | pyrazolo[3,4-b]pyridin-1-yl-(CH₂)₂-SMe | 36 |
| I-37 | imidazo[4,5-b]pyridin-3-yl-(CH₂)₃-SMe | 37 |
| I-38 | purin-9-yl-(CH₂)₂-SMe | 38 |
| I-39 | purin-7-yl-(CH₂)₃-SMe | 39 |

If desired, compounds of formula I can be converted into a pharmaceutically acceptable acid addition salt. The salt formation is effected at room temperature with methods which are known per se and which are familiar to any person skilled in the art. Not only salts with inorganic acids, but also salts with organic acids come into consideration. Hydrochlorides, hydrobromides, sulfates, nitrates, citrates, acetates, trifluoroacetates, maleates, succinates, methanesulphonates, p-toluenesulphonates and the like are examples of such salts.

Further the compounds can be converted into in vivo cleavable esters, for example into esters with the 2'-hydroxy group of the sugar moiety, such esters are e.g. acetates, pivaloyl esters, tartrates, maleates, succinates, and the like. These esters can be prepared according to methods known in the art, for example by reaction with an appropriate anhydride.

The compounds of the present invention and their pharmaceutically acceptable acid addition salts or in vivo cleavable esters thereof are useful as antibacterial therapeutics, pharyngitis, pneumonia, bronchopneumonia, bronchitis, otitis, sinusitis, and scarlet-fever.

Furthermore, the compounds of formula I can be used as medicaments for the treatment of infections caused by germs such as *Haemophilus influenzae*, *Moraxella catarrhalis*, rickettsiae, ehrlichiae, *Mycoplasma pneumoniae*, Neisseria spp., Chlamydia spp, Legionella spp, *Ureaplasma urealyticum* or by susceptible strains of Mycobacterium spp.

The antibacterial activities of the compounds have been determined by standard microdilution technique (National Committee for Clinical Laboratory Standards. 1997. Methods for dilution antimicrobial susceptibility tests for bacteria that grow aerobically, $4^{th}$ edition. Approved standard M7-A4. National Committee for Clinical Laboratory Standards, Wayne, Pa.). The activities expressed as the minimum inhibitory concentrations (MICs) ($\mu$g/ml) are given in Table 2 below.

| Strain Example | S. aureus ATCC29213 | S. aureus 1086 | S. aureus 745 | E. coli ATCC25922 | P. aeruginosa ATCC27853 (+Ery. 32 µg/ml) | St. pneumoniae 1/1 | St. pneumoniae 1/4 | St. pneumoniae SL199T | St. pneumoniae 12288 |
|---|---|---|---|---|---|---|---|---|---|
| I-3 | 0.5 | 0.5 | >16 | >16 | >16 | <=0.5 | 2 | 16 | 16 |
| I-4 | 1 | 1 | >16 | >16 | >16 | <=0.5 | 8 | 16 | 16 |
| I-5 | 0.5 | 0.5 | >16 | >16 | >16 | <=0.5 | 32 | 16 | >32 |
| I-2 | 1 | 1 | 16 | >16 | >16 | <=0.5 | 1 | 8 | 16 |
| I-1 | <=0.25 | <=0.25 | >16 | >16 | >16 | <=0.5 | 1 | 4 | 32 |
| I-23 | <=0.25 | <=0.25 | >16 | >16 | >16 | <=0.5 | 8 | 32 | >32 |
| I-13 | <=0.25 | <=0.25 | >16 | 16 | >16 | <=0.5 | 1 | 2 | 8 |
| I-11 | <=0.25 | <=0.25 | >16 | >16 | >16 | <=0.5 | 4 | 4 | 8 |
| I-12 | 0.5 | 0.5 | >16 | >16 | >16 | <=0.5 | 1 | 8 | 16 |
| I-24 | 1 | 1 | >16 | >16 | >16 | <=0.5 | 1 | 16 | 16 |
| I-25 | 0.5 | 0.5 | >16 | >16 | >16 | <=0.12 | 16 | >16 | >16 |
| I-14 | <=0.12 | <=0.12 | >16 | 8 | >16 | <=0.12 | 0.25 | 0.25 | 0.25 |
| I-9 | 0.25 | 0.25 | >16 | >16 | >16 | <=0.12 | 0.25 | 0.5 | 2 |
| I-15 | 4 | 4 | >16 | >16 | >16 | <=0.12 | 0.25 | 2 | >16 |
| I-22 | 0.25 | 0.25 | >16 | >16 | >16 | <=0.12 | 1 | 8 | >16 |
| I-7 | <=0.12 | <=0.12 | >16 | >16 | >16 | <=0.12 | <=0.12 | 1 | 8 |
| I-6 | <=0.12 | <=0.12 | >16 | >16 | >16 | <=0.12 | <=0.12 | 1 | 4 |
| I-21 | 0.25 | 0.25 | >16 | >16 | >16 | <=0.12 | >16 | 8 | >16 |
| I-9 | <=0.12 | <=0.12 | >16 | >16 | >16 | <=0.12 | <=0.12 | 2 | 8 |
| I-10 | <=0.12 | <=0.12 | >16 | >16 | >16 | <=0.12 | 0.25 | 2 | 8 |
| I-20 | 0.25 | 0.25 | >16 | >16 | >16 | <=0.12 | <=0.12 | 2 | 2 |
| I-15 | 0.25 | <=0.12 | >16 | >16 | >16 | <=0.12 | 1 | 4 | >16 |
| I-16 | <=0.12 | <=0.12 | >16 | >16 | >16 | <=0.12 | <=0.12 | 0.5 | 0.5 |
| I-17 | <=0.12 | <=0.12 | >16 | >16 | >16 | <=0.12 | <=0.12 | 1 | |
| I-19 | <=0.12 | <=0.12 | >16 | >16 | >16 | <=0.12 | <=0.12 | 1 | 4 |
| I-27 | 0.25 | 1 | >16 | >16 | >16 | <=0.25 | <=0.25 | 1 | 2 |
| I-26 | <=0.12 | <=0.12 | >16 | 16 | >16 | <=0.25 | <=0.25 | <=0.25 | 0.25 |
| References | | | | | | | | | |
| Erythromycin (1) | 0.5 | >32 | >64 | >16 | >16 | <=0.12 | 32 | >32 | >32 |
| Clarithromycin (2) | 0.25 | 16 | >16 | >16 | >16 | <=0.12 | 16 | 16 | >16 |
| Telithromycin (4) | <=0.12 | <=0.12 | >64 | 16 | >16 | <=0.12 | <=0.12 | <=0.12 | 0.25 |
| Josamycin | 2 | 2 | >16 | >16 | >16 | <=0.12 | <=4 | >16 | >16 |

Compounds of formula I possess excellent antibacterial activity against selected pathogenic bacteria such as strains of *Staphylococcus aureus* and *Streptococcus pneumoniae*. They can thus be used as medicaments for the treatment of infectious diseases especially of infectious diseases caused by staphylococci, such as septicemia, skin infections, soft tissue infections, deep infections after trauma, surgery or insertion of foreign material, pneumonia, arthritis, bursitis, and osteomyelitis, infections caused by streptococci such as septicemia, skin infections, soft tissue infections, deep infections after trauma, surgery or insertion of foreign material, The biological activities of compounds of the present invention against *Haemophilus influenzae* have been determined by standard agar dilution method using HTM medium (National Committee for Clinical Laboratory Standards. 1997. Methods for dilution antimicrobial susceptibility tests for bacteria that grow aerobically, $4^{th}$ edition. Approved standard M7-A4. National Committee for Clinical Laboratory Standards, Wayne, Pa.). Their MICs along with MIC's of selected reference compounds are given in Table 3.

| Strain | Erythromycin (1) | Azithromycin (3) | Clarithromycin (2) | Telithromycin (4) | I-14 | I-7 | I-6 |
|---|---|---|---|---|---|---|---|
| *H. influenzae* 1 | 4 | 2 | 8 | 4 | 1 | 4 | 4 |
| 3201 | 4 | 2 | 16 | 4 | 4 | 4 | 4 |
| 3457 | 0.5 | 0.5 | 1 | 0.25 | 0.25 | 0.5 | 0.25 |
| 3640 | 2 | 1 | 4 | 2 | 2 | 2 | 2 |
| 12214 | 4 | 2 | 8 | 4 | 2 | 4 | 4 |
| 23145 | 4 | 2 | 8 | 4 | 4 | 4 | 4 |
| 23369 | 4 | 4 | 16 | 4 | 4 | 8 | 4 |
| H20 HDL | 2 | 1 | 4 | 2 | 1 | 2 | 1 |
| H28 HEL | 2 | 1 | 4 | 2 | 2 | 2 | 2 |
| 4139 | 1 | 0.5 | 4 | 2 | 2 | 2 | 2 |
| H36 ODL | 4 | 2 | 16 | 4 | 2 | 8 | 4 |
| 11 | 4 | 2 | 16 | 4 | 4 | 4 | 4 |
| QK 12/87 | 2 | 0.5 | 2 | 1 | 0.5 | 2 | 1 |
| 2947 | 4 | 2 | 16 | 4 | 2 | 4 | 4 |
| ATCC 9334 | 4 | 2 | 8 | 2 | 4 | 4 | 2 |
| QK 50 | 4 | 2 | 8 | 2 | 2 | 4 | 2 |
| B 1501 | 4 | 1 | 8 | 2 | 1 | 4 | 2 |
| H13 LAH | 4 | 2 | 8 | 2 | 2 | 4 | 2 |
| ATCC 49247 | 4 | 2 | 8 | 4 | 1 | 4 | 2 |
| Rd KW20 | 4 | 2 | 8 | 4 | 4 | 4 | 2 |
| Christy | 4 | 2 | 8 | 4 | 2 | 4 | 2 |

The compounds in accordance with the invention can be used as medicaments. They possess good oral absorption properties. A further embodiment of the present invention are thus medicaments comprising compounds of formula I, their pharmaceutically acceptable acid addition salts or in vivo cleavable esters thereof for the treatment and prevention of infectious diseases, for example, in the form of pharmaceutical preparations for enteral (oral) administration. The products in accordance with the invention can be administered, for example, perorally, such as in the form of tablets, coated tablets, dragees, hard and soft gelatin capsules, solutions, emulsions or suspensions, or rectally, such as in the form of suppositories, or parenterally e.g. by injection, or locally for example by topical administration, preferably the compounds are administered orally.

Pharmaceutical compositions containing these compounds can be prepared using conventional procedures familiar to those skilled in the art, such as by combining the ingredients into a dosage form together with suitable, non-toxic, inert, therapeutically compatible solid or liquid carrier materials and, if desired, the usual pharmaceutical adjuvants.

It is contemplated that the compounds are ultimately embodied into compositions of suitable oral, parenteral or topical dosage forms. The compositions of this invention can contain, as optional ingredients, any of the various adjuvants which are used ordinarily in the production of pharmaceutical preparations. Thus, for example, in formulating the present compositions into the desired oral dosage forms, one may use, as optional ingredients, fillers, such as coprecipitated aluminum hydroxide-calcium carbonate, dicalcium phosphate or lactose; disintegrating agents, such as maize starch; and lubricating agents, such as talc, calcium stearate, and the like. It should be fully understood, however, that the optional ingredients herein named are given by way of example only and that the invention is not restricted to the use hereof. Other such adjuvants, which are well known in the art, can be employed in carrying out this invention.

Suitable as such carrier materials are not only inorganic, but also organic carrier materials. Thus, for tablets, coated tablets, dragees and hard gelatin capsules there can be used, for example, lactose, maize starch or derivatives thereof, talc, stearic acid or its salts. Suitable carriers for soft gelatin capsules are, for example, vegetable oils, waxes, fats and semi-solid and liquid polyols (depending on the nature of the active substance; no carriers are, however, required in the case of soft gelatin capsules). Suitable carrier materials for the preparation of solutions and syrups are, for example, water, polyols, saccharose, invert sugar and glucose. Suitable carrier materials for suppositories are, for example, natural or hardened oils, waxes, fats and semi-liquid or liquid polyols.

As pharmaceutical adjuvants there are contemplated the usual preservatives, solubilizers, stabilizers, wetting agents, emulsifiers, sweeteners, colorants, flavorings, salts for varying the osmotic pressure, buffers, coating agents and antioxidants.

The compounds of formula I and their acid addition salts or in vivo cleavable esters thereof can be used for parenteral administration and for this purpose are preferably made into preparations for injection as lyophilisates or dry powders for dilution with customary agents, such as water or isotonic common salt solution.

The compounds of formula I and their acid addition salts or in vivo cleavable esters thereof can be used for topical administration and for this purpose are preferably made into preparations as ointments, cremes or gels.

For the prevention and treatment of infectious diseases in mammals, human and non-human, a daily dosage of about 10 mg to about 2000 mg, especially about 50 mg to about 1000 mg, is usual, with those of ordinary skill in the art appreciating that the dosage will depend also upon the age, conditions of the mammals, and the kind of diseases being prevented or treated. The daily dosage can be administered in a single dose or can be divided over several doses. An average single dose of about 100 mg, 250 mg, 500 mg and 1000 mg can be contemplated.

The compounds of the present invention can be prepared by method well known in the art, e.g. by chemical modification of the readily available template molecule 2'-O-acetyl-4"-O-benzyloxy-carbonyl-6-O-methyl-11-deoxy-10,11-didehydroerythromycin A (6)

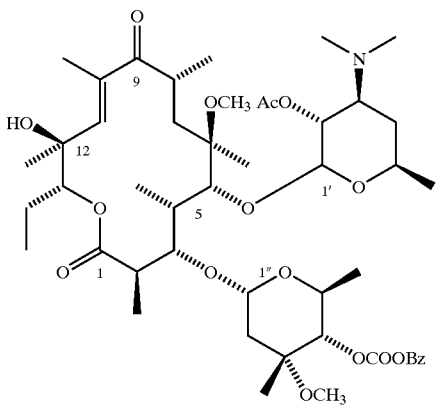

first described by Baker et al. in *J. Org. Chem.* 1988, 53, 2340–2345. The template molecule (6) was synthesized by means of modified procedures published by Baker et al. in *J. Org. Chem.* 1988, 53, 2340–2345 and Agouridas et al. in *J. Med. Chem.* 1998, 41, 4080–4100, i.e. starting from the semisynthetic 6-O-methyl derivative clarithromycin (2) according to the procedure depicted in Scheme 1.

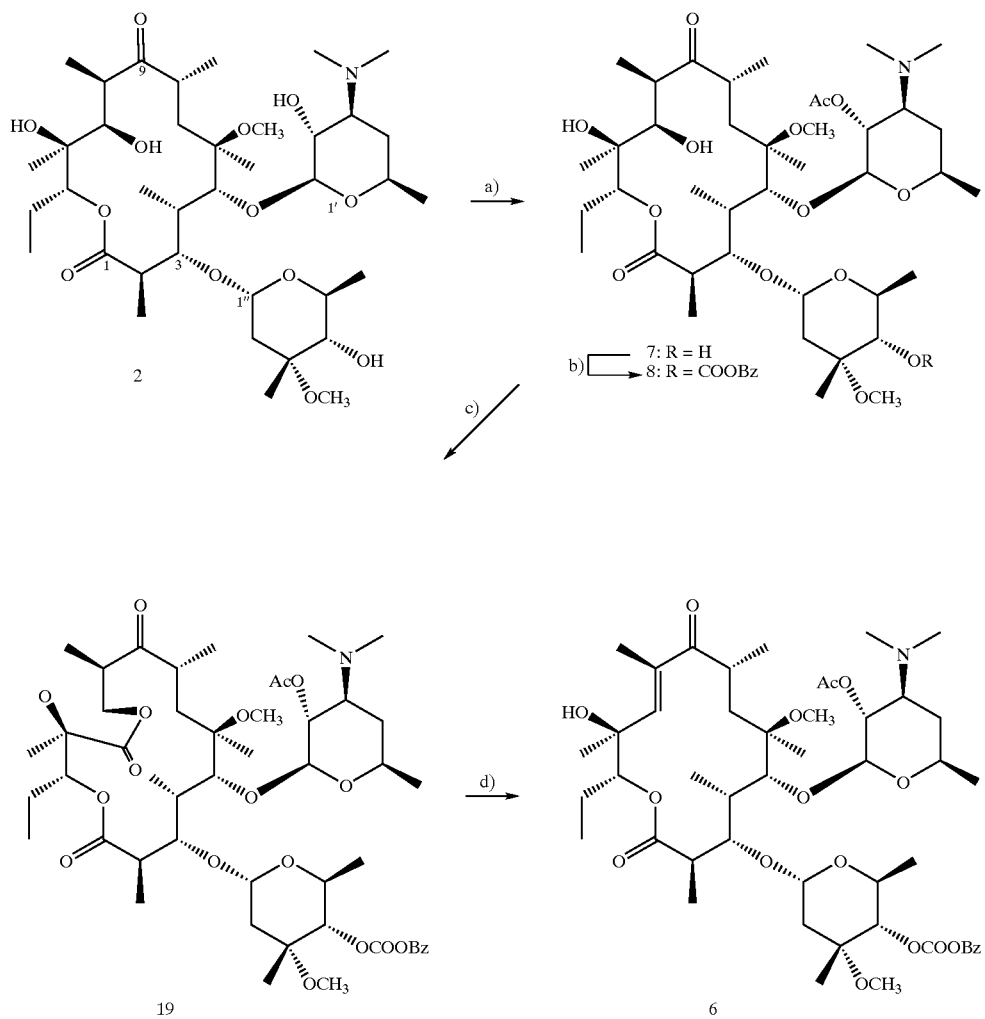

Scheme 1: Reagents and conditions: a) Ac$_2$O, CH$_2$Cl$_2$, room temp; b) PhCH$_2$OCOCl, DMAP, CH$_2$Cl$_2$, -30° C.; c) NaHMDS, 1-1'-carbonyldiimidazole (CDI), THF, -78° C.; d) DBU, benzene, reflux.

Scheme 1: Reagents and conditions: a) Ac$_2$O, CH$_2$Cl$_2$, room temp; b) PhCH$_2$OCOCl, DMAP, CH$_2$Cl$_2$, −30° C.; c) NaHMDS, 1,1′-carbonyldiimidazole (CDI), THF, −78° C.; d) DBU, benzene, reflux.

The 2′-hydroxy group of the desosamine moiety of clarithromycin (2) was selectively protected by treatment with acetic anhydride in methylene chloride without addition of base to give compound 7 in near quantitative yield. Subsequently, a benzyloxycarbonyl protecting group was introduced selectively to the 4″-hydroxy group by treatment of 7 with benzyl chloroformiate and 4-dimethylaminopyridine (DMAP) in methylene chloride at −30° C. to give doubly protected clarithromycin 8. Further treatment of 8 with sodium hexamethyldisilazane and carbonyldiimidazole in tetrahydrofuran (THF) at −78° C. gave cyclic carbonate 19. Cyclic carbonate 19 was subsequently subjected to β-elimination with 1,8-diazabicyclo[5.4.0]undec-7-ene (DBU) in refluxing benzene to give protected enone 6 in excellent yield.

According to the invention the protected enone (6) is then further reacted as depicted in reaction scheme 2

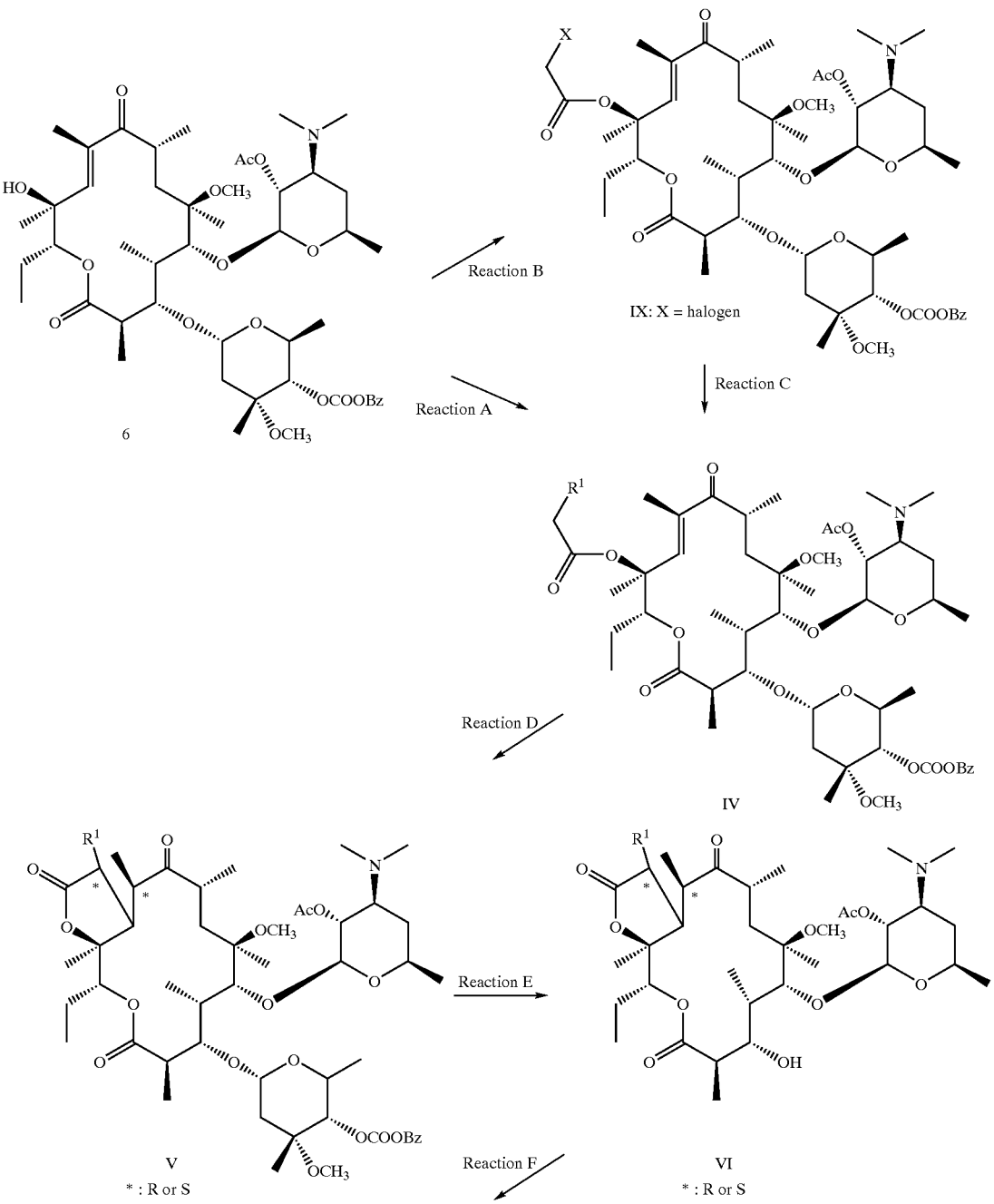

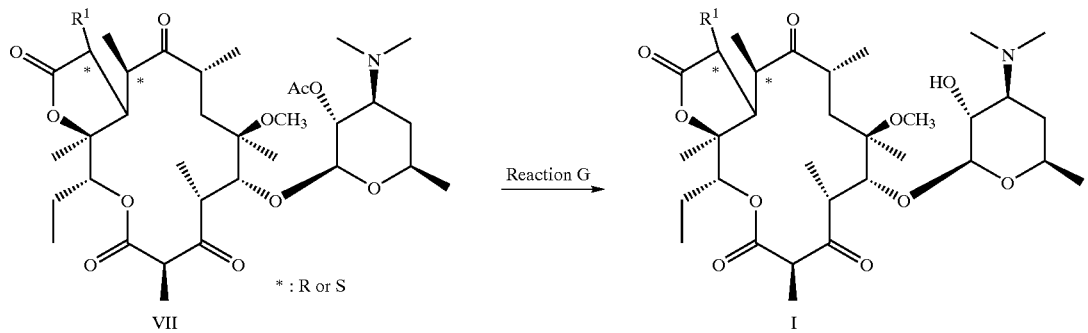

wherein the symbols are as defined above. "Ac" refers to an acetyl protecting group and "Bz" refers to a benzyl group.

The hydroxy group at position 12 of compound 6 is esterified by treatment with an appropriate carboxylic acid ($R^1COOH$), N,N'-dicylohexylcarbodiimide (DCC) and N,N'-dimethylaminopyridine (DMAP) in a chlorinated solvent such as methylene chloride or dichloroethane (reaction A). Following extractive work up, the crude product is purified by flash chromatography to give the corresponding ester with the general formula IV.

The same compound can be obtained in an alternative way by the following two reaction steps:

Compound 6 is esterified with a 2-haloacetic acid such as chloroacetic acid or bromoacetic acid (reaction B) under identical conditions as described above in reaction A to give haloacetyl derivative IX.

Haloacetyl derivative IX is then treated with a suitable thiol ($R^1H$) in the presence of a base such as 1,8-diazabicyclo[5.4.0]undec-7-ene (DBU), $K_2CO_3$, $NEt_3$, in acetone until no starting material remains (reaction C). The reaction typically lasts from 30 minutes to 3 hours. Following aqueous work up, the crude material is purified by silica gel flash chromatography to give the product IV in high yield. In a similar way, treatment of haloacetyl derivative IX with a tetraalkylammoniumcyanide such as tetraethylammoniumcyanide results in the formation of a compound with formula I wherein R1 is —CN.

Compound IV is then treated with an alkali metal base such as NaH or potassium tert.-butoxide in an aprotic solvent such as dimethylformamide (DMF) or tetrahydrofuran (THF) at temperatures ranging from –20° C. to 20° C. for 30 minutes to 5 hours (reaction D) until no starting material remains as judged by thin layer chromatography (TLC). The amount of base is usually 1 to 3 equivalents relative to the starting compound. The reaction mixture is then partitioned between diethylether and 0.5 M $KH_2PO_4$. The crude material isolated from the extraction step is further purified by silica gel flash chromatography to give the product V as a mixture of two diasteromers in various ratios.

Selective cleavage of the cladinose moiety of V is carried out by the methods known to the art with 1 to 5% HCl in an alcoholic solvent such as methanol or ethanol for 12 to 72 hours at a temperature preferably from –15° C. to 40° C. (reaction E). The solvent is then removed and the crude product is taken up in an appropriate organic solvent. The solution is washed with a basic aqueous solution ranging from pH 8–13. The crude product obtained from the extraction step is then further purified by silica gel flash chromatography to give VI as a mixture of two diasteromers in various ratios.

Oxidation of VI is carried out with 1,2-dichloroethane EDC.HCl, dimethoxy-sulfoxide (DMSO) and pyridinium trifluoroacetate in a chlorinated solvent such as methylene chloride or dichloroethane at temperatures ranging from –15° C. to room temperature for 1 to 5 hours as described by Agouridas et al. in J. Med. Chem. 1998, 41, 4080–4100, (reaction F). The reaction mixture is then quenched with $NaHCO_3$-solution, separated from the aqueous phase, dried and evaporated to give the crude product that is further purified by silica gel flash chromatography to give ketolide VII as a mixture of two diasteromers in various ratios.

The oxidation of VI can also be carried out using (1,1,1-triacetoxy)-1,1-dihydro-1,2-benziodoxol-3-(1H)-one (Dess-Martin reagent) in a chlorinated solvent such as methylene chloride at temperatures ranging from –20° C. to room temperature for 1 to 5 hours as described by S. F. Martin et al. in J. Am. Chem. Soc 1997, 119, 3193–3194.

Final deprotection of the 2'-hydroxy group of VII is achieved by stirring the compound in an alcoholic solvent such as methanol or ethanol for 12 to 72 hours (reaction G). The solvent is evaporated to give the desired deprotected product of formula I as a single diasteromer.

The following examples illustrate the present invention, but are not intended to be limiting in any manner.

Certain abbreviations are used repeatedly in the following specification. These include:

TLC for thin layer chromatography;
HPLC for high performance liquid chromatography;
DMSO for dimethylsulphoxide;
DBU for diazabicycloundecane;
DIPEA for diisopropylethylamine (Huenig's base);
DIAD for diisopropylazadicarboxylate;
DMF for dimethylformamide;
THF for tetrahydrofurane;
DCC for dicyclohexylcarbodiimide;
DMAP for 4-dimethylaminopyridine;
EDC.HCl for N-(3-dimethylaminopropyl)-N'-ethylcarbodiimide hydrochloride;
$R_f$ indicates the retention of the compound on thin layer chromatography;
KO$^t$Bu for potassium tert.-butylate;
MS for mass spectrometry;

NMR for nuclear magnetic resonance;
ISP for ion spray.

EXAMPLE 1

Preparation of (3S,3aR,4R,6R,8R,9R,10R,12R,15R,15aS)-15-Ethyloctahydro-8-methoxy-4,6,8,10,12,15a-hexamethyl-3-[[2-phenylethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone(I-1, Compound of Formula I, Wherein $R^1$ is [2-phenylethyl]thio)

A] [[2-Phenylethyl]thio]acetic acid was prepared from 2-phenylethanethiol and chloroacetic acid according to Weissbach et al., *Chem. Ber.* 1929, 62, 2423.

B] (10E)-10,11-Didehydro-11-deoxy-6-O-methyl-erythromycin 2'-acetate 4"-(phenylmethyl carbonate)12-[[[2-phenylethyl]thio]acetate] (IV-1):

To a solution of 300 mg (331 μmol) (10E)-10,11-didehydro-11-deoxy-6-O-methylerythromycin-2'-acetate-4"-(phenylmethyl carbonate) (6), 209 mg (994 μmol) of [[2-phenylethyl]thio]acetic acid and 80 mg DMAP in 10 ml $CH_2Cl_2$ kept under argon was added a solution of 200 mg (994 μmol) DCC in 5 ml $CH_2Cl_2$ dropwise over 6 hours by means of a syringe pump. Following addition, the solution was stirred a room temperature for farther 12 hours. The mixture was poured into 0.5 M $KH_2PO_4$ solution and extracted with $CH_2Cl_2$. The organic layer was washed with brine, dried over $Na_2SO_4$ and evaporated. The resulting semisolid was taken up in ethyl acetate (25 ml), filtered and evaporated to give an oil that was purified by flash chromatography (1% $NEt_3$ in ethyl acetate). Fractions containing pure product were combined, evaporated and dried under reduced pressure to give a colorless foam. Yield: 334 mg (92%). $R_f$: 0.35 (1% $NEt_3$ in ethyl acetate). $^1$H-NMR ($CDCl_3$) diagnostic signals only: 0.86 (t, 3H), 0.92 (d, 3H), 1.20 (s, 3H), 1.60 (s, 3H), 1.88 (s, 3H), 2.00 (s, 3H), 2.23 (s, 6H), 2.86 (s, 4H), 3.14 (s, 2H), 3.16 (s, 3H), 3.32 (s, 3H), 4.46 (d, 1H), 4.56 (d, 1H), 4.68 (dd, 1H), 4.98 (broad d, 1H), 5.13 (d, 1H), 5.26 (d, 1H), 5.74 (dd, 1H), 6.63 (s, 1H), 7.10–7.35 (m, 5H), 7.36 (s, 5H).

C] (3R or S,3aR,4R or S,6R,8R,9R,10S,11S,12R,15R,15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-3-[[2-phenylethyl]thio]-2H-furo[2,3-c]oxacyclotetradecin-2,5,13(3H,6H)-trione; mixture of 2 diastereomers (V-1):

To an ice cold solution of 321 mg (296 μmol) of ester IV-1 in 8.5 ml dry DMF kept under argon was added drop by drop 445 μl of a 1M solution of KO$^t$Bu in THF over 30 minutes. The resulting mixture was stirred at 0° C. for 60 minutes and then partitioned between diethylether and 0.5 M $KH_2PO_4$ solution. The organic layer was washed with 3% $NaHCO_3$ solution and brine, dried over $Na_2SO_4$ and evaporated. The crude product was purified by flash chromatography (1% $NEt_3$ in ethyl acetate). Evaporation of the appropriate fractions gave 135 mg (58%) of the product V-1 as a 2:1 mixture of two diastereomers. $R_f$: 0.31 (1% $NEt_3$ in ethyl acetate).

D] (3R or S,3aR,4R or S,6R,8R,9R,10S,11S,12R,15R,15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[[2-phenylethyl]thio]-2H-furo[2,3-c]oxacyclotetradecin-2,5,13(3H,6H)-trione; mixture of 2 diastereomers (VI-1):

185 mg (171 μmol) V-1 were dissolved in 15 ml methanol containing 3% HCl. The solution was kept at room temperature for 24 hours and evaporated. The crude hydrochloride salt was redissolved in $CH_2Cl_2$, washed with 5% $NaHCO_3$ and brine, dried ($Na_2SO_4$) and evaporated. Flash chromatography gave 113 mg (84%) VI-1 as a colorless glass. 2:1 Mixture of two diastereomers. $R_f$: 0.44 ($CH_3CN$/$CH_2Cl_2$/$NH_4OH$=1/1/0.01)

E] (3R or S,3aR,4R or S,6R,8R,9R,10R,12R,15R,15aS)-9-[[2-O-Acetyl-3,4,6-trideoxy-3-(dimethylamino)-β-D-xylo-hexopyranosyl]oxy]-15-ethyloctahydro-8-methoxy-4,6,8,10,12,15a-hexamethyl-3-[[2-phenylethyl]thio]-2H-furo[2,3-c]oxacyclotetradecin-2,5,11,13(3H,6H,12H)-tetrone; mixture of 2 diastereomers (VII-1):

To a suspension of 104 mg (131 μmol) VI-1, 168 mg EDC.HCl and 168 μl DMSO in 1.5 ml $CH_2Cl_2$ kept under argon was added a solution of 169 mg pyridinum trifluoroacetate in 3.0 ml $CH_2Cl_2$ over 15 minutes. The resulting yellow solution was stirred for 60 minutes and then poured into 5% $NaHCO_3$ solution. The organic layer was separated, washed with 3% $NaHCO_3$ and brine to remove excess DMSO, dried over $Na_2SO_4$ and evaporated. Flash chromatography gave the protected ketolide VII-1 as a 2:1 mixture of two diastereomers in quantitative yield. $R_f$: 0.44 ($CH_3CN$/$CH_2Cl_2$/$NH_4OH$=1/1/0.01)

F] (3S,3aR,4R,6R,8R,9R,10R,12R,15R,15aS)-15-Ethyloctahydro-8-methoxy-4,6,8,10,12,15a-hexamethyl-3-[[2-phenylethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone (I-1):

Protected ketolide VII-1 was dissolved in 10 ml methanol and stirred for 72 hours at room temperature. The solvent was removed to give the desired compound I-1 as a single diastereomer. MS (ISP): 748.5 (MH$^+$). $^1$H-NMR ($CDCl_3$) diagnostic signals only: 0.88 (t, 3H), 1.14 (2 d, 6H), 1.25 (d, 3H), 1.32 (s, 3H), 1.33 (d, 3H), 1.37 (d, 3H), 1.51 (s, 3H), 2.26 (s, 6H), 2.62 (s, 1H), 2.73 (s, 3H), 3.86 (q, 1H), 4.27 (d, 1H), 4.34 (d, 1H), 4.35 (s, 1H), 5.53 (dd, 1H), 7.13–7.28 (m, 5H).

EXAMPLE 2

Preparation of (3S,3aR,4R,6R,8R,9R,10R,12R,15R,15aS)-15-Ethyloctahydro-8-methoxy-4,6,8,10,12,15a-hexamethyl-3-[[2-phenylpropyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone (I-2, Compound of Formula I Where $R^1$ is [3-phenylpropyl]thio)

A] [[3-Phenylpropyl]thio]acetic acid was prepared from 3-phenylpropanethiol and chloroacetic acid according to Weissbach et al. *Chem. Ber.* 1929, 62, 2423.

B] (10E)-10,11-Didehydro-11-deoxy-6-O-methylerythromycin 2'-acetate 4"-(phenylmethyl carbonate) 12-[[[3-phenylpropyl]thio]acetate] (IV-2):

Was prepared in analogy to example 1B from 300 mg 6 and 209 mg [[3-phenylpropyl]thio]acetic acid. 334 mg of the desired product IV-2 were obtained. $R_f$: 0.47 (1% $NEt_3$ in ethyl acetate). $^1$H-NMR ($CDCl_3$) diagnostic signals only: 0.87 (t, 3H), 0.92 (d, 3H), 1.20 (s, 3H), 1.58 (s, 3H), 1.87 (s, 3H), 1.90 (m, 2H), 2.23 (s, 6H), 2.59 (t, 2H), 2.69 (t, 2H), 3.14 (s, 2H), 3.16 (s, 3H), 3.32 (s, 3H), 4.36 (m, 1H), 4.47

(d, 1H), 4.57 (d, 1H), 4.68 (dd, 1H), 4.98 (d, 1H), 5.13 (d, 1H), 5.26 (d, 1H), 5.73 (dd, 1H), 6.63 (s, 1H), 7.12–7.33 (m, 5H), 7.33 (s, 5H).

C] (3R or S,3aR,4R or S,6R,8R,9R,10S,11S,12R,15R, 15aS)-9-[[2-O-Acetyl-3,4,6-trideoxy-3-((dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4, 6,8,10,12,15a-hexamethyl-3-[[3-phenylpropyl]thio]-2H-furo[2,3-c]oxacyclotetradecin-2,5,13(3H,6H)-trione; mixture of 2 diastereomers (V-2):

Cyclization of 316 mg IV-2 as described in example 1C with 431 μl KO$^t$Bu in 8.5 ml DMF gave 165 mg of the desired product V-2 as a 1.5:1 mixture of two diasteromers. $R_f$: 0.37 (1% NEt$_3$ in ethyl acetate).

D] (3R or S,3aR,4R or S,6R,8R,9R,10S,11S,12R,15R, 15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[[2-phenylpropyl]thio]-2H-furo[2,3-c]oxacyclotetradecin-2,5, 13(3H,6H)-trione; mixture of two diastereomers (VI-2):

According to example 1D, 165 mg of V-2 were subjected to methanolysis to give 95 mg of product VI-2 as a 1.5:1 mixture of two diastereomers. $R_f$: 0.30 (CH$_3$CN/CH$_2$Cl$_2$/NH$_4$OH 1:1:0.01). $^1$H-NMR (CDCl$_3$) diagnostic signals only: Diastereomer 1; 2.07 (s, 3H), 2.26 (s, 6H), 3.05 (s, 3H), 3.74 (d, 1H), 4.47 (s, 1H), 5.63 (dd, 1H); diastereomer 2; 2.08 (s, 3H), 2.24 (s, 6H), 3.07 (s, 3H), 3.84 (d, 1H), 3.92 (d, 1H), 5.00 (dd, 1H).

E] (3R or S,3aR,4R or S,6R,8R,9R,10R,12R,15R,15aS)-9-[[2-O-Acetyl-3,4,6-trideoxy-3-(dimethylamino)-β-D-xylo-hexopyranosyl]oxy]-15-ethyloctahydro-8-methoxy-4, 6,8,10,12,15a-hexamethyl-3-[[2-phenylpropyl]thio]-2H-furo[2,3-c]oxacyclotetradecin-2,5,11,13(3H,6H,12H)-tetrone; (VII-2):

95 mg VI-2 were oxidized as described in example 1E to give 84 mg of VII-2 as a 1.5:1 mixture of two diastereomers. $R_f$: 0.44 (CH$_3$CN/CH$_2$Cl$_2$/NH$_4$OH 1:1:0.01). $^1$H-NMR (CDCl$_3$) diagnostic signals only: Diastereomer 1; 2.05 (s, 3H), 2.25 (s, 6H), 2.79 (s, 3H), 3.83 (q, 1H), 5.54 (dd, 1H); diastereomer 2; 2.02 (s, 3H), 2.23 (s, 6H), 2.79 (s, 3H), 3.77 (q, 1H), 4.98 (dd, 1H).

F] (3S,3aR,4R,6R,8R,9R,10R,12R,15R,15aS)-15-Ethyloctahydro-8-methoxy-4,6,8,10,12,15a-hexamethyl-3-[[2-phenylpropyl]thio]-9-[[3,4,6-trideoxy-3-(dimethylamino)-β-D-xylo-hexopyranosyl]oxy]-2H-furo[2, 3-c]oxacyclotetradecin-2,5,11,13(3H,6H,12H)-tetrone; (I-2):

Final deprotection of 84 mg VII-2 in methanol gave I-2 as a single diastereomer. MS (ISP): 762.4 (MH$^+$). $^1$H-NMR (CDCl$_3$) diagnostic signals only: 0.89 (t, 3H), 1.11 (d, 3H), 1.13 (d, 3H), 1.24 (d, 3H), 1.32 (s, 3H), 1.33 (d, 3H), 1.38 (d, 3H), 1.51 (s, 3H), 2.03 (m, 2H), 2.27 (s, 6H), 2.62 (s, 1H), 2.80 (s, 3H), 3.86 (q, 1H), 4.26 (s, 1H), 4.28 (d, 1H), 4.33 (1H), 5.53 (dd, 1H), 7.12–7.32 (m, 5H).

EXAMPLE 3

Preparation of (3S,3aR,4R,6R,8R,9R,10R,12R,15R,15aS)-15-Ethyloctahydro-8-methoxy-4,6,8,10,12,15a-hexamethyl-3-[phenylthio]-9-[[3,4,6-trideoxy-3-(dimethylamino)-β-D-xylo-hexopyranosyl]oxy]-2H-furo[2, 3-c]oxacyclotetradecin-2,5,11,13(3H,6H,12H)-tetrone; (I-3, Compound of Formula I, Where R$^1$ is Phenylthio)

A] (10E)-10,11-Didehydro-11-deoxy-6-O-methyl-erythromycin 2'-acetate 4"-(phenylmethyl carbonate)12-[[phenylthio]acetate] (IV-3):

In analogy to example 1B, coupling of 300 mg 6 and 278 mg phenylthioacetic acid gave 260 mg of the desired product IV-3. $R_f$: 0.55 (CH$_3$CN/CH$_2$Cl$_2$/NH$_4$OH 1:1:0.01). MS (ISP): 1056.4 MH$^+$). $^1$H-NMR (CDCl$_3$) diagnostic signals only: 0.79 (t, 3H), 1.54 (s, 3H), 1.80 (s, 3H), 2.00 (s, 3H), 2.23 (s, 6H), 3.12 (s, 3H), 3.32 (s, 3H), 3.59 (s, 2H), 4.34 (m, 1H), 4.45 (d, 1H), 4.55 (d, 1H), 4.68 (dd, 1H), 4.97 (d, 1H), 5.13 (d, 1H), 5.24 (d, 1H), 5.66 (dd, 1H), 6.59 (s, 1H), 7.18–7.43 (m, 5H).

B] (3R or S,3aR,4R or S,6R,8R,9R,10S,11S,12R,15R, 15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8, 10,12,15a-hexamethyl-3-[phenylthio]-2H-furo[2,3-c] oxacyclotetradecin-2,5,13(3H,6H)-trione; mixture of two diastereomers (V-3):

According to example 1C, cyclization of 150 mg IV-3 gave 69 mg of the desired product V-3 as a 3:1 mixture of two diastereomers: $R_f$: 0.46 (CH$_3$CN/CH$_2$Cl$_2$/NH$_4$OH 1:1:0.01).

C] (3R or S,3aR,4R or S,6R,8R,9R,10S,11S,12R,15R, 15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[phenylthio]-2H-furo[2,3-c]oxacyclotetradecin-2,5,13(3H, 6H)-trione; mixture of two diastereomers (VI-3):

70 mg V-3 were cleaved according to example 1D to give 32 mg of pure product VI-3 as a 3:1 mixure of two diastereomers. $R_f$: 0.17 (CH$_3$CN/CH$_2$Cl$_2$/NH$_4$OH 1:1:0.01). $^1$H-NMR (CDCl$_3$) diagnostic signals only: Diastereomer 1; 1.47 (s, 3H), 2.08 (s, 3H), 2.26 (s, 6H), 2.88 (s, 1H), 3.10 (s, 3H), 3.77 (d, 1H), 4.85 (s, 1H), 5.48 (dd, 1H), 7.73 (m, 2H); diasteromer 2; 1.52 (s, 3H), 2.08 (s, 3H), 2.24 (s, 6H), 3.11 (s, 3H), 3.83 (d, 1H), 4.44 (s, 1H), 5.05 (dd, 1H), 7.47 (m, 2H).

D] (3R or S,3aR,4R or S,6R,8R,9R,10R,12R,15R,15aS)-9-[[2-O-Acetyl-3,4,6-trideoxy-3-(dimethylamino)-β-D-xylo-hexopyranosyl]oxy]-15-ethyloctahydro-8-methoxy-4, 6,8,10,12,15a-hexamethyl-3-[phenylthio]-2H-furo[2,3-c] oxacyclotetradecin-2,5,11,13(3H,6H,12H)-tetrone; (VII-3):

30 mg VI-3 were oxidized according to example 1E to give 30 mg of the protected ketolide VII-3 as a 3:1 mixture of two diastereomers. $R_f$: 0.50 (CH$_3$CN/CH$_2$Cl$_2$/NH$_4$OH 1:1:0.01).

E] (3S,3aR,4R,6R,8R,9R,10R,12R,15R,15aS)-15-Ethyloctahydro-8-methoxy-4,6,8,10,12,15a-hexamethyl-3-[phenylthio]-9-[[3,4,6-trideoxy-3-(dimethylamino)-β-D-xylo-hexopyranosyl]oxy]-2H-furo[2,3-c] oxacyclotetradecin-2,5,11,13 (3H,6H,12H)-tetrone; (I-3):

In analogy to example 1F, 30 mg VII-3 were deprotected to give the desired product I-3 (30 mg) as a single diastereomer. $R_f$: 0.43 (CH$_3$CN/CH$_2$Cl$_2$/NH$_4$OH 1:1:0.01). MS (ISP): 720.5 (MH$^+$). $^1$H-NMR (CDCl$_3$) diagnostic signals only: 0.93 (t, 3H), 1.09 (t, 3H), 1.13 (t, 3H), 1.26 (t, 3H), 1.34 (d, 3H), 1.35 (s, 3H), 1.40 (d, 3H), 1.52 (s, 3H), 2.27 (s, 6H), 2.82 (s, 1H), 2.86 (s, 3H), 3.08 (q, 1H), 3.10–3.22 (m, 2H), 3.57 (m, 1H), 3.87 (q, 1H), 4.30 (d, 1H), 4.35 (d, 1H), 4.62 (s, 1H), 5.38 (dd, 1H), 7.28–7.37 (m, 3H), 7.70 (dd, 2H).

EXAMPLE 4
Preparation of (3S,3aR,4R,6R,8R,9R,10R,12R,15R,15aS)-15-Ethyloctahydro-8-methoxy-4,6,8,10,12,15a-hexamethyl-3-[(phenylmethyl)thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone (I-4, Compound of Formula I, Where $R^1$ is [phenylmethyl]thio)

A] (10E)-10,11-Didehydro-11-deoxy-6-O-methyl-erythromycin 2'-acetate 4"-(phenylmethyl carbonate)12-[[(phenylmethyl)thio]acetate] (IV-4):

In analogy to example 1B, coupling of 500 mg 6 and 503 mg [(phenylmethyl)thio]-acetic acid gave 600 mg of the desired product IV-4. $R_f$: 0.71 (CH$_3$CN/CH$_2$Cl$_2$/NH$_4$OH 1:1:0.01). $^1$H-NMR (CHCl$_3$) diagnostic signals only: 1.60 (s, 3H), 1.86 (s, 3H), 2.02 (s, 3H), 2.23 (s, 6H), 2.99 (s, 2H), 3.17 (s, 3H), 3.33 (s, 3H), 3.78 (s, 2H), 4.37 (m, 1H), 4.46 (d, 1H), 4.77 (d, 1H), 4.68 (dd, 1H), 4.98 (d, 1H), 5.13 (d, 1H), 5.25 (d, 1H), 5.77 (dd, 1H), 6.64 (s, 1H), 7.20–7.35 (m, 5H), 7.36 (s, 5H).

B] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-3-[(phenylmethyl)thio]-2H-furo[2,3-c]oxacyclotetradecin-2,5,13(3H,6H)-trione; (V-4):

146 mg IV-4 were cyclized according to example 1C to give 75 mg of the desired product V-4 as a single diastereomer. $R_f$: 0.65 (CH$_3$CN/CH$_2$Cl$_2$/NH$_4$OH 1:1:0.01). $^1$H-NMR (CHCl$_3$) diagnostic signals only: 2.04 (s, 3H), 2.24 (s, 6H), 2.55 (s, 1H), 3.05 (s, 3H), 3.33 (s, 3H), 4.05 (d, 1H), 4.18 (d, 1H), 4,31 (s, 1H), 4.46 (d, 1H), 4.62 (d, 1H), 4.71 (dd, 1H), 4.92 (d, 1H), 5.12 (d, 1H), 5.27 (d, 1H), 5.53 (dd, 1H), 7.20–7.47 (m, 5H), 7.36 (s, 5H).

C] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[(phenylmethyl)thio]-2H-furo[2,3-c]oxacyclotetradecin-2,5,13(3H,6H)-trione; (VI-4):

75 mg V-4 were subjected to methanolysis as described in example 1D to give 46 mg of product VI-4: $R_f$: 0.33 (CH$_3$CN/CH$_2$Cl$_2$/NH$_4$OH 1:1:0.01). $^1$H-NMR (CHCl$_3$) diagnostic signals only: 0.86 (t, 3H), 0.96 (d, 3H), 1.44 (s, 3H), 2.07 (s, 3H), 2.26 (s, 6H), 2.66 (s, 1H), 3.00 (s, 3H), 3.28 (m, 2H), 3.72 (d, 1H), 4.08 (d, 1H), 4.18 (d, 1H), 4.41 (s, 1H), 4.62 (d, 1H), 4.77 (dd, 1H), 5.64 (dd, 1H), 7.21–7.47 (m, 5H), D] (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-15-ethyloctahydro-8-methoxy-4,6,8,10,12,15a-hexamethyl-3-[(phenylmethyl)thio]-2H-furo[2,3-c]oxacyclotetradecin-2,5,11,13(3H,6H,12H)-tetrone; (VII-4):

46 mg VI-4 were oxidized as described in example 1E to give 44 mg of VII-4. $R_f$: 0.61 (CH$_3$CN/CH$_2$Cl$_2$/NH$_4$OH 1:1:0.01). $^1$H-NMR (CHCl$_3$) diagnostic signals only: 0.88 (t, 3H), 1.03 (d, 1H), 1.09 (d, 3H), 1.16 (d, 3H), 1.25 (d, 3H), 1.27 (s, 3H), 1.35 (d, 3H), 1.49 (s, 3H), 2.04 (s, 3H), 2.24 (s, 6H), 2.62 (s, 1H), 2.75 (s, 3H), 3.37 (m, 1H), 3.82 (q, 1H), 4.03 (d, 1H), 4.17 (d, 1H), 4.21 (s, 1H), 4.23 (d, 1H), 4.41 (d, 1H), 4.75 (dd, 1H), 5.54 (dd, 1H), 7.21–7.43 (m, 5H).

E] (3S,3aR,4R,6R,8R,9R,10R,12R,15R,15aS)-15-Ethyloctahydro-8-methoxy-4,6,8,10,12,15a-hexamethyl-3-[(phenylmethyl)thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-4):

Final deprotection of 44 mg VII-4 was accomplished as described in example 1F to give 39 mg of I-4. $R_f$: 0.47 (CH$_3$CN/CH$_2$Cl$_2$/NH$_4$OH 1:1:0.01). MS (ISP): 734.4 (MH$^+$). $^1$H-NMR (CHCl$_3$) diagnostic signals only: 0.88 (t, 3H), 1.03 (d, 3H), 1.09 (d, 3H), 1.24 (d, 3H), 1.30 (s, 3H), 1.31 (d, 3H), 1.49 (s, 3H), 2.26 (s, 6H), 2.59 (s, 1H), 2.75 (s, 3H), 3.57 (m, 1H), 4.83 (q, 1H), 4.02 (d, 1H), 4.15 (d, 1H), 4.18 (s, 1H), 4.25 (d, 1H), 4.33 (d, 1H), 5.53 (dd, 1H), 7.20–7.43 (m, 5H).

EXAMPLE 5
Preparation of (3S,3aR,4R,6R,8R,9R,10R,12R,15R,15aS)-15-Ethyloctahydro-8-methoxy-4,6,8,10,12,15a-hexamethyl-3-[methylthio]-9-[[3,4,6-trideoxy-3-(dimethylamino)-β-D-xylo-hexopyranosyl]oxy]-2H-furo[2,3-c]oxacydotetradecin-2,5,11,13(3H,6H,12H)-tetrone; (I-5, Compound of Formula I, Where $R^1$ is Methylthio)

A] (10E)-10,11-Didehydro-11-deoxy-6-O-methyl-erythromycin 2'-acetate 4"-(phenylmethyl carbonate)12-[[methylthio]acetate]; (IV-5):

In analogy to example 1B, 568 mg (100%) of the desired product IV-5 were obtained from 500 mg (552 μmol) 6 and 293 mg methylthioacetic acid. $R_f$: 0.7 (CH$_3$CN/CH$_2$Cl$_2$/NH$_4$OH 1:1:0.01). $^1$H-NMR (CDCl$_3$) diagnostic signals only: 1.20 (s, 3H), 1.61 (s, 3H), 2.00 (s, 3H), 2.16 (s, 3H), 2.23 (s, 6H), 3.13 (s, 2H), 3.16 (s, 3H), 3.32 (s, 3H), 4.35 (M, 1H), 4.46 (d, 1H), 4.57 (d, 1H), 4.69 (dd, 1H), 4.98 (d, 1H), 5.13 (d, 1H), 5.24 (d, 1H), 5.74 (dd, 1H), 6.63 (s, 1H), 7.36 (s, 5H).

B] (3R or S,3aR,4R or S,6R,8R,9R,10S,11S,12R,15R,15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-3-[methylthio]-2H-furo[2,3-c]oxacyclotetradecin-2,5,13(3H,6H)-trione; mixture of 2 diastereomers (V-5):

In analogy to example 1C, 300 mg IV-5 were treated with 453 μl KO$^t$BU solution (1M). 165 mg (55%) of product V-5 was obtained as a 9:1 mixture of two diastereomers. $R_f$: 0.66 (CH$_3$CN/CH$_2$Cl$_2$/NH$_4$OH 1:1:0.01). $^1$H-NMR (CDCl$_3$) main product, diagnostic signals only: 2.04 (s, 3H), 2.24 (s, 6H), 2.42 (s, 3H), 2.53 (s, 1H), 3.07 (s, 3H), 3.34 (s, 3H), 4.26 (s, 1H), 4.29 (m, 1H), 4.47 (d, 1H), 4.63 (d, 1H), 4.72 (dd, 1H), 4.94 (d, 1H), 5.13 (d, 1H), 5.26 (d, 1H), 7.35 (s, 5H).

C] (3R or S,3aR,4R or S,6R,8R,9R,10S,11S,12R,15R,15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[methylthio]-2H-furo[2,3-c]oxacyclotetradecin-2,5,13(3H,6H)-trione; mixture of 2 diastereomers (VI-5):

In analogy to example 1D, 146 mg V-5 were treated with HCl in methanol to give 96 mg (93%) of the desired product VI-6 as a 9:1 mixture of diastereomers. $R_f$: 0.31 (CH$_3$CN/CH$_2$Cl$_2$/NH$_4$OH 1:1:0.01). $^1$H-NMR (CDCl$_3$) main product, diagnostic signals only: 0.86 (t, 3H), 0.97 (d, 3H), 1.09 (2 d, 6H), 1.23 (d, 3H), 1.26 (s, 3H), 1.27 (d, 3H), 1.45 (s, 3H), 2.07 (3H), 2.26 (s, 6H), 2.43 (s, 3H), 2.65 (s, 1H), 3.03 (s, 3H), 3.47 (m, 2H), 3.74 (d, 2H), 4.36 (s, 1H), 4.63 (d, 1H), 4.77 (dd, 1H), 5.67 (dd, 1H).

D] (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-15-ethyloctahydro-8-methoxy-4,6,8,10,12,15a-hexamethyl-3-[methylthio]-2H-furo[2,3-c]oxacyclotetradecin-2,5,11,13(3H,6H,12H)-tetrone; (VII-5):

In analogy to example 1E, 90 mg (VI-5) were oxidized to give 87 mg of the protected ketolide VII-5. $R_f$: 0.61 ($CH_3CN/CH_2Cl_2/NH_4OH$ 1:1:0.01). $^1H$-NMR ($CDCl_3$) diagnostic signals only: 0.88 (t, 3H), 1.11 (d, 3H), 1.13 (d, 3H), 1.18 (d, 3H), 1.25 (d, 3H), 1.28 (s, 3H), 1.36 (d, 3H), 1.50 (s, 3H), 2.05 (s, 3H), 2.25 (s, 6H), 2.40 (s, 3H), 2.60 (s, 1H), 2.76 (s, 3H), 2.98–3.18 (m, 2H), 3.57 (m, 1H), 3.83 (q, 1H), 4.18 (s, 1H), 4.25 (d, 1H), 4.41 (d, 1H), 4.75 (dd, 1H), 5.58 (dd, 1H).

E] (3S,3aR,4R,6R,8R,9R,10R,12R,15R,15aS)-15-Ethyloctahydro-8-methoxy-4,6,8,10,12,15a-hexamethyl-3-[methylthio]-9-[[3,4,6-trideoxy-3-(dimethylamino)-β-D-xylo-hexopyranosyl]oxy]-2H-furo[2,3-c]oxacyclotetradecin-2,5,11,13 (3H,6H,12H)-tetrone; (I-5):

Final deprotection of 87 mg (VII-5) was accomplished as described in example 1F to give 66.4 mg (81%) of I-5 as a single diastereomer. MS (ISP): 658.2 ($MH^+$). $^1H$-NMR ($CDCl_3$) diagnostic signals only: 0.88 (t, 3H), 1.11 (d, 3H), 1.13 (d, 3H), 1.25 (d, 3H), 1.31 (s, 3H), 1.32 (d, 3H), 1.37 (d, 3H), 1.51 (s, 3H), 2.27 (s, 6H), 2.41 (s, 3H), 2.58 (s, 1H), 2.77 (s, 3H), 3.03 (q, 1H), 3.11 (m, 1H), 3.19 (dd, 1H), 3.58 (m, 1H), 3.85 (q, 1H), 4.16 (s, 1H), 4.27 (d, 1H), 4.33 (d, 1H), 5.58 (dd, 1H).

EXAMPLE 6

Preparation of (3S,3aR,4R,6R,8R,9R,10R,12R,15R,15aS)-15-Ethyloctahydro-8-methoxy-4,6,8,10,12,15a-hexamethyl-3-[[2-[2,4-1H,3H-pyriminedione-1-yl]ethyl]-thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-6, Compound of Formula I, Where $R^1$ is [2-[2,4-1H,3H-pyrimidinedione-1-yl]ethyl]thio)

Synthesis of the side chain precursor required for this ketolide is outlined in Scheme 3 (steps A–C).

Scheme 3:

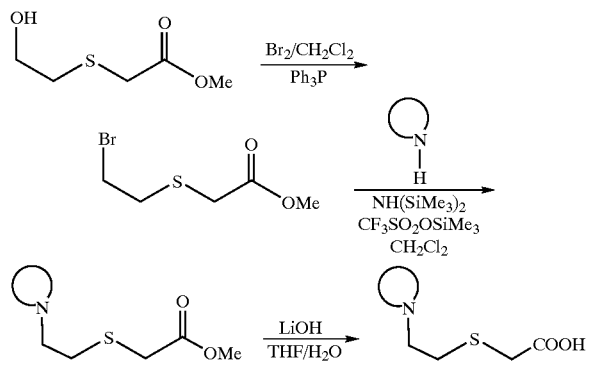

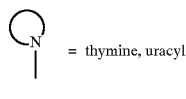
= thymine, uracyl

A] [[2-Bromoethyl]thio]acetic acid methyl ester:

[[2-Hydroxyethyl]thio]acetic acid methyl ester (3.39 g, 20 mmol), synthesized according to Ueda, Chem. Pharm. Bull. 1990, 38, 3035–3041 and 6.29 g (20 mmol) triphenylphosphine were dissolved in 50 ml $CH_2Cl_2$ and cooled to 0° C. Bromine (1.13 ml, 22 mmol) was added dropwise and the mixture was allowed to warm to room temperature. The solution was heated to reflux for 3 hours, cooled and quenched by slow addition of aqueous $NaHCO_3$ solution until the color disappeared. The organic phase was separated, dried ($Na_2SO_4$) and concentrated. The residual semisolid was triturated with hexanes, filtered and evaporated to give an oil, that was distilled bulb to bulb to give 3.0 g of a colorless oil. Bp: 100° C. (0.3 mm Hg).

B] [[2-[2,4-(1H,3H)-Pyrimidinedione-1-yl]ethyl]thio] acetic acid methyl ester: 3.36 g uracil and 2 mg $(NH_4)_2SO_4$ were suspended in 25 ml hexamethyldisilazane with stirring and the mixture was heated to reflux for 3 hours. A clear solution resulted. This was concentated in vacuo and 75 ml dichloroethane, 5.33 g methyl [[2-bromoethyl]thio]acetic acid methyl ester and 6.67 g trimethylsilyltrifloromethanesulfonate were added to the residue. The mixture was stirred at room temperature for 60 minutes and then kept at 60° C. for further 20 hours. The solution was diluted with dichloroethane, washed with aqueous $NaHCO_3$ and water, dried ($Na_2SO_4$) and evaporated. The residue was purified by flash chromatography (gradient of 0–10% ethanol in $CH_2Cl_2$) to give, after trituration with isopropyl ether and drying 4.2 g of a solid. Mp: 90° C.

C] ] [[2-[2,4-(1H,3H)-Pyrimidinedione-1-yl]ethyl]thio] acetic acid:

4.0 g [[2-[2,4-(1H,3H)-pyrimidinedione-1-yl]ethyl]thio] acetic acid methyl ester was dissolved in THF (116 ml) and water (85 ml) and 3.15 g LiOH was added. The mixture was stirred at room temperature for 2 hours and THF was removed in vacuo. The pH was adjusted to 2–3 by addition of 1N HCl and the solution was saturated with NaCl. The product was extracted into ethyl acetate and the organic extracts were dried and evaporated to give 2.6 g of a solid. This was recrystallized from ethanol to give 1.56 g of the desired product. Mp: 145° C. MS (EI): 230.1 ($M^+$). $^1H$-NMR (DMSO-d6): 2.84 (t, 2H), 3.33 (s, 2H), 3.86 (t, 2H), 5.55 (dd, 1H), 7.65 (d, 1H), 11.25 (s, 1H), 12.63 (s, 1H).

D] (10E)-10,11-Didehydro-11-deoxy-6-O-methyl-erythromycin 2'-acetate 4"-(phenylmethyl carbonate)12-[[[2-[2,4-(1H,3H)-pyrimidinedione-1-yl]ethyl]-thio] acetate]; (IV-6):

Compound IV-6 was synthesized from 500 mg 6 and [[2-[2,4-1H,3H-pyrimidinedione-1-yl]ethyl]thio]-acetic acid as described in example 1B except with the following difference: IV-6 and DMAP were dissolved in 15 ml $CH_2Cl_2$/dioxane 1:1 and simultaneously, a solution of [[2-[2,4-(1H,3H)-pyrimidinedione-1-yl]ethyl]thio]acetic acid in 8.5 ml dioxane and a solution of DMAP in 8.5 ml $CH_2Cl_2$ were added over 6 hours by means of a syringe pump. Yield: 355 mg (58%). $R_f$: 0.36 ($CHCl_3/MeOH/NH_4OH$ 9:1:0.1). MS (ISP): 1118.5 ($MH^+$). $^1H$-NMR ($CDCl_3$) diagnostic signals only: 1.62 (s, 3H), 1.89 (s, 3H), 2.01 (s, 3H), 2.24 (s, 6H), 2.90 (t, 2H), 3.15 (s, 3H), 3.21 (s, 2H), 3.33 (s, 3H), 3.91 (t, 2H), 3.36 (m, 1H), 4.46 (d, 1H), 4.57 (d, 1H), 4.69 (dd, 1H), 4.98 (d, 1H), 5.14 (d, 1H), 5.26 (d, 1H), 5.69 (d, 1H), 5.73 (dd, 1H), 6.60 (dd, 1H), 7.25 (d, 1H), 7.36 (s, 5H), 8.48 (broad s, 1H).

E] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-3-[[2-[2,4-1H,3H-pyrimidinedione-1-yl]ethyl]thio]-2H-furo[2,3-c]oxacyclotetradecin-2,5,13 (3H,6H)-trione; (V-6):

Cyclization of 258 mg IV-6 was performed in DMF as described in example 1C, except that KO$^t$Bu-solution was replaced with 30 mg NaH (dispersion 60%). This procedure gave 70 mg pure product V-6 as a single diastereomer. R$_f$: 0.44 (CHCl$_3$/MeOH/NH$_4$OH 9:1:0.1). MS (ISP): 1118.5 (MH$^+$). $^1$H-NMR (CDCl$_3$) diagnostic signals only: 1.32 (s, 3H), 1.44 (s, 3H), 2.04 (s, 3H), 2.45 (s, 6H), 2.53 (s, 1H), 3.01 (s, 3H), 3.33 (s, 3H), 4.36 (s, 1H), 4.47 (d, 1H), 4.63 (d, 1H), 4.72 (dd, 1H), 4.93 (d, 1H), 5.12 (d, 1H), 5.27 (d, 1H), 5.41 (dd, 1H), 5.62 (d, 1H), 7.36 (s, 5H), 7.84 (d, 1H), 8.38 (broad s, 1H).

F] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[[2-[2,4-1H,3H-pyrimidinedione-1-yl]ethyl]thio]-2H-furo[2,3-c]oxacyclotetradecin-2,5,13 (3H,6H)-trione; (VI-6)

70 mg V-6 were cleaved according to example 1D to give 43 mg VI-6. R$_f$: 0.40 (ethyl acetate/methanol/NEt$_3$ 9:1:0.1). MS (ISP): 826.3 (MH$^+$). $^1$H-NMR (CDCl$_3$) diagnostic signals only: 0.85 (t, 3H), 0.97 (d, 3H), 0.12 (2 d, 6H), 1.27 (s, 3H), 1.47 (s, 3H), 2.07 (s, 3H), 2.26 (s, 6H), 2.63 (s, 1H), 2.96 (s, 3H), 3.74 (d, 1H), 3.89 (m, 1H), 4.33 (dt, 1H), 4.46 (1H), 4.61 (d, 1H), 4.77 (dd, 1H), 5.50 (dd, 1H), 5.60 (d, 1H), 7.78 (d, 1H), 8.55 (broad s, 1H).

G] (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-15-ethyloctahydro-8-methoxy-4,6,8,10,12,15a-hexamethyl-3-[[2-[2,4-1H,3H-pyrimidinedione-1-yl]ethyl]thio]-2H-furo[2,3-c]oxacyclotetradecin-2,5,11,13(3H,6H,12H)-tetrone; (VII-6):

Oxidation of 43 mg VI-6 was done as described in example 1E to give 37 mg of protected ketolide VII-6. R$_f$: 0.35 (CHCl$_3$/MeOH/NH$_4$OH 9:1:0.1). MS (ISP): 824.2 (MH$^+$). $^1$H-NMR (CDCl$_3$) diagnostic signals only: 0.87 (t, 3H), 1.29 (s, 3H), 1.35 (d, 3H), 1.52 (s, 3H), 2.04 (s, 3H), 2.25 (s, 6H), 2.61 (s, 1H), 2.69 (s, 3H), 3.45 (dt, 1H), 3.57 (m, 1H), 3.82 (q, 1H), 3.83 (m, 1H), 4.27 (d, 1H), 4.28 (s, 1H), 4.33 (m, 1H), 4.41 (d, 1H), 4.76 (dd, 1H), 5.42 (dd, 1H), 5.61 (d, 1H), 7.80 (d, 1H), 8.53 (broad s, 1H).

H] (3S,3aR,4R,6R,8R,9R,10R,12R,15R,15aS)-15-Ethyloctahydro-8-methoxy-4,6,8,10,12,15a-hexamethyl-3-[[2-[2,4-1H,3H-pyrimidinedione-1-yl]ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-6):

In analogy to example 1F, final deprotection of 37 mg VII-6 gave 35 mg pure I-6. MS (ISP): 782.2 (MH$^+$). $^1$H-NMR (CDCl$_3$) diagnostic signals only: 0.88 (t, 3H), 1.14 (2d, 6H), 1.27 (d, 3H), 1.31 (s, 3H), 1.32 (d, 3H), 1.36 (d, 3H), 1.53 (s, 3H), 2.27 (s, 6H), 2.59 (s, 1H), 2.70 (s, 3H), 3.46 (dt, 1H), 3.46–3.62 (m, 2H), 3.84 (q, 1H), 3,84 (m, 1H), 4.27 (s, 1H), 4.28 (d, 1H), 4.34 (d, 1H), 4.27–4.40 (m, 1H), 5.41 (dd, 1H), 5.61 (d, 1H), 7.81 (d, 1H), 8.51 (broad s, 1H).

EXAMPLE 7

Preparation of (3S,3aR,4R,6R,8R,9R,10R,12R,15R,15aS)-15-Ethyloctahydro-8-methoxy-4,6,8,10,12,15a-hexamethyl-3-[[2-[5-methyl-2,4-1H,3H-pyrimidinedione-1-yl]ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-7, Compound of Formula I, Where R$^1$ is [2-[5-methyl-2,4-1H, 3H-pyrimidinedione-1-yl]ethyl]thio) p A] [[2-[5-Methyl-2,4-(1H,3H)-pyrimidinedione-1-yl]ethyl]thio]acetic acid methyl ester was synthesized from thymine and [[2-bromoethyl]thio]acetic acid methyl ester as described in example 6A. Mp: 75° C. (diisopropyl ether).

B] [[2-[5-Methyl-2,4-(1H,3H)-pyrimidinedione-1-yl]ethyl]thio]acetic acid:

Was obtained according to example 6B from [[2-[2,4-(1H,3H)-5-methyl-pyrimidinedione-1-yl]ethyl]thio]acetic acid methyl ester. Mp: 164° C. (ethanol). MS (EI): 244.1 (M$^+$). $^1$H-NMR (DMSO-d6): 1.75 (s, 3H), 2.83 (t, 2H), 3.33 (s, 2H), 3.82 (t, 2H), 7.53 (s, 1H), 11.25 (s, 1H), 12.64 (s, 1H).

C] (10E)-10,11-Didehydro-11-deoxy-6-O-methyl-erythromycin 2'-acetate 4"-(phenylmethyl carbonate)12-[[[2-[5-methyl-2,4-1H,3H-pyrimidinedione-1-yl]ethyl]thio]acetate]; (IV-7):

Compound IV-7 was synthesized from 500 mg 6 and 404 mg [[2-[5-methyl-2,4-(1H,3H)-pyrimidinedione-1-yl]ethyl]thio]acetic acid as described in example 6D. Yield: 334 mg (53%). R$_f$: 0.61 (CHCl$_3$/MeOH/NH$_4$OH 9:1:0.1). MS (ISP): 1132.3 (MH$^+$). $^1$H-NMR (CDCl$_3$) diagnostic signals only: 11.20 (s, 3H), 1.62 (s, 3H), 1.89 (s, 3H), 1.93 (s, 3H), 2.00 (s, 3H), 2.23 (s, 6H), 2.88 (t, 2H), 3.15 (s, 3H), 3.22 (s, 2H), 3.33 (s, 3H), 3.87 (t, 2H), 4.37 (m, 1H), 4.47 (d, 1H), 4.56 (d, 1H), 4.68 (dd, 1H), 4.98 (d, 1H), 5.13 (d, 1H), 5.26 (d, 1H), 5.73 (dd, 1H), 6.62 (s, 1H), 7.07 (s, 1H), 7.36 (s, 5H), 8.48 (broad s, 1H).

D] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-3-[[2-[5-methyl-2,4-1H,3H-pyrimidinedione-1-yl]ethyl]thio]-2H-furo[2,3-c]oxacyclotetradecin-2,5,13(3H,6H)-trione; (V-7):

Cyclization was done as described in example 1C using 180 mg IV-7 and 400 ml KO$^t$Bu in 6 ml DMF. Yield: 61 mg (30%). R$_f$: 0.69 (CHCl$_3$/MeOH/NH$_4$OH 9:1:0.1). $^1$H-NMR (CDCl$_3$) diagnostic signals only: 1.45 (s, 3H), 1.98 (s, 3H), 2.04 (s, 3H), 2.24 (s, 6H), 2.55 (s, 1H), 2.98 (s, 3H), 3.33 (s, 3H), 4.92 (d, 1H), 5.12 (d, 1H), 5.27 (d, 1H), 5.48 (dd, 1H), 7.35 (s, 5H), 7.66 (s, 1H), 8.31 (broad s, 1H).

E] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[[2-[5-methyl-2,4-1H,3H-pyrimidinedione-1-yl]ethyl]thio]-2H-furo[2,3-c]oxacyclotetradecin-2,5,13 (3H,6H)-trione; (VI-7):

61 mg V-7 were cleaved in 10 ml methanol containing 3% HCl according to example 1D to give 27 mg of VI-7. $R_f$: 0.21 (CHCl$_3$/MeOH/NH$_4$OH 9:1:0.1). MS (ISP): 840.1 (MH$^+$). $^1$H-NMR (CDCl$_3$) diagnostic signals only: 0.85 (t, 3H), 0.97 (d, 3H), 1.47 (s, 3H), 1.96 (s, 3H), 2.07 (s, 3H), 2.64 (s, 1H), 2.92 (s, 3H), 3.73 (d, 1H), 3.83 (m, 1H), 4.29 (dt, 1H), 4.50 (s, 1H), 4.63 (d, 1H), 4.77 (dd, 1H), 5.58 (dd, 1H), 7.64 (s, 1H), 8.60 (broad s, 1H).

F] (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-15-ethyloctahydro-8-methoxy-4,6,8,10,12,15a-hexamethyl-3-[[2-[5-methyl-2,4-1H,3H-pyrimidinedione-1-yl]ethyl]thio]-2H-furo[2,3-c]oxacyclotetradecin-2,5,11,13(3H,6H,12H)-tetrone; (VII-7):

In analogy to example 1E, oxidation of 27 mg VI-7 gave 27 mg (100%) of VII-7. $R_f$: 0.51 (CHCl$_3$/MeOH/NH$_4$OH 9:1:0.1). MS (ISP): 838.5 (MH$^+$). $^1$H-NMR (CDCl$_3$) diagnostic signals only: 0.88 (t, 3H), 1.28 (s, 3H), 1.53 (s, 3H), 1.96 (s, 3H), 2.04 (s, 3H), 2.25 (s, 6H), 2.60 (s, 1H), 2.67 (s, 3H), 4.42 (dt, 1H), 3.57 (m, 1H), 3.79 (m, 1H), 3.83 (q, 1H), 4.27 (d, 1H), 4.29 (m, 1H), 4.33 (s, 1H), 4.42 (d, 1H), 4.75 (dd, 1H), 5.51 (dd, 1H), 7.60 (s, 1H), 8.52 (broad s, 1H).

G] (3S,3aR,4R,6R,8R,9R,10R,12R,15R,15aS)-15-Ethyloctahydro-8-methoxy-4,6,8,10,12,15a-hexamethyl-3-[[2-[5-methyl-2,4-1H,3H-pyrimidinedione-1-yl]ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-7):

Deprotection of 28 mg VII-7 in 10 ml methanol gave 19.4 mg of I-7. $R_f$: 0.36 (acetone/NH$_4$OH 99:1). MS (ISP): 796.4 (MH$^+$). $^1$H-NMR (CDCl$_3$) diagnostic signals only: 0.86 (t, 3H), 0.15 (2 d, 6H), 1.53 (s, 3H), 1.96 (s, 3H), 2.31 (s, 6H), 2.59 (s, 1H), 2.68 (s, 3H), 3.21 (dd, 1H), 3.42 (dt, 1H), 3.58 (m, 1H), 3.79 (m, 1H), 3.86 (q, 1H), 4.20–4.38 (m, 4H), 5.49 (dd, 1H), 7.60 (s, 1H), 8.42 (broad s, 1H).

EXAMPLE 8

Preparation of (3S,3aR,4R,6R,8R,9R,10R,12R,15R,15aS)-15-Ethyloctahydro-8-methoxy-4,6,8,10,12,15a-hexamethyl-3-[[2-[quinoline-2-yl]ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-8, Compound of Formula I, Where R$^1$ is [2-(quinoline-2-yl)ethyl]thio)

A] [[2-(Quinoline-2-yl)ethyl]thio]acetic acid:

This compound was prepared in analogy to a procedure by Il'ichev et al., *J. Org. Chem. USSR* 1971, 7, 2511 from 2-vinylquinoline and thioglycolic acid. MS (ISP): 248.2 (MH$^+$).

B] (10E)-10,11-Didehydro-11-deoxy-6-O-methyl-erythromycin 2'-acetate 4"-(phenylmethyl carbonate)12-[[[2-(quinoline-2-yl)ethyl]thio]acetate] (IV-8):

According to example 1B, IV-8 was obtained from 400 mg 6 and 328 mg [[2-(quinoline-2-yl)-ethyl]thio]acetic acid. Yield: 477 mg. $R_f$: 0.61 (CH$_3$CN/CH$_2$Cl$_2$/NH$_4$OH 1:1:0.01). $^1$H-NMR (CDCl$_3$) diagnostic signals only: 1.88 (s, 3H), 2.00 (s, 3H), 2.23 (s, 6H), 3.16 (s, 3H), 3.32 (s, 3H), 4.37 (m, 1H), 4.46 (d, 1H), 4.56 (d, 1H), 4.69 (dd, 1H), 4.98 (d, 1H), 5.13 (d, 1H), 5.25 (d, 1H), 5.73 (dd, 1H), 6.62 (s, 1H), 7.30 (d, 1H), 7.35 (s, 5H), 7.50 (t, 1H), 7.69 (td, 1H), 7.80 (d, 1H), 8.03 (d, 1H), 8.11 (d, 1H).

C] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-3-[[2-(quinoline-2-yl)ethyl]thio]-2H-furo[2,3-c]oxacyclotetradecin-2,5,13(3H,6H)-trione; (V-8):

Cyclization was performed as described in example 1C with 477 mg IV-8 to give 104 mg of V-8. $R_f$: 0.66 (CH$_3$CN/CH$_2$Cl$_2$/NH$_4$OH 1:1:0.01).

D] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[[2-(quinoline-2-yl)ethyl]thio]-2H-furo[2,3-c]oxacyclotetradecin-2,5,13(3H,6H)-trione; (VI-8):

According to example 1D, 104 mg V-8 were cleaved in 15 ml methanol containing 3% HCl to give 67 mg (87%) of VI-8. $R_f$: 0.20 (ethyl acetate/methanol/NEt$_3$ 9:1:0.1). $^1$H-NMR (CDCl$_3$) diagnostic signals only: 2.07 (s, 3H), 2.26 (s, 6H), 2.69 (s, 1H), 2.92 (s, 3H), 3.73 (d, 1H), 4.61 (s, 1H), 4.64 (d, 1H), (s, 1H), 4.77 (dd, 1H), 5.59 (dd, 1H), 7.48 (t, 1H), 7.51 (d, 1H), 7.68 (td, 1H), 7.78 (d, 1H), 8.03 (d, 1H), 8.06 (d, 1H).

E] (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-15-ethyloctahydro-8-methoxy-4,6,8,10,12,15a-hexamethyl-3-[[2-[quinoline-2-yl]ethyl]thio]-2H-furo[2,3-c]oxacyclotetradecin-2,5,11,13(3H,6H,12H)-tetrone; (VII-8):

67 mg VI-8 were oxidized according to example 1E to give 65 mg of the desired ketolide VII-8. $R_f$: 0.27 (ethyl acetate/methanol/NEt$_3$ 9:1:0.1). MS (ISP): 841.3 (MH$^+$), 421.5 ([MH$_2$]$^{++}$).

F] (3S,3aR,4R,6R,8R,9R,10R,12R,15R,15aS)-15-Ethyloctahydro-8-methoxy-4,6,8,10,12,15a-hexamethyl-3-[[2-[quinoline-2-yl]ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-8):

Deprotection was done according to example 1F from 65 mg VII-8 to give 26 mg of the desired ketolide I-8. MS (ISP): 799.4 (MH$^+$), 400.8 ([MH$_2$]$^{++}$). $^1$H-NMR (CDCl$_3$) diagnostic signals only: 0.86 (t, 3H), 1.51 (s, 3H), 2.27 (s, 6H), 2.63 (s, 1H), 2.65 (s, 3H), 3.83 (q, 1H), 4.25 (d, 1H), 4.33 (d, 1H), 4.41 (s, 1H), 5.50 (dd, 1H), 7.46 (t, 1H), 7.49 (d, 1H), 7.68 (td, 1H), 7.77 (d, 1H), 8.03 (d, 1H), 8.05 (d, 1H).

EXAMPLE 9

Preparation of (3S,3aR,4R,6R,8R,9R,10R,12R,15R,15aS)-15-Ethyloctahydro-8-methoxy-4,6,8,10,12,15a-hexamethyl-3-[[3-(4-pyridinyl)propyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-9, Compound of Formula I, Where R$^1$ is [3-(4-pyridinyl)propyl]thio)

Synthesis of the side chain required for this macrolide (steps A to C) is shown in Scheme 4.

Scheme 4

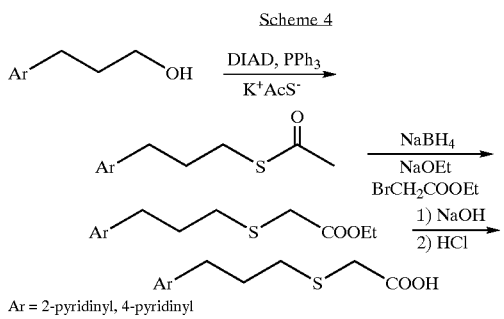

Ar = 2-pyridinyl, 4-pyridinyl

A] Ethanethioic acid, S-[3-(4-pyridinyl)propyl]ester:

Diisopropylazodicarboxylate (9.8 ml, 51 mmol) was added dropwise to a solution of 13.3 g (51 mmol) triphenylphosphine in 125 ml THF kept at 0° C. The mixture was stirred for 30 minutes and then a solution of 3.47 g (25 mmol) 4-pyridinepropanol and 3.6 ml (51 mmol) thioacetic acid in 50 ml THF was added. Stirring was continued for 12 hours and the mixture was allowed to warm to room temperature. The yellow solution is concentrated in vacuo and the residue is purified by flash chromatography (ethyl acetate/hexanes 1:1) to give 3.2 g (65%) of the desired product as yellow liquid. $R_f$: 0.20 (ethyl acetate/hexanes 1:1).

B] [3-[(4-Pyridinyl)propyl]thio]acetic acid ethyl ester:

Ethanethioic acid, S-[3-(4-pyridyl)-propyl]ester (3.2 g, 16.4 mmol) was dissolved in 50 ml ethanol and 620 mg (16.4 mmol) NaBH$_4$ was added in one portion. The mixture was stirred at room temperature overnight and then 377 mg (17.4 mmol) NaOEt and 1.81 ml (16.4 mmol) ethyl bromoacetate were added. Stirring was continued until TLC analysis showed the presence of a single product. Water was added and the mixture was extracted with ethyl acetate. The organic layer was washed with brine, dried (Na$_2$SO$_4$) and evaprated to give 3.4 g (87%) of a crude product that was used without further purification.

C] [[3-(4-Pyridinyl)propyl]thio]acetic acid 3.4 g (14.3 mmol) [[3-(4-pyridyl)propyl]thio]-acetic acid ethyl ester were dissolved in dioxane (40 ml) and 7.9 ml (15.05 mmol) of 2N NaOH were added. The mixture was stirred at room temperature for 12 hours and then neutralized with 7.9 ml (15.1 mmol) 2N HCl. Water was added and the aqueous phase was extracted continually with ethyl acetate to give after removal of the solvent 704 mg (23%) of the desired product as a white powder. MS (EI): 212.2 (MH$^+$).

D] (10E)-10,11-Didehydro-11-deoxy-6-O-methyl-erythromycin 2'-acetate 4"-(phenylmethyl carbonate)12-[[[3-(4-pyridinyl)propyl]thio]acetate]; (IV-9):

Coupling of 400 mg 6 and 210 mg [[3-(4-pyridinyl)propyl]thio]acetic acid gave 413 mg of the desired compound IV-9. $R_f$: 0.26 (CH$_3$CN/CH$_2$Cl$_2$/NH$_4$OH 1:1:0.1). $^1$H-NMR (CDCl$_3$) diagnostic signals only: 1.88 (s, 3H), 2.00 (s, 3H), 2.23 (s, 6H), 2.60 (t, 2H), 2.70 (t, 2H), 3.15 (s, 2H), 3.16 (s, 3H), 3.33 (s, 3H), 4.36 (m, 1H), 4.47 (d, 1H), 4.56 (d, 1H), 4.68 (dd, 1H), 4.98 (dd, 1H), 5.13 (d, 1H), 5.26 (d, 1H), 5.73 (dd, 1H), 6.62 (m, 2H), 7.36 (s, 5H), 8.51 (m, 2H).

E] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-3-[[3-(4-pyridinyl)propyl]thio]-2H-furo[2,3-c]oxacyclotetradecin-2,5,13(3H,6H)-trione; (V-9):

According to example 1C, cyclization of 413 mg IV-9 gave 88 mg of V-9 as a single diastereomer. $R_f$: 0.12 (CH$_3$CN/CH$_2$Cl$_2$/NH$_4$OH 1:1:0.1). MS (ISP): 1099.5 (MH$^+$), 550.6 ([MH$_2$]$^{++}$). $^1$H-NMR (CDCl$_3$) diagnostic signals only: 2.06 (s, 3H), 2.24 (s, 6H), 2.56 (s, 1H), 3.09 (s, 3H), 3.34 (s, 3H), 3.57 (d, 1H), 3.65 (m, 1H), 3.79 (d, 1H), 4.29 (m, 1H), 4.38 (s, 1H), 4.47 (d, 1H), 4.63 (d, 1H), 4.73 (dd, 1H), 4.95 (d, 1H), 5.12 (d, 1H), 5.26 (d, 1H), 5.48 (dd, 1H), 7.22 (m, 2H), 7.37 (s, 5H), 8.51 (m, 2H).

F] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[[3-(4-pyridinyl)propyl]thio]-2H-furo[2,3-c]oxacyclotetradecin-2,5,13(3H,6H)-trione; (VI-9):

According to example 1D, 200 mg V-9 were subjected to methanolysis to give 109 mg VI-9 as a single diastereomer. $R_f$: 0.43 (CHCl$_3$/MeOH/NH$_4$OH 9:1:0.1). MS (ISP): 807.4 (MH$^+$), 404.8 ([MH$_2$]$^{++}$). $^1$H-NMR (CDCl$_3$) diagnostic signals only: 0.86 (t, 3H), 0.98 (d, 3H), 1.10 (d, 3H), 1.12 (d, 3H), 1.23 (d, 3H), 1.26 (s, 3H), 1.27 (d, 3H), 1.46 (s, 3H), 2.09 (s, 3H), 2.26 (s, 6H), 2.67 (s, 1H), 3.03 (s, 3H), 3.49 (m, 2H), 3.74 (d, 1H), 4.48 (s, 1H), 4.65 (d, 1H), 4.77 (dd, 1H), 5.59 (dd, 1H), 7.21 (m, 2H), 8.49 (m, 2H).

G] (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-15-ethyloctahydro-8-methoxy-4,6,8,10,12,15a-hexamethyl-3-[[3-(4-pyridinyl)propyl]thio]-2H-furo[2,3-c]oxacyclotetradecin-2,5,11,13(3H,6H,12H)-tetrone; (VII-9):

100 mg VI-9 were oxidized according to example 1E to give 59 mg of the protected ketolide VII-9 as a single diastereomer. $R_f$: 0.60 (CHCl$_3$/MeOH/NH$_4$OH 9:1:0.1). MS (ISP): 805.4 (MH$^+$), 403.8 ([MH$_2$]$^{++}$). $^1$H-NMR (CDCl$_3$) diagnostic signals only: 0.89 (t, 3H), 1.12 (d, 3H), 1.17 (d, 3H), 1.19 (d, 3H), 1.29 (s, 3H), 1.39 (d, 3H), 1.51 (s, 3H), 2.07 (s, 3H), 2.25 (s, 6H), 2.61 (s, 1H), 2.78 (s, 3H), 3.56 (m, 1H), 3.85 (q, 1H), 4.24 (d, 1H), 4.28 (s, 1H), 4.40 (d, 1H), 4.75 (dd, 1H), 5.51 (dd, 1H), 7.20 (m, 2H), 8.50 (m, 2H).

H] (3S,3aR,4R,6R,8R,9R,10R,12R,15R,15aS)-15-Ethyloctahydro-8-methoxy-4,6,8,10,12,15a-hexamethyl-3-[[3-(4-pyridinyl)propyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-9):

In analogy to example 1F, 59 mg VII-9 were deprotected to give I-9 as a single diastereomer. $R_f$: 0.10 (CHCl$_3$/MeOH/NH$_4$OH 9:1:0.1). MS (ISP): 763.3 (MH$^+$), 382.3 ([MH$_2$]$^{++}$). $^1$H-NMR (CDCl$_3$) diagnostic signals only: 0.89 (t, 3H), 1.12 (d, 3H), 1.14 (d, 3H), 1.25 (d, 3H), 1.32 (s, 3H), 1.33 (d, 3H), 1.39 (d, 3H), 1.51 (s, 3H), 2.07 (m, 2H), 2.27 (s, 6H), 2.63 (s, 1H), 2.79 (s, 3H), 3.57 (m, 1H), 3.87 (q, 1H), 4.27 (s, 1H), 4.28 (d, 1H), 4.33 (d, 1H), 5.50 (dd, 1H), 7.18 (m, 2H), 8.49 (m, 2H).

EXAMPLE 10

Preparation of (3S,3aR,4R,6R,8R,9R,10R,12R,15R,15aS)-15-Ethyloctahydro-8-methoxy-4,6,8,10,12,15a-hexamethyl-3-[[3-(2-pyridinyl)propyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-10, Compound of Formula I, Where $R^1$ is [3-(2-pyridinyl)propyl]thio)

A] [[3-(2-Pyridinyl)propyl]thio]acetic acid was synthesized according to example 9 (steps A to C) from 2-pyridinepropanol. MS (EI): 212.2 (MH$^+$).

B] (10E)-10,11-Didehydro-11-deoxy-6-O-methyl-erythromycin 2'-acetate 4"-(phenylmethyl carbonate)12-[[[3-(2-pyridinyl)propyl]thio]acetate]; (IV-10):

In analogy to example 1B, coupling of 300 mg 6 and 210 mg [[3-(2-pyridinyl)propyl]thio]acetic acid gave 319 mg of the desired product IV-10. $R_f$: 0.35 (CH$_3$CN/CH$_2$Cl$_2$/NH$_4$OH 1:1:0.01). $^1$H-NMR (CDCl$_3$) diagnostic signals only: 1.58 (s, 3H), 1.86 (s, 3H), 2.00 (s, 3H), 2.03 (m, 2H), 2.23 (s, 6H), 2.63 (t, 2H), 2.87 (t, 2H), 3.16 (s, 5H), 3.32 (s, 3H), 4.38 (m, 1H), 4.46 (d, 1H), 4.57 (d, 1H), 4.68 (dd, 1H), 5.98 (d, 1H), 5.13 (d, 1H), 5.26 (d, 1H), 5.73 (dd, 1H), 6.62 (s, 1H), 7.07–7.19 (m, 2H), 7.35 (s, 5H), 7.60 (td, 1H), 8.52 (d, 1H).

C] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-3-[[3-(2-pyridinyl)propyl]thio]-2H-furo[2,3-c]oxacyclotetradecin-2,5,13 (3H,6H)-trione; (V-10)

In analogy to example 1C, 319 mg IV-10 were cyclized using 435 μl KO$^t$Bu to give 158 mg V-10 as a single diastereomer. $R_f$: 0.39 (CH$_3$CN/CH$_2$Cl$_2$/NH$_4$OH 1:1:0.01). $^1$H-NMR (CDCl$_3$) diagnostic signals only: 2.05 (s, 3H), 2.25 (s, 6H), 2.58 (s, 1H), 3.10 (s, 3H), 3.34 (s, 3H), 4.30 (m, 1H), 4.38 (s, 1H), 4.46 (d, 1H), 4.63 (d, 1H), 4.72 (dd, 1H), 4.96 (d, 1H), 5.13 (d, 1H), 5.27 (d, 1H), 5.52 (dd, 1H), 7.10 (m, 1H), 7.26 (m, 1H), 7.35 (s, 5H), 7.60 (td, 1H), 8.52 (d, 1H).

D] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[[3-(2-pyridinyl)propyl]thio]-2H-furo[2,3-c]oxacyclotetradecin-2,5,13(3H,6H)-trione; (VI-10)

In analogy to example 1D, 158 mg V-10 were subjected to methanolysis. 94 mg of VI-10 were obtained as a single diasteromer. $R_f$: 0.41 (CHCl$_3$/MeOH/NH$_4$OH 9:1:0.1). MS (ISP): 807.3 (MH$^+$), 404.8 ([MH2]$^{++}$). $^1$H-NMR (CDCl$_3$) diagnostic signals only: 0.86 (t, 3H), 0.98 (d, 3H), 1.09 (2 overlapping d, 6H), 1.49 (s, 3H), 2.07 (s, 3H), 2.26 (s, 6H), 2.69 (s, 1H), 3.05 (s, 3H), 3.77 (d, 1H), 4.47 (s, 1H), 4.66 (d, 1H), 4,77 (dd, 1H), 5.62 (dd, 1H), 7.10 (m, 1H), 7.26 (d, 1H), 7.60 (td, 1H), 8.52 (d, 1H).

E] (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-15-ethyloctahydro-8-methoxy-4,6,8,10,12,15a-hexamethyl-3-[[3-(2-pyridinyl)propyl]thio]-2H-furo[2,3-c]oxacyclotetradecin-2,5,11,13(3H,6H,12H)-tetrone; (VII-10):

94 mg VI-10 were oxidized according to example 1E to give 62 mg of VII-10. $R_f$: 0.59 (CHCl$_3$/MeOH/NH$_4$OH 9:1:0.1). MS (ISP): 803.2 (MH$^+$). $^1$H-NMR (CDCl$_3$) diagnostic signals only: 0.88 (t, 1H), 1.10 (d, 3H), 1.13 (d, 3H), 1.18 (d, 3H), 1.25 (d, 3H), 1.29 (s, 3H), 1.37 (d, 3H), 1.50 (s, 3H), 2.05 (s, 3H), 2.25 (s, 6H), 2.64 (s, 1H), 2.79 (s, 3H), 3.57 (m, 1H), 3.83 (q, 1H), 4.27 (d, 1H), 4.29 (s, 1H), 4.41 (d, 1H), 4.76 (dd, 1H), 5.53 (dd, 1H), 7.08 (m, 1H), 7.22 (d, 1H), 7.59 (td, 1H), 8.52 (d, 1H).

F] (3S,3aR,4R,6R,8R,9R,10R,12R,15R,15aS)-15-Ethyloctahydro-8-methoxy-4,6,8,10,12,15a-hexamethyl-3-[[3-(2-pyridinyl)propyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-10):

According to example 1F, 62 mg VII-10 were deprotected to give 52 mg of the desired ketolide I-10. $R_f$: 0.10 (CHCl$_3$/MeOH/NH$_4$OH 9:1:0.1). MS (ISP): 763.1 (MH$^+$), 382.6 ([MH$_2$]$^{++}$). $^1$H-NMR (CDCl$_3$) diagnostic signals only: 0.89 (t, 3H), 1.10 (d, 3H), 1.13 (d, 1H), 1.24 (d, 3H), 1.32 (s, 3H), 1.33 (d, 3H), 1.37 (d, 3H), 1.50 (s, 3H), 2.26 (s, 6H), 2.63 (s, 1H), 2.80 (s, 3H), 3.56 (m, 1H), 3.86 (q, 1H), 4.27 (s, 1H), 4.28 (d, 1H), 4.35 (d, 1H), 5.53 (dd, 1H), 7.09 (dd, 1H), 7.22 (d, 1H), 7.58 (td, 1H), 8.52 (d, 1H).

EXAMPLE 11

Preparation of (3S,3aR,4R,6R,8R,9R,10R,12R,15R,15aS)-15-Ethyloctahydro-8-methoxy-4,6,8,10,12,15a-hexamethyl-3-[[2-phenoxyethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-11, Compound of Formula I, Where $R^1$ is [2-phenoxyethyl]thio)

A] (10E)-10,11-Didehydro-11-deoxy-6-O-methyl-erythromycin 2'-acetate 4"-(phenylmethyl carbonate)12-[[[2-phenoxyethyl]thio]acetate]; (IV-11):

In analogy to example 1B, coupling of 300 mg 6 and 141 mg [[2-phenoxyethyl]thio]acetic acid gave 267 mg of IV-11. $R_f$: 0.75 (CH$_3$CN/CH$_2$Cl$_2$/NH$_4$OH 1:1:0.1). $^1$H-NMR (CDCl$_3$) diagnostic signals only: 1.89 (s, 3H), 2.00 (s, 3H), 2.23 (s, 6H), 2.99 (s, 2H), 3.16 (s, 3H), 3.31 (s, 2H), 3.34 (s, 3H), 4.18 (t, 2H), 4.36 (m, 1H), 4.46 (d, 1H), 4.57 (d, 1H), 4.88 (dd, 1H), 4.98 (d, 1H), 5.13 (d, 1H), 5.24 (d, 1H), 5.73 (dd, 1H), 6.62 (s, 1H), 6.89 (d, 2H), 6.97 (t, 1H), 7.31 (m, 2H), 7.36 (s, 5H).

B] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-3-[[2-phenoxyethyl]thio]-2H-furo[2,3-c]oxacyclotetradecin-2,5,13(3H,6H)-trione; (V-11):

According to example 1C, cyclization of 254 mg IV-11 with 342 μl KO$^t$Bu gave 25 mg of V-11 (product 1) and 99 mg of a product lacking the benzyloxycarbonyl protecting group at position 4" (product 2). $R_f$(product 1): 0.59 (CH$_3$CN/CH$_2$Cl$_2$/NH$_4$OH 1:1:0.1). $R_f$ (product 2): 0.19 (CH$_3$CN/CH$_2$Cl$_2$/NH$_4$OH 1:1:0.1).

C] (3R or S,3aR,4R or S,6R,8R,9R,10S,11S,12R,15R,15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[[2-phenoxyethyl]thio]-2H-furo[2,3-c]oxacyclotetradecin-2,5,13(3H,6H)-trione; mixture of 2 diastereomers (VI-11):

88 mg V-11 were subjected to methanolysis to give 34 mg of the desired product VI-11 as a 2:1 mixture of two diastereomers. $R_f$: 0.30 ($CH_3CN/CH_2Cl_2/NH_4OH$ 1:1:0.1). $^1H$-NMR ($CDCl_3$) diagnostic signals only: Diasteromer 1; 1.45 (s, 3H), 2.07 (s, 3H), 2.25 (s, 6H), 3.00 (s, 3H), 3.73 (s, 1H), 5.55 (dd, 1H); diasteromer 2; 1.50 (s, 3H), 2.01 (s, 3H), 2.27 (s, 6H), 3.06 (s, 3H), 3.82 (d, 1H), 5.03 (dd, 1H).

D] (3R or S,3aR,4R or S,6R,8R,9R,10R,12R,15R,15aS)-9-[[2-O-Acetyl-3,4,6-trideoxy-3-(dimethylamino)-β-D-xylo-hexopyranosyl]oxy]-15-ethyloctahydro-8-methoxy-4,6,8,10,12,15a-hexamethyl-3-[[2-phenoxyethyl]thio]-2H-furo[2,3-c]oxacyclotetradecin-2,5,11,13(3H,6H,12H)-tetrone; mixture of two diastereomers (VII-11):

65 mg VI-11 were oxidized in analogy to example 1E to give 60 mg of the protected ketolide VII-11 as a 2:1 mixture of two diastereomers. $R_f$: 0.32 ($CH_3CN/CH_2Cl_2/NH_4OH$ 1:1:0.1). $^1H$-NMR ($CDCl_3$) diagnostic signals only: Diasteromer 1; 1.50 (s, 3H), 2.04 (s, 3H), 2.24 (s, 6H), 2.67 (s, 1H), 2.74 (s, 3H), 3.83 (q, 1H), 4.34 (s, 1H), 5.47 (dd, 1H); diasteromer 2; 1.56 (s, 3H), 2.03 (s, 3H), 2.23 (s, 6H), 2.84 (s, 3H), 3.77 (q, 1H), 4.99 (dd, 1H).

E] (3S,3aR,4R,6R,8R,9R,10R,12R,15R,15aS)-15-Ethyloctahydro-8-methoxy-4,6,8,10,12,15a-hexamethyl-3-[[2-phenoxyethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-11):

According to example 1F, 60 mg VII-11 were deprotected to give 24 mg I-11 as a single diastereomer. MS (ISP): 764.3 (MH+). 0.88 (t, 3H), 1.10 (d, 3H), 1.13 (d, 3H), 1.23–1.40 (3 d, 1 s), 1.51 (s, 3H), 2.26 (s, 6H), 2.67 (s, 1H), 2.75 (s, 3H), 3.58 (m, 1H), 3.87 (q, 1H), 4.23–4.38 (m, 5H), 5.47 (dd, 1H), 6.89–7.00 (m, 3H), 7.21–7.32 (m, 2H).

EXAMPLE 12

Preparation of 3S,3aR,4R,6R,8R,9R,10R,12R,15R,15aS)-15-Ethyloctahydro-8-methoxy-4,6,8,10,12,15a-hexamethyl-3-[[3,4-dimethoxyphenyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-12, Compound of Formula I, Where $R^1$ is [3,4-dimethoxyphenyl]thio)

A] (10E)-10,11-Didehydro-11-deoxy-6-O-methyl-erythromycin 2'-acetate 4"-(phenylmethyl carbonate)12-[[[3,4-dimethoxyphenyl]thio]acetate]; (IV-12):

In analogy to example 1B, coupling of 300 mg 6 and 151 mg [[3,4-dimethoxyphenyl]thio]acetic acid gave 254 mg of IV-12. $R_f$: 0.57 ($CH_3CN/CH_2Cl_2/NH_4OH$ 1:1:0.01). $^1H$-NMR ($CDCl_3$) diagnostic signals only: 1.83 (s, 3H), 2.00 (s, 3H), 2.23 (s, 6H), 3.13 (s, 3H), 3.32 (s, 3H), 3.51 (s, 2H), 3.87 (s, 6H), 4.35 (m, 1H), 4.44 (d, 1H), 4.56 (d, 1H), 4.68 (dd, 1H), 4.97 (d, 1H), 5.13 (d, 1H), 5.24 (d, 1H), 5.67 (dd, 1H), 6.59 (s, 1H), 6.79 (d, 1H), 7.00 (m, 2H).

B] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-3-[[3,4-dimethoxyphenyl]thio]-2H-furo[2,3-c]oxacyclotetradecin-2,5,13(3H,6H)-trione; (V-12):

Cyclization of 254 mg IV-12 with KO$^t$Bu according to example 1C gave 25 mg of V-12 (product1) along with 99 mg of a product lacking the benzyloxycarbonyl protecting group at position 4" (product 2). $R_f$(product 1): 0.52 ($CH_3CN/CH_2Cl_2/NH_4OH$ 1:1:0.01). $R_f$(product 2): 0.08 ($CH_3CN/CH_2Cl_2/NH_4OH$ 1:1:0.01).

C] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[[3,4-dimethoxyphenyl]thio]-2H-furo[2,3-c]oxacyclotetradecin-2,5,13(3H,6H)-trione; (VI-12):

The compound lacking the benzyloxycarbonyl protecting group obtained in step 12B (99 mg) was subjected to methanolysis as described in example 1D to give 50 mg of the desired product VI-12. $R_f$: 0.27 ($CH_3CN/CH_2Cl_2/NH_4OH$ 1:1:0.01). $^1H$-NMR ($CDCl_3$) diagnostic signals only: 0.91 (t, 3H), 0.99 (d, 1H), 1.05 (d, 3H), 1.11 (d, 3H), 1.24 (d, 3H), 1.27 (d, 3H), 1.30 (s, 3H), 1.46 (s, 3H), 2.08 (s, 3H), 2.27 (s, 6H), 2.88 (s, 1H), 3.13 (s, 3H), 3.78 (d, 1H), 3.88 (s, 3H), 3.94 (s, 3H), 4.65 (d, 1H), 4.72 (s, 1H), 4.79 (dd, 1H), 5.44 (dd, 1H), 6.84 (d, 1H), 7.30 (d, 1H), 7.32 (s, 1H).

D] (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-15-ethyloctahydro-8-methoxy-4,6,8,10,12,15a-hexamethyl-3-[[3,4-dimethoxyphenyl]thio]-2H-furo[2,3-c]oxacyclotetradecin-2,5,11,13(3H,6H,12H)-tetrone; (VII-12):

Oxidation was done according to example 1E with 50 mg VI-12 to give 42 mg of the desired product VII-12. $R_f$: 0.31 ($CH_3CN/CH_2Cl_2/NH_4OH$ 1:1:0.01). $^1H$-NMR ($CDCl_3$) diagnostic signals only: 0.99 (t, 3H), 1.06 (d, 3H), 1.14 (d, 3H), 1.20 (d, 3H), 1.26 (d, 3H), 1.33 (s, 3H), 1.39 (d, 3H), 1.51 (s, 3H), 2.05 (s, 3H), 2.25 (s, 6H), 2.82 (s, 1H), 2.887 (s, 3H), 3.58 (m, 1H), 3.86 (q, 1H), 3.87 (s, 3H), 3.94 (s, 3H), 4.28 (d, 1H), 4.42 (d, 1H), 4.51 (s, 1H), 4.76 (dd, 1H), 5.37 (dd, 1H), 6.83 (d, 1H), 7.26 (d, 1H), 7.29 (s, 1H).

E] 3S,3aR,4R,6R,8R,9R,10R,12R,15R,15aS)-15-Ethyloctahydro-8-methoxy-4,6,8,10,12,15a-hexamethyl-3-[[3,4-dimethoxyphenyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-12):

Final deprotection was done with 22 mg VII-12 to give 20 mg I-12. $R_f$: 0.06 ($CH_3CN/CH_2Cl_2/NH_4OH$ 1:1:0.01). MS (ISP): 780.5 (MH+). $^1H$-NMR ($CDCl_3$) diagnostic signals only: 0.93 (t, 3H), 1.07 (d, 3H), 1.13 (d, 3H), 1.27 (d, 3H), 1.34 (d, 3H), 1.36 (s, 3H), 1.40 (d, 3H), 1.51 (s, 3H), 2.27 (s, 6H), 2.82 (s, 1H), 2.88 (s, 3H), 3.58 (m, 1H), 3.87 (s, 3H), 3.88 (q, 1H), 3.93 (s, 3H), 4.31 (d, 1H), 4.35 (d, 1H), 4.51(s, 1H), 5.36 (dd, 1H), 6.84 (d, 1H), 7.28 (d, 1H), 7.30 (s, 1H).

EXAMPLE 13

Preparation of (3S,3aR,4R,6R,8R,9R,10R,12R,15R,15aS)-15-Ethyloctahydro-8-methoxy-4,6,8,10,12,15a-hexamethyl-3-[[2-(2-pyridinyl)ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-13, Compound of Formula I, Where $R^1$ is [[2-(2-pyridinyl)ethyl]thio)

A] [[2-(2-pyridinyl)ethyl]thio]acetic acid was prepared from 2-vinylpyridine and thioglycolic acid according to Il'ichev et al. *J. Org. Chem USSR* 1971, 7, 2511.

B] (10E)-10,11-Didehydro-11-deoxy-6-O-methyl-erythromycin 2'-acetate 4"-(phenylmethyl carbonate)12-[[[2-(2-pyridinyl)ethyl]thio]acetate]; (IV-13):

In analogy to example 1B, 318 mg of IV-13 were obtained from 300 mg 6 and 200 mg [[2-(2-pyridinyl)ethyl]thio] acetic acid. $R_f$: 0.65 (CH$_3$CN/CH$_2$Cl$_2$/NH$_4$OH 1:1:0.01). $^1$H-NMR (CDCl$_3$) diagnostic signals only: 1.20 (s, 3H), 1.60 (s, 3H), 1.87 (s, 3H), 2.00 (s, 3H), 2.23 (s, 6H), 3.05 (m, 4H), 3.16 (s, 3H), 3.17 (s, 2H), 3.32 (s, 3H), 5.73 (dd, 1H), 6.63 (s, 1H), 7.14 (m, 2H), 7.35 (s, 5H), 7.60 (td, 1H), 8.53 (d, 1H).

C] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-3-[[2-(2-pyridinyl)ethyl]thio]-2H-furo[2,3-c]oxacyclotetradecin-2,5,13(3H,6H)-trione; (V-13):

In analogy to example 1C, 113 mg IV-13 was treated with 156 µl KO$^t$Bu in 3 ml DMF, resulting in 69 mg V-13. $R_f$: 0.65 (CH$_3$CN/CH$_2$Cl$_2$/NH$_4$OH 1:1:0.01). $^1$H-NMR (CDCl$_3$) diagnostic signals only: 0.85 (t, 3H), 1.93 (d, 1H), 1.32 (s, 3H), 1.42 (s, 3H), 2.04 (s, 3H), 2.24 (s, 6H), 2.57 (s, 1H), 2.99 (s, 3H), 3.33 (s, 3H), 4.29 (m, 1H), 4.45 (s, 1H), 4.45, (d, 1H), 4.62 (d, 1H), 4.72 (dd ,1H), 4.93 (d, 1H), 5.12 (d, 1H), 5.24 (d, 1H), 5.48 (dd, 1H), 7.08 (dd, 1H), 7.36 (m, 6H), 7.58 (td, 1H), 8.25 (d, 1H).

D] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[[2-(2-pyridinyl)ethyl]thio]-2H-furo[2,3-c]oxacyclotetradecin-2,5,13(3H,6H)-trione; (IV-13)

In analogy to example 1D, 69 mg V-13 were treated with 10 ml methanol containing 3% HCl. Yield: 53 mg. $R_f$: 0.38 (ethyl acetate/methanol/NEt$_3$ 8:2:0.1). $^1$H-NMR (CDCl$_3$) diagnostic signals only: 0.84 (t, 3H), 0.97 (d, 1H), 1.27 (s, 3H), 1.45 (s, 3H), 2.10 (s, 3H), 2.32 (s, 6H), 2.67 (s, 1H), 2.93 (s, 3H), 3.73 (d, 1H), 4.55 (s, 1H), 4.66 (d, 1H), 4.78 (dd, 1H), 5.58 (dd, 1H), 7.08 (dd, 1H), 7.37 (d, 1H), 7.58 (td, 1H), 8.52 (d, 1H).

E] (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-15-ethyloctahydro-8-methoxy-4,6,8,10,12,15a-hexamethyl-3-[[2-(2-pyridinyl)ethyl]thio]-2H-furo[2,3-c]oxacyclotetradecin-2,5,11,13(3H,6H,12H)-tetrone; (VII-13):

44 mg VI-13 were oxidized according to example 1E to give 38 mg of the protected ketolide VII-13. $R_f$: 0.50 (CH$_3$CN/CH$_2$Cl$_2$/NH$_4$OH 1:1:0.01). $^1$H-NMR (CDCl$_3$) diagnostic signals only: 0.87 (t, 3H), 1.25 (s, 3H), 1.50 (s, 3H), 2.04 (s, 3H), 2.25 (s, 6H), 2.62 (s, 1H), 3.57 (m, 1H), 3.82 (q, 1H), 4.24 (d, 1H), 4.38 (s, 1H), 4.41 (d, 1H), 4.47 (dd, 1H), 5.50 (dd, 1H), 7.08 (dd, 1H), 7.34 (d, 1H), 7.57 (td, 1H), 8.52 (d, 1H).

F] (3S,3aR,4R,6R,8R,9R,10R,12R,15R,15aS)-15-Ethyloctahydro-8-methoxy-4,6,8,10,12,15a-hexamethyl-3-[[2-(2-pyridinyl)ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-13):

Deprotection of 44 mg VII-13 was done according to example 1F to give 38 mg I-13. MS (ISP): 749.5 (MH$^+$), 375.7 ([MH$_2$]$^{++}$). $^1$H-NMR (CDCl$_3$) diagnostic signals only: 0.87 (t, 3H), 1.13 (2 d, 6H), 1.25 (d, 3H), 1.31 (s, 3H), 1.32 (d, 3H), 1.35 (d, 3H), 1.50 (s, 3H), 2.27 (s, 6H), 2.62 (s, 1H), 2.67 (s, 3H), 3.57 (m, 1H), 3.84 (q, 1H), 4.27 (d, 1H), 3.33 (d, 1H), 4.35 (s, 1H), 5.48 (dd, 1H), 7.08 (dd, 1H), 7.35 (d, 1H), 7.57 (td, 1H), 8.52 (d, 1H).

EXAMPLE 14

Preparation of (3S,3aR,4R,6R,8R,9R,10R,12R,15R,15aS)-3-[[2-[6-Amino-9H-purine-9-yl]ethyl]thio]-15-ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-14, Compound of Formula I, Where R$^1$ is [2-[6-amino-9H-purine-9-yl]ethyl]thio)

A] (10E)-10,11-Didehydro-11-deoxy-6-O-methyl-erythromycin 2'-acetate 12-[chloroacetate]4"-(phenylmethyl carbonate) (Scheme 2, formula IX-1):

This compound was obtained according to example 1B from 6 (6 g) and chloroacetic acid (1.88 g). Yield: 6.1 g. $R_f$: 0.61 (CH$_2$Cl$_2$/MeOH/NH$_4$OH 100:10:1). MS (ISP): 982.4 (MH$^+$).

The side chain required for the synthesis of this macrolide was made as outlined in Scheme 5 (steps 14B to 14E).

Scheme 5:

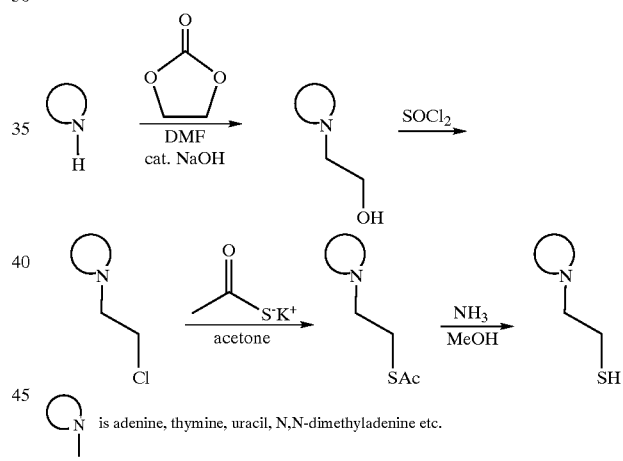

B] 9-(2-Hydroxyethyl)-6-amino-9H-purine:

Adenine (2.7 g, 20 mmol) was suspended in DMF (100 ml) and 1.76 g (20 mmol) ethylene carbonate was added. After addition of a catalytic amount of NaOH (15 mg), the mixture was stirred at 160° C. for 2 hours. DMF was removed in vacuo and the residue was crystallized from EtOH (350 ml) to give 2.1 g (59%) of a brownish solid. MS (EI): 179.1 (M$^+$). $^1$H-NMR (DMSO-d6): 3.74 (q, 2H), 4.18 (t, 2H), 4.99 (t, 1H), 7.16 (broad s, 2H), 8.07 (s, 1H), 8.13 (s, 1H).

C] 9-(2-Chloroethyl)-6-amino-9H-purine:

1.97 g (11 mmol) 9-(hydroxyethyl)-6-amino-9H-purine were suspended in 20 ml thionyl chloride and heated at 70° C. for 45 minutes. Excess thionyl chloride was removed in vacuo and the residue was dissolved in water (100 ml). The aqueous solution was basified with NaHCO$_3$ solution (10%) and the resulting slurry was stirred for 15 minutes. The product was isolated by filtration, washed with water and dried to give 1.25 g of a brownish solid. The crystallization step was repeated to give another 220 mg of product. Total yield: 1.47 g (68%). MS (EI): 197.1 ($M^+$). $^1$H-NMR (DMSO-d6): 4.07 (t, 2H), 4.50 (t, 2H), 7.23 (broad s, 2H), 8.15 (s, 1H), 8.17 (s, 1H).

D] Ethanethioic acid, S-[[6-amino-9H-purine-9-yl]ethyl] ester:

1.2 g (6.07 mmol) 9-(chloroethyl)-6-amino-9H-purine was suspended in acetone (30 ml). After addition of solid potassium thioacetate (870 mg (7.6 mmol)), the mixture was heated to reflux for 12 hours. The suspension was concentrated in vacuo, suspended in $CH_2Cl_2$ and chromatographed on 120 g of silica gel, eluting with a gradient of 0 to 9% methanol in $CH_2Cl_2$. The appropriate fractions were combined and evaporated to give 1.4 g (97%) of a brownish solid. MS (EI): 237.1 ($M^+$). $^1$H-NMR (DMSO-d6): 2.30 (s, 3H), 3.40 (t, 2H), 4.32 (t, 2H), 7.20 (broad s, 2H), 8.11 (s, 1H), 8.14 (s, 1H).

E] [6-amino-9H-purine]-1-ethanethiol:

1.3 g (5.5 mmol) ethanethioic acid, S-[[6-amino-9H-purine-9-yl]ethyl]ester was suspended in 50 ml degassed methanol, kept under argon. Ammonia was bubbled through the solution for 5 minutes and the internal temperature rose to 40° C. The resulting solution was stirred for 60 minutes to give a suspension. This was filtered and the filtrate was concentrated and the fluffy solid was dried at 60° C. in vacuo. Yield: 850 mg (79%). MS (EI): 195.1 ($M^+$). $^1$H-NMR (DMSO-d6): 2.50 (1H, covered by DMSO), 2.96 (broad q, 2H), 4.30 (t, 2H), 7.20 (broad s, 2H), 8.14 (s, 2H). The product was contaminated with approx. 5% of the corresponding disulfide.

F] (10E)-10,11-didehydro-11-deoxy-6-O-methyl-erythromycin 2'-acetate 12-[[[2-[6-amino-9H-purine-9-yl]ethyl]thio]acetate]4"-(phenylmethyl carbonate); (IV-14):

To a solution of 214 mg (218 μmol) IX-1 dissolved in 8 ml acetone were added 36 μl DBU and a catalytic amount of NaI. [6-amino-9H-purine]-1-ethanethiol (45 mg, 230 μmol) was added in one portion and the resulting suspension was stirred at room temperature. The mixture gradually cleared to give a hazy solution. The reaction mixture was diluted with $CH_2Cl_2$, extracted with 5% aqueous $NaHCO_3$, dried over $Na_2SO_4$ and evaporated. The crude product was purified by flash chromatography on silica gel (ethyl acetate/methanol/$NEt_3$ 9:1:0.1) to give 193 mg of the desired product IV-14 as a glass. $R_f$: 0.37 ($CHCl_3$/MeOH/$NH_4OH$ 9:1:0.1). MS (ISP): 1141.5 ($MH^+$), 571.3 ($[MH_2]^{++}$). $^1$H-NMR ($CDCl_3$) diagnostic signals only: 0.87 (t, 3H), 1.61 (s, 3H), 1.87 (s, 3H), 2.00 (s, 3H), 2.23 (s, 6H), 3.09 (t, 2H), 3.15 (s, 3H), 3.16 (s, 2H), 3.32 (s, 3H), 4.38 (m, 1H), 4.40 (t, 2H), 4.45 (d, 1H), 4.56 (d, 1H), 4.68 (dd, 1H), 4.97 (d, 1H), 5.14 (d, 1H), 5.24 (d, 1H), 5.51, (s, 2H), 5.71 (dd, 1H), 6.60 (s, 1H), 7.36 (s, 5H), 7.86 (s, 1H), 8.35 (s, 1H).

G] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-3-[[2-[6-amino-9H-purine-9-yl]ethyl]thio]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-2H-furo[2,3-c]oxacyclotetradecin-2,5,13(3H,6H)-trione; (V-14):

Cyclization of 175 mg IV-14 was done according to example 6E with 17 mg NaH in 4.5 ml DMF to give a crude product, that was identified as a mixture of the desired compound V-14 and a DMF condensation product thereof. Compound 1: MS (ISP): 1141.4 ($MH^+$), 571.8 ($[MH_2]^{++}$). Compound 2: 1196.2 (($MH+DMF-H_2O)^+$, 599.1 ($[MH_2+DMF-H_2O]^{++}$).

H] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-3-[[2-[6-amino-9H-purine-9-yl]ethyl]thio]-15-ethyldecahydro-11-hydroxy-8-methoxy-4,6,8,10,12,15a-hexamethyl-2H-furo[2,3-c]oxacyclotetradecin-2,5,13(3H,6H)-trione; (VI-14):

The mixture containing V-14 obtained in step 14F was subjected to methanolysis (20 ml methanol containing 3% HCl) as described in example 1D to give VI-14. Yield: 79 mg. $R_f$: 0.36 ($CHCl_3$/MeOH/$NH_4OH$ 9:1:0.1). MS (ISP): 849.3 ($MH^+$), 425.7 ($[MH_2]^{++}$). $^1$H-NMR ($CDCl_3$) diagnostic signals only: 0.81 (t, 3H), 0.99 (d, 3H), 1.34 (s, 3H), 1.47 (s, 3H), 2.08 (s, 3H), 2.27 (s, 6H), 2.63 (s, 1H), 3.79 (d, 1H), 4.45–4.85 (m, 5H), 5.46 (dd, 1H), 5.75 (s, 2H), 8.23 (s, 1H), 8.32 (s, 1H).

I] (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-3-[[2-[6-amino-9H-purine-9-yl]ethyl]thio]-15-ethyloctahydro-8-methoxy-4,6,8,10,12,15a-hexamethyl-2H-furo[2,3-c]oxacyclotetradecin-2,5,11,13(3H,6H,12H)-tetrone; S,S-dimethylsulfilimine derivative, (VII-14):

Oxidation was performed as described in example 1E. From 70 mg VI-14, 52 mg of VII-14 were obtained as a S,S-dimethylsulfilimine derivative. $R_f$: 0.44 ($CHCl_3$/MeOH/$NH_4OH$).

K] (3S,3aR,4R,6R,8R,9R,10R,12R,15R,15aS)-3-[[2-[6-Amino-9H-purine-9-yl]ethyl]thio]-15-ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-14):

52 mg VII-14 was deprotected as described in example 1F. Yield 39 mg. $R_f$: 0.4 ($CHCl_3$/MeOH/$NH_4OH$). MS (ISP): 805.5 ($MH^+$), 403.7 ($[MH_2]^{++}$). $^1$H-NMR ($CDCl_3$) diagnostic signals only: 0.86 (t, 3H), 1.16 (d, 3H), 1.17 (d, 3H), 1.26 (d, 3H), 1.32 (d, 3H), 1.33 (d, 3H), 1.38 (s, 3H), 1.53 (s, 3H), 2.27 (s, 6H), 2.45 (m, 1H), 2.62 (s, 1H), 2.70 (s, 3H), 3.05–3.21 (m, 4H), 3.50 (broad s, 1H), 3.51–3.12 (m, 2H), 3.84 (q, 1H), 4.29 (d, 1H), 4.34 (d, 1H), 4.39 (s, 1H), 4.51 (m, 1H), 4.19 (dt, 1H), 5.38 (dd, 1H), 5.48 (s, 2H), 8.22 (s, 1H), 8.34 (s, 1H).

EXAMPLE 15

Preparation of (3S,3aR,4R,6R,8R,9R,10R,12R,15R,15aS)-3-[[2-[4-Amino-2-1H-pyrimidinone-1-yl]ethyl]thio]-15-ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-15, Compound of Formula I, Where $R^1$ is [[4-amino-2-1H-pyrimidinone-1-yl]ethyl]thio)

A] 1-(2-Hydroxyethyl)-4-amino-2-1H-pyrimidinone was obtained according to example 14B from cytosine. MS (EI): 155.1 ($M^+$). $^1$H-NMR (DMSO-d6): 3.54 (q, 2H), 3.67 (t, 2H), 4.81 (t, 1H), 5.60 (d, 1H), 6.94 (broad s, 2H), 7.47 (d, 1H).

B] 1-(2-Chloroethyl)-4-amino-2-1H-pyrimidinone was prepared according to example 14C from 3.8 g 1-(2-hydroxyethyl)-4-amino-2-1H-pyrimidinone and 60 ml thionyl chloride. 3.2 g (97%) of crude product were obtained and used without further purification. Recrystallization was omitted in this case due to decomposition. $R_f$: 0.51 (ethyl acetate/acetone/acetic acid/$H_2O$ 6:2:1:1).

C] Ethanethioic acid, S-[[4-amino-2-1H-pyrimidinone-1-yl]ethyl]ester was obtained according to example 14D from 1.73 g (10 mmol) crude 1-(2-chloroethyl)-4-amino-2-1H-pyrimidinone and 1.43 g (12.5 mmol) potassium thioacetate to give 1.36 g (64%) of the desired product. MS (EI): 213.1 ($M^+$). $^1$H-NMR (DMSO-d6): 2.33 (s, 3H), 3.11 (t, 2H), 3.76 (t, 2H), 5.61 (d, 1H), 6.97 (broad s, 1H), 7.04 (broad s, 1H), 7.50 (d, 1H).

D] [4-Amino-2-1H-pyrimidinone]-1-ethanethiol:

Following example 14E, 1.28 g ethanethioic acid, S-[4-amino-2-1H-pyrimidinone-1-yl]ethyl ester were treated with $NH_3$ to give 550 mg (53%) of the desired product. MS (EI): 171.1 ($M^+$). $^1$H-NMR (DMSO-d6): 2.38 (t, 1H), 2.71 (q, 2H), 3.75 (t, 2H), 5.62 (d, 1H), 6.97 (broad s, 1H), 7.03 (broad s, 1H), 7.56 (d, 1H).

E] (10E)-10,11-Didehydro-11-deoxy-6-O-methyl-erythromycin 2'-acetate 12-[[[2-[4-amino-2-1H-pyrimidinone-1-yl]ethyl]thio]acetate] 4"-(phenylmethyl carbonate); (IV-15):

According to example 14F, 300 mg IV-15 were obtained from 300 mg IX-1 and 56 mg [4-amino-2-(1H)-pyrimidinone]-1-ethanethiol. MS (ISP): 1117.5 ($MH^+$), 559.4 ($[MH_2]^{++}$). $^1$H-NMR (CDCl$_3$) diagnostic signals only: 1.61 (s, 3H), 1.87 (s, 3H), 2.01 (s, 3H), 2.27 (s, 6H), 2.96 (t, 2H), 3.16 (s, 3H), 3.21 (s, 2H), 3.33 (s, 3H), 3.96 (t, 2H), 4.37 (m, 1H), 4.47 (d, 1H), 4.57 (d, 1H), 4.69 (dd, 1H), 4.98 (d, 1H), 5.13 (d, 1H), 5.26 (d, 1H), 5.72 (dd, 1H), 5.83 (d, 1H), 6.61 (s, 1H), 7.36 (m, 6H).

F] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-3-[[2-[4-amino-2-1H-pyrimidinone-1-yl]ethyl]thio]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-2H-furo[2,3-c]oxacyclotetradecin-2,5,13 (3H, 6H)-trione; (V-15):

According to example 1C, 300 mg IV-15 were cyclized using 670 μl KO$^t$Bu to give 109 mg of crude product that was shown to be a mixture of V-15 and a DMF condensation product thereof. Product 1: MS (ISP): 1117.5 ($MH^+$), 559.9 ($[MH_2]^{++}$); product 2: MS (ISP): 587.4 ($[MH_2]^{++}$).

G] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-3-[[2-[4-amino-2-1H-pyrimidinone-1-yl]ethyl]thio]-15-ethyldecahydro-11-hydroxy-8-methoxy-4,6,8,10,12,15a-hexamethyl-2H-furo[2,3-c]oxacyclotetradecin-2,5,13(3H,6H)-trione; (VI-15):

The crude product from step 15F was subjected to methanolysis as described in example 1D to give 49 mg of VI-15. $^1$H-NMR (CDCl$_3$) diagnostic signals only: 2.01 (s, 3H), 2.26 (s, 6H), 2.66 (s, 1H), 2.97 (s, 3H), 3.78 (d, 1H), 4.44 (s, 1H), 5.51 (dd, 1H), 5.60 (d, 1H), 6.00 (broad s), 7.77 (d, 1H).

H] (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-3-[[2-[4-amino-2-1H-pyrimidinone-1-yl]ethyl]thio]-15-ethyloctahydro-8-methoxy-4,6,8,10,12,15a-hexamethyl-2H-furo[2,3-c]oxacyclotetradecin-2,5,11,13(3H,6H,12H)-tetrone; (VII-15):

In analogy to example 1E, 49 mg VI-15 were oxidized to give 36 mg of a mixture of VII-15 and its S,S-dimethylsulfilimine derivative. MS (ISP): 823.4 ($MH^+$), 412.3 ($[MH_2]^{++}$).

I] (3S,3aR,4R,6R,8R,9R,10R,12R,15R,15aS)-3-[[2-[4-Amino-2-1H-pyrimidinone-1-yl]ethyl]thio]-15-ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-15):

In analogy to example 1F, 39 mg VII-15 were deprotected to give 29 mg of the desired compound. MS (ISP): 781.4 ($MH^+$), 391.6 ($[MH_2]^{++}$). $^1$H-NMR (CDCl$_3$) diagnostic signals only: 0.87 (t, 3H), 1.14 (2d, 6H), 1.26 (d, 3H), 1.52 (s, 3H), 2.26 (s, 6H), 2.61 (s, 1H), 2.70 (s, 3H), 3.87 (q, 1H), 3.90 (m, 2H), 4.22–4.42 (m, 5H), 5.41 (dd, 1H), 5.51 (broad s, 2H), 5.57 (d, 1H), 7.82 (d, 1H).

EXAMPLE 16

Preparation of (3S,3aR,4R,6R,8R,9R,10R,12R,15R,15aS)-15-Ethyloctahydro-8-methoxy-4,6,8,10,12,15a-hexamethyl-3-[[2-[3-(3-pyridinyl)-1H-pyrazol-1-yl]-ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-16, Compound of Formula I, Where $R^1$ is [2-[3-(3-pyridinyl)-1H-pyrazol-1-yl]ethyl]thio)

A] 3-(3-Pyridinyl)-1H-pyrazole was prepared according to *Schunack Arch. Pharmaz.* 1973, 306, 934.

B] 1-(2-Hydroxyethyl)-3-(3-pyridinyl)-1H-pyrazole was obtained according to example 14B from 1.84 g (12.7 mmol) 3-(3-pyridinyl)-1H-pyrazole and 1.11 g ethylene carbonate. 1.65 g (69%) of the desired product was obtained as a colorless solid. MS (EI): 189.1 ($M^+$). $^1$H-NMR (DMSO-d6): 3.78 (q, 2H), 4.20 (t, 2H), 4.93 (t, 1H), 6.80 (d, 1H), 7.42 (dd, 1H), 7.80 (d, 1H), 8.13 (m, 1H), 8.49 (dd, 1H), 9.00 (d, 1H).

C] 1-(2-Chloroethyl)-3-(3-pyridinyl)-1H-pyrazole:

1.51 g (8 mmol) 1-(2-hydroxyethyl)-3-(3-pyridyl)-1H-pyrazole was dissolved in 80 ml dioxane. To this solution was added 1.52 ml (21.6 mmol) thionyl chloride dropwise over 5 minutes and the resulting mixture was stirred for 12 hours at room temperature. The mixture was concentrated in vacuo, dissolved in water (30 ml) and basified with solid $K_2CO_3$. The aqueous solution was extracted with $CH_2Cl_2$ and the organic layer was dried and evaporated to give an oil. This was chromatographed on silica gel (120 g) using a gradient of methanol in $CH_2Cl_2$ (0 to 8%) as an eluent. The appropriate fractions were combined and evaporated to give 1.17 g (70%) of a brownish solid. MS (EI): 207.1 ($M^+$). $^1$H-NMR (DMSO-d6): 4.05 (t, 2H), 4.52 (t, 2H), 6.85 (d, 1H), 7.43 (dd, 1H), 7.90 (d, 1H), 8.15 (m, 1H), 8.50 (dd, 1H), 9.02 (d, 1H).

D] Ethanethioic acid, S-[2-[3-(3-pyridinyl)-1H-pyrazol-1-yl]ethyl]ester: According to example 14D, 1.04 g 1-(2-chloroethyl)-3-(3-pyridyl)-1H-pyrazole were treated with 720 mg potassium thioacetate to give a crude product. This was distilled bulb to bulb at 160–165° C. (0.2 mbar) to give 1.15 g (93%) of an orange oil. MS (EI): 247.1 ($M^+$).

¹H-NMR (DMSO-d6): 2.34 (s, 3H), 3.33 (t, 2H), 4.33 (t, 2H), 6.82 (d, 1H), 7.42 (dd, 1H), 7.85 (d, 1H), 8.13 (m, 1H), 8.50 (dd, 1H), 9.00 (d, 1H).

E] [3-(3-pyridinyl)-1H-pyrazole]-1-ethanethiol was obtained according to example 14E from ethanethioic acid, S-[2-[3-(3-pyridyl)-1H-pyrazol-1-yl]ethyl]ester. MS (ISP): 206.2 (MH⁺). ¹H-NMR (DMSO-d6): 2.41 (broad t, 1H), 2.96 (broad q, 2H), 4.32 (t, 2H), 6.83 (d, 1H), 7.42 (m, 1H), 7.87 (d, 1H), 8.14 (m, 1H), 8.49 (m, 1H), 9.01 (d, 1H).

F] (10E)-10,11-Didehydro-11-deoxy-6-O-methyl-erythromycin 2'-acetate 4"-(phenylmethyl carbonate)12-[[[2-[3-(3-pyridinyl)-1H-pyrazol-1-yl]ethyl]thio]acetate]; (IV-16):

Was obtained according to example 14F from IX-1 (300 mg) and [3-(3-pyridinyl)-1H-pyrazole]ethanethiol (125 mg) to give 286 mg of the desired product (IV-16). $R_f$: 0.70 (CHCl₃/MeOH/NH₄OH 9:1:0.1). MS (ISP): 1151.3 (MH⁺), 576.6 ([MH₂]⁺⁺). ¹H-NMR (CDCl3) diagnostic signals only: 1.59 (s, 3H), 1.86 (s, 3H), 2.01 (s, 3H), 2.25 (s, 6H), 3.06 (s, 2H), 3.12 (t, 2H), 3.15 (s, 3H), 3.32 (s, 3H), 4.37 (t, 2H0, 4.46 (d, 1H), 4.57 (d, 1H), 4.68 (dd, 1H), 4.98 (d, 1H), 5.14 (d, 1H), 5.26 (d, 1H), 5.72 (dd, 1H), 6.58 (d, 1H), 6.61 (s, 1H), 7.30 (m, 1H), 7.35 (s, 5H), 7.50 (d, 1H), 8.08 (m, 1H), 8.53 (m, 1H), 9.01 (m, 1H).

G] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-3-[[2-[3-(3-pyridinyl)-1H-pyrazol-1-yl]ethyl]thio]-2H-furo[2,3-c]oxacyclotetradecin-2,5,13(3H,6H)-trione; (V-16):

According to example 6E, IV-16 (286 mg) was treated with 14 mg NaH dispersion to give the desired product V-16 (260 mg) as a single diasteromer: $R_f$: 0.16 (CH₃CN/CH₂Cl₂/NH₄OH 1:1:0.01). MS (ISP): 1151.3 (MH⁺), 576.6 ([MH₂]⁺⁺).

H] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[[2-[3-(3-pyridinyl)-1H-pyrazol-1-yl]ethyl]thio]-2H-furo[2,3-c]oxacyclotetradecin-2,5,13(3H,6H)-trione; (VI-16):

According to example 1D, V-16 (260 mg) was subjected to acidic methanolysis to give product VI-16 (112 mg) as a single diasteromer. $R_f$: 0.20 (ethyl acetate/MeOH/NEt₃ 9:1:0.1). MS (ISP): 859.4 (MH⁺), 430.3 ([MH₂]⁺⁺). ¹H-NMR (CDCl3) diagnostic signals only: 1.47 (s, 3H), 2.07 (s, 3H), 2.26 (s, 6H), 2.67 (s, 1H), 2.94 (s, 3H), 3.76 (d, 1H), 4.77 (dd, 1H), 5.52 (dd, 1H), 6.50 (d, 1H), 7.31 (m, 1H), 7.80 (d, 1H), 8.09 (m, 1H), 8.52 (m, 1H), 8.98 (d, 1H).

I] (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-15-ethyloctahydro-8-methoxy-4,6,8,10,12,15a-hexamethyl-3-[[2-[3-(3-pyridinyl)-1H-pyrazol-1-yl]ethyl]thio]-2H-furo[2,3-c]oxacyclotetradecin-2,5,11,13 (3H,6H,12H)-tetrone; (VII-16):

Was obtained from VI-16 (112 mg) according to example 1E to give the ketolide VII-16 (98 mg) as a single diastereomer. $R_f$: 0.34 (CHCl₃/MeOH/NH₄OH 9:1:0.1). MS (ISP): 857.4 (MH⁺), 429.7 ([MH₂]⁺⁺). ¹H-NMR (CDCl3) diagnostic signals only: 1.52 (s, 3H), 2.06 (s, 3H), 2.26 (s, 6H), 2.63 (s, 1H), 2.68 (s, 3H), 3.82 (q, 1H), 4.77 (dd, 1H), 5.43 (dd, 1H), 6.51 (d, 1H), 7.30 (m, 1H), 7.78 (d, 1H), 8.09 (m, 1H), 8.53 (m, 1H), 8.98 (d, 1H).

K] (3S,3aR,4R,6R,8R,9R,10R,12R,15R,15aS)-15-Ethyloctahydro-8-methoxy-4,6,8,10,12,15a-hexamethyl-3-[[2-[3-(3-pyridinyl)-1H-pyrazol-1-yl]ethyl]thio-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-16):

VII-16 (98 mg) was deprotected according to example 1F to give 71 mg of the desired ketolide I-16. $R_f$: 0.20 (CHCl₃/MeOH/NH₄OH 9:1:0.1). MS (ISP): 815.6 (MH⁺), 408.7 ([MH₂]⁺⁺). ¹H-NMR (CDCl3) diagnostic signals only: 0.87 (t, 3H), 1.15 (2d, 6H), 1.27 (d, 3H), 1.32 (d, 3H), 1.33 (s, 3H), 1.34 (d, 3H), 1.52 (s, 3H), 2.29 (s, 6H), 2.63 (s, 1H), 2.67 (s, 3H), 2.84 (q, 1H), 4.28 (d, 1H), 4.34 (s, 1H), 4.35 (d, 1H), 4.45–4.51 (m, 2H), 5.42 (dd, 1H), 6.50 (d, 1H), 7.29 (m, 1H), 7.78 (d, 1H), 8.08 (m, 1H), 8.52 (m, 1H), 8.98 (d, 1H).

EXAMPLE 17

Preparation of (3S,3aR,4R,6R,8R,9R,10R,12R,15R,15aS)-15-Ethyloctahydro-8-methoxy-4,6,8,10,12,15a-hexamethyl-3-[[2-[3-(3-pyridinyl)-1H-1,2,4-triazol-1-yl]ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-17, Compound of Formula I, Where $R^1$ is [2-[3-(3-pyridinyl)-1H-1,2,4-triazol-1-yl]ethyl] thio)

A] 3-(3-Pyridinyl)-2H-1,2,4-triazole was prepared according to Lin et al. *J. Org. Chem.* 1979, 44, 4160.

B] (2-Hydroxyethyl)-3-(3-pyridinyl)-1H-1,2,4-triazole:

In analogy to example 14B, this compound was obtained from 3-(3-pyridyl)-2H-1,2,4-triazole by treatment with ethylene carbonate. MS (EI): 190.1 (M⁺). ¹H-NMR (DMSO-d6): 3.80 (q, 2H), 4.29 (t, 2H), 5.01 (t, 1H), 7.50 (m, 1H), 8.31 (m, 1H), 8.59 (s, 1H), 8.62 (m, 1H), 9.17 (d, 1H).

C] (2-Chloroethyl)-3-(3-pyridinyl)-1H-1,2,4-triazole:

In analogy to example 14C, this compound was obtained by treating (2-hydroxyethyl)-3-(3-pyridyl)-1H-1,2,4-triazole with SOCl₂. MS (EI): 208.1 (M⁺). ¹H-NMR (DMSO-d6): 3.97 (t, 2H), 4.54 (t, 2H), 7.38 (m, 1H), 8.21 (s, 1H), 8.36 (m, 1H), 8.65 (m, 1H), 9.34 (d, 1H).

D] Ethanethioic acid, S-[[3-(3-pyridinyl)-1H-1,2,4-triazole-1-yl]ethyl]ester:

In analogy to example 14D, this compound was obtained from (2-chloroethyl)-3-(3-pyridyl)-1H-1,2,4-triazole by treatment with potassium thioacetate. MS (EI): 248.1 (M⁺). ¹H-NMR (DMSO-d6): 2.34 (s, 3H), 3.36 (t, 2H), 4.44 (t, 2H), 7.51 (m, 1H), 8.31 (m, 1H), 8.63 (m, 1H), 8.67 (s, 1H), 9.16 (d, 1H).

E] [3-(3-Pyridinyl)-1H-1,2,4-triazole-1-yl]-1-ethane thiol:

In analogy to example 14E, this compound was obtained on treatment of ethanethioic acid, S-[[3-(3-pyridyl)-1H-1,2,4-triazole-1-yl]ethyl]ester with NH₃. MS (EI): 206.1 (M⁺). ¹H-NMR (DMSO-d6): 2.50 (broad t, 1H), 2.98 (broad q, 2H), 4.41 (t, 2H), 7.51 (m, 1H), 8.31 (m, 1H), 8.62 (m, 1H), 8.67 (s, 1H), 9.17 (s, 1H).

F] (10E)-10,11-Didehydro-11-deoxy-6-O-methyl-erythromycin 2'-acetate 4"-(phenylmethyl carbonate)12-[[[2-[3-(3-pyridinyl)-1H-1,2,4-triazol-1-yl]ethyl]-thio]acetate]; (IV-17):

According to example 14F, treatment of 300 mg IX-1 with 95 mg [3-(3-pyridinyl)-1H-1,2,4-triazole-1-yl]-1-ethanethiol gave 325 mg of IV-17. $R_f$: 0.51 (CHCl$_3$/MeOH/NH$_4$OH 9:1:0.1). MS (ISP): 1152.4 (MH$^+$), 577.1 ([MH$_2$]$^{++}$). $^1$H-NMR (CDCl$_3$) diagnostic signals only: 1.61 (s, 3H), 1.88 (s, 3H), 2.01 (s, 3H), 2.24 (s, 6H), 3,13 (s, 2H), 3.15 (s, 3H), 3.32 (s, 3H), 4.27–4.50 (m, 4H), 4.57 (d, 1H), 4.68 (dd, 1H), 4.98 (d, 1H), 5.73 (dd, 1H), 6.61 (s, 1H), 7.36 (m, 6H), 8.19 (s, 1H), 8.37 (m, 1H), 8.64 (m, 1H), 9,32 (m, 1H).

G] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-3-[[2-[3-(3-pyridinyl)-1H-1,2,4-triazol-1-yl]ethyl]thio]-2H-furo[2,3-c]oxacyclotetradecin-2,5,13(3H,6H)-trione; (V-17):

According to example 6E, 325 mg IV-17 was treated with 21 mg NaH dispersion (60%) to give 283 mg of V-17 as a single diastereomer. $R_f$: 0.62 (CHCl$_3$/MeOH/NH$_4$OH 9:1:0.1). MS (ISP): 1152.4 (MH$^+$), 577.1 ([MH$_2$]$^{++}$). $^1$H-NMR (CDCl$_3$) diagnostic signals only: 1.37 (s, 3H), 1.45 (s, 3H), 2.04 (s, 3H), 2.25 (s, 6H), 2.58 (s, 1H), 3.00 (s, 3H), 3.32 (s, 3H), 4.89 (d, 1H), 5.13 (d, 1H), 5.27 (d, 1H), 5.34 (dd, 1H), 7.36 (m, 6H), 8.32 (m, 1H), 8.55 (s, 1H), 8.62 (m, 1H), 9.30 (d, 1H).

H] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[[2-[3-(3-pyridinyl)-1H-1,2,4-triazol-1-yl]ethyl]thio]-2H-furo[2,3-c]oxacyclotetradecin-2,5,13(3H,6H)-trione; (VI-17):

According to example 14H, 264 mg V-17 were subjected to methanolysis to give 200 mg of VI-17 as a single diastereomer. $R_f$: 0.27 (CHCl$_3$/MeOH/NH$_4$OH 9:1:0.1). MS (ISP): 860.5 (MH$^+$), 431.4 ([MH$_2$]$^{++}$). $^1$H-NMR (CDCl$_3$) diagnostic signals only: 0.83 (t, 3H), 0.97 (d, 3H), 1.32 (s, 3H), 1.47 (s, 3H), 2.07 (s, 3H), 2.26 (s, 6H), 2.64 (s, 1H), 2.92 (s, 3H), 3.63 (dt, 1H), 3.76 (d, 1H), 4.53 (s, 1H), 4.64 (m, 3H), 4.77 (dd, 1H), 5.42 (dd, 1H), 7.37 (m, 1H), 8.33 (m, 1H), 8.51 (s, 1H), 8.60 (m, 1H), 9.28 (d, 1H).

I] (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-15-ethyloctahydro-8-methoxy-4,6,8,10,12,15a-hexamethyl-3-[[2-[3-(3-pyridinyl)-1H-1,2,4-triazol-1-yl]ethyl]thio]-2H-furo[2,3-c]oxacyclotetradecin-2,5,11,13(3H,6H,12H)-tetrone; (VII-17):

200 mg VI-17 were oxidized according to example 14I to give 170 mg of VII-17 as a single diastereomer. $R_f$: 0.58 (CHCl$_3$/MeOH/NH$_4$OH 9:1:0.1). MS (ISP): 858.3 (MH$^+$), 430.1 ([MH$_2$]$^{++}$). $^1$H-NMR (CDCl$_3$) diagnostic signals only: 1.52 (s, 3H), 2.04 (s, 3H), 2.25 (s, 6H), 2.62 (s, 1H), 2.65 (s, 3H), 3.82 (q, 1H), 4.27 (d, 1H), 4.35 (s, 1H), 4.41 (d, 1H), 4.62 (m, 2H), 4.76 (dd, 1H), 5.37 (dd, 1H), 7.37 (m, 1H), 8.32 (m, 1H), 8.51 (s, 1H), 8.62 (m, 1H), 9.30 (s, 1H).

K] (3S,3aR,4R,6R,8R,9R,10R,12R,15R,15aS)-15-Ethyloctahydro-8-methoxy-4,6,8,10,12,15a-hexamethyl-3-[[2-[3-(3-pyridinyl)-1H-1,2,4-triazol-1-yl]ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-17):

170 mg VII-17 were deprotected according to example 14K to give 170 mg of the desired product: $R_f$: 0.45 (CHCl$_3$/MeOH/NH$_4$OH 9:1:0.1). MS (ISP): 816.4 (MH$^+$), 409.2 ([MH$_2$]$^{++}$). $^1$H-NMR (CDCl$_3$) diagnostic signals only: 0.86 (t, 3H), 1.16 (2d, 6H), 1.26 (d, 3H), 1.53 (s, 3H), 2.29 (s, 6H), 2.61 (s, 1H), 2.66 (s, 3H), 3.83 (q, 1H), 4.29 (d, 1H), 4.33 (s, 1H), 4.33 (s, 1H), 4.61 (m, 2H), 5.36 (dd, 1H), 7.36 (m, 1H), 8.33 (m, 1H), 8.53 (s, 1H), 8.62 (m, 1H), 9.29 (s, 1H).

EXAMPLE 18

Preparation of (3S,3aR,4R,6R,8R,9R,10R,12R,15R,15aS)-15-Ethyloctahydro-8-methoxy-4,6,8,10,12,15a-hexamethyl-3-[[2-[3-(4-pyridinyl)-1H-1,2,4-triazol-1-yl)]ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-18, Compound of Formula I, Where $R^1$ is [2-[3-(4-pyridinyl)-1H-1,2,4-triazol-1-yl)]ethyl]thio)

A] 3-(4-Pyridinyl)-1H-1,2,4-triazole was prepared according to Lin et al. *J. Org. Chem.* 1979, 44, 4160.

B] 1-(2-Hydroxyethyl)-3-(4-pyridinyl)-1H-1,2,4-triazole was prepared according to example 14B from 5-(4-pyridinyl)-(2H)-triazole and ethylene carbonate. MS (EI): 190.1 (M$^+$). $^1$H-NMR (DMSO-d6): 3.79 (q, 2H), 4.30 (t, 2H), 5.01 (t, 1H), 7.91 (m, 2H), 8.63 (s, 1H), 8.67 (m, 2H).

C] 1-(2-Chloroethyl)-3-(4-pyridinyl)-1H-1,2,4-triazole was obtained according to example 14C from 1-(2-hydroxyethyl)-3-(4-pyridinyl)-1H-1,2,4-triazole by treatment with SOCl$_2$. MS (EI): 208.1 M$^+$). $^1$H-NMR (DMSO-d6): 4.09 (t, 2H), 4.64 (t, 2H), 7.92 (m, 2H), 8.69 (m, 2H), 8.76 (s, 1H).

D] Ethanethioic acid, S-[[3-(4-pyridinyl)-1H-1,2,4-triazol-1-yl]ethyl]ester was obtained according to example 14D from 1-(2-chloroethyl)-3-(4-pyridinyl)-1H-1,2,4-triazole by treatment with potassium thioacetate. MS (EI): 248.1 (M+). $^1$H-NMR (CDCl$_3$): 2.38 (s, 3H), 3.39 (t, 2H), 4.40 (t, 2H), 7.96 (m, 2H), 8.14 (s, 1H), 8.70 (m, 2H).

E] [3-(4-Pyridinyl)-1H-1,2,4-triazole]-1-ethanethiol was obtained according to example 14E ethanethioic acid, S-[2-[3-(4-pyridyl)-1H-1,2,4-triazol-1-yl]ethyl]ester by treatment with gaseous NH$_3$. MS (EI): 206.1 (M$^+$). $^1$H-NMR (DMSO-d6): 2.51 (broad t, 1H), 2.99 (broad q, 2H), 4.43 (t, 2H), 7.91 (m, 2H), 8.68 (m, 2H), 8.71 (s, 1H).

F] (10E)-10,11-Didehydro-11-deoxy-6-O-methyl-erythromycin 2'-acetate 4"-(phenylmethyl carbonate)12-[[[2-[3-(4-pyridinyl)-1H-1,2,4-triazol-1-yl)]ethyl]thio]acetate]; (IV-18):

Was obtained according to example 14F from 333 mg IX-1 and 105 mg [3-(4-pyridinyl)-1H-1,2,4-triazole]-1-ethanethiol. Yield 307 mg. $R_f$: 0.49 (CHCl$_3$/MeOH/NH$_4$OH 9:1:0.1). MS (ISP): 1152.4 (MH$^+$). $^1$H-NMR (CDCl$_3$) diagnostic signals only: 1.61 (s, 3H), 1.89 (s, 3H), 2.00 (s, 3H), 2.23 (s, 6H), 3.32 (s, 3H), 4.27–4.51 (m, 4H), 4.57 (d, 1H), 4.68 (dd, 1H), 4.98 (d, 1H), 5.13 (d, 1H), 5.26 (d, 1H), 5.73 (dd, 1H), 6.01 (s, 1H), 7.95 (m, 2H), 8.21 (s, 1H), 8.71 (m, 2H).

G] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-3-[[2-[3-(4-pyridinyl)-1H-1,2,4-triazol-1-yl)]ethyl]thio]-2H-furo[2,3-c]oxacyclotetradecin-2,5,13(3H,6H)-trione; (V-18):

According to example 6E, 307 mg IV-18 were treated with 20 mg NaH dispersion (55%) to give 94 mg of the desired compound V-18. $R_f$: 0.70 (CHCl$_3$/MeOH/NH$_4$OH 9:1:0.1). MS (ISP): 1152.4 (MH$^+$), 577.1 ([MH$_2$]$^{++}$).

H] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[[2-[3-(4-pyridinyl)-1H-1,2,4-triazol-1-yl)]ethyl]thio]-2H-furo[2,3-c]oxacyclotetradecin-2,5,13(3H,6H)-trione; (VI-18):

According to example 14H, 94 mg V-18 were treated with 3% HCl in methanol to give 46 mg of VI-18. $R_f$: 0.41 (CHCl$_3$/MeOH/NH$_4$OH 9:1:0.1). MS (ISP): 860.5 (MH$^+$). $^1$H-NMR (CDCl$_3$) diagnostic signals only: 1.36 (s, 3H), 1.48 (s, 3H), 2.08 (s, 3H), 2.27 (s, 6H), 2.62 (s, 1H), 3.81 (d, 2H), 5.43 (dd, 1H), 7.97 (m, 2H), 8.53–8.73 (m, 3H).

I] (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-15-ethyloctahydro-8-methoxy-4,6,8,10,12,15a-hexamethyl-3-[[2-[3-(4-pyridinyl)-1H-1,2,4-triazol-1-yl)]ethyl]thio]-2H-furo[2,3-c]oxacyclotetradecin-2,5,11,13(3H,6H,12H)-tetrone; (VII-18):

46 mg VI-18 were oxidized in analogy to example 1E to give 43 mg of VII-18. $R_f$: 0.47 (CHCl$_3$/MeOH/NH$_4$OH 9:1:0.1). MS (ISP): 858.3 (MH$^+$), 430.1 ([MH$_2$]$^{++}$). $^1$H-NMR (CDCl$_3$) diagnostic signals only: 0.85 (t, 3H), 1.52 (s, 3H), 2.05 (s, 3H), 2.27 (s, 6H), 2.62 (s, 1H), 2.64 (s, 3H), 3.81 (s, 1H), 4.27 (d, 1H), 4.35 (s, 1H), 4.41 (d, 1H), 4.62 (m, 2H), 4.77 (dd, 1H), 5.43 (dd, 1H), 7.93 (broad m, 2H), 8.53 (s, 1H), 8.68 (broad m, 2H).

K] (3S,3aR,4R,6R,8R,9R,10R,12R,15R,15aS)-15-Ethyloctahydro-8-methoxy-4,6,8,10,12,15a-hexamethyl-3-[[2-[3-(4-pyridinyl)-1H-1,2,4-triazol-1-yl)]ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-18):

Final deprotection was done according to example 1F with 43 mg VII-18 to give 37 mg of deprotected ketolide. $R_f$: 0.30 (CHCl$_3$/MeOH/NH$_4$OH 9:1:0.1). MS (ISP): 816.2 (MH$^+$), 409.2 ([MH$_2$]$^{++}$). $^1$H-NMR (CDCl$_3$) diagnostic signals only: 0.86 (t, 3H), 1.16 (2d, 6H), 1.53 (s, 3H), 2.29 (s, 6H), 2.61 (s, 1H), 2.65 (s, 3H), 3.84 (q, 1H), 4.22–4.38 (m, 3H), 4.62 (m, 2H), 5.33 (dd, 1H), 7.93 (broad m, 2H), 8.54 (s, 1H), 8.68 (broad m, 2H).

EXAMPLE 19

Preparation of (3S,3aR,4R,6R,8R,9R,10R,12R,15R,15aS)-15-Ethyloctahydro-8-methoxy-4,6,8,10,12,15a-hexamethyl-3-[[2-[3-(4-pyridinyl)-1H-pyrazol-1-yl]ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-19, Compound of Formula I, Where $R^1$ is [2-[3-(4-pyridinyl)-1H-pyrazol-1-yl]ethyl]thio)

A] 3-(4-Pyridinyl)-1H-pyrazole was prepared according to *Schunack Arch. Pharmaz*. 1973, 306, 934.

B] 1-(2-Hydroxyethyl)-3-(4-pyridinyl)-1H-pyrazole was obtained according to example 14B from 3-(4-pyridinyl)-1H-pyrazole by treatment with ethylene carbonate. MS (EI): 158.1 (M$^+$). $^1$H-NMR (DMSO-d6): 3.79 (q, 2H), 4.22 (t, 2H), 4.93 (t, 1H), 6.88 (d, 1H), 7.74 (m, 2H), 7.83 (d, 1H), 8.56 (m, 2H).

C] 1-(2-Chloroethyl)-3-(4-pyridinyl)-1H-pyrazole was prepared according to example 14C from 1-(2-hydroxyethyl)-3-(4-pyridinyl)-1H-pyrazole by treatment with SOCl$_2$. MS (EI): 207.1 (M$^+$). $^1$H-NMR (DMSO-d6): 4,06 (t, 2H), 4.53 (t, 2H), 6.92 (d, 1H), 7.76 (m, 2H), 7.93 (d, 1H), 8.58 (m, 2H).

D] Ethanethioic acid, S-[[3-(4-pyridinyl)-1H-pyrazol-1-yl]ethyl]ester was prepared according to example 14D from 1-(2-chloroethyl)-3-(4-pyridinyl)-1H-pyrazole by treatment with potassium thioacetate. MS (EI): 247.1 (M$^+$). $^1$H-NMR (DMSO-d6): 2.34 (s, 3H), 3.34 (t, 2H), 4.35 (t, 2H), 6.89 (d, 1H), 7.75 (m, 2H), 7.88 (d, 1H), 8.57 (m, 2H).

E] [3-(4-Pyridinyl)-1H-pyrazole]-1-ethanethiol was prepared according to example 14E from ethanethioic acid, S-[2-3-(4-pyridinyl)-1H-pyrazol-1-yl]ethyl]ester by treatment with gaseous NH$_3$. MS (EI): 205.1 (M$^+$). $^1$H-NMR (CDCl$_3$): 1.38 (t, 1H), 3.05 (td, 2H), 4.36 (t, 2H), 6.65 (d, 1H), 7.52 (d, 1H), 7.67 (m, 2H), 8.62 (m, 2H).

F] (10E)-10,11-Didehydro-11-deoxy-6-O-methyl-erythromycin 2'-acetate 4"-(phenylmethyl carbonate)12-[[[2-[3-(4-pyridinyl)-1H-pyrazol-1-yl]ethyl]thio]acetate]; (IV-19):

Was prepared according to example 14F from [3-(4-pyridinyl)-1H-pyrazole]-1-ethane thiol (77 mg) and IX-1 (243 mg) to give 265 mg of IV-19. $R_f$: 0.52 (CHCl$_3$/MeOH/NH$_4$OH 9:1:0.1). MS (ISP): 1151.3 (MH$^+$), 576.7 ([MH$_2$]$^{++}$). $^1$H-NMR (CDCl$_3$) diagnostic signals only: 1.59 (s, 3H), 1.87 (s, 3H), 2.01 (s, 3H), 2.24 (s, 6H), 3.07 (s, 2H), 3.11 (t, 2H), 3.15 (s, 3H), 3.32 (s, 3H), 4.37 (t, 2H), 4.46 (d, 1H), 4.57 (d, 1H), 4.68 (dd, 1H), 4.98 (d, 1H), 5.13 (d, 1H), 5.26 (d, 1H), 5.72 (dd, 1H), 6.61 9s, 1H), 6.65 (d, 1H), 7.35 (s, 5H), 7.51 (d, 1H), 7.68 (m, 2H), 8.62 (m, 2H).

G] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-3-[[2-[3-(4-pyridinyl)-1H-pyrazol-1-yl]ethyl]thio]-2H-furo[2,3-c]oxacyclotetradecin-2,5,13(3H,6H)-trione; (V-19):

243 mg IV-19 were cyclized according to example 6E with 20 mg NaH to give 148 mg V-19 as a single diastereomer. $R_f$: 0.62 (CHCl$_3$/MeOH/NH$_4$OH 9:1:0.1). MS (ISP): 1151.3 (MH$^+$), 576.7 ([MH$_2$]$^{++}$). $^1$H-NMR (CDCl$_3$) diagnostic signals only: 1.35 (s, 3H), 1.44 (s, 3H), 2.04 (s, 3H), 2.25 (s, 6H), 2.56 (s, 1H), 3.00 (s, 3H), 3.32 (s, 3H), 4.92 (d, 1H), 5.13 (d, 1H), 5.27 (d, 1H), 5.41 (dd, 1H), 6.57 (d, 1H), 7.36 (s, 5H), 7.67 (m, 2H), 7,82 (d, 1H), 8.60 (m, 2H).

H] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[[2-[3-(4-pyridinyl)-1H-pyrazol-1-yl]ethyl]thio]-2H-furo[2,3-c]oxacyclotetradecin-2,5,13(3H,6H)-trione; (VI-19):

In analogy to example 14H, 138 mg V-19 were subjected to methanolysis to give 98 mg of VI-19. $R_f$: 0.38 (CHCl$_3$/MeOH/NH$_4$OH 9:1:0.1). MS (ISP): 859.4 (MH$^+$), 430.6 ([MH$_2$]$^{++}$). $^1$H-NMR (CDCl$_3$) diagnostic signals only: 1.32 (s, 3H), 1.47 (s, 3H), 2.08 (s, 3H), 2.26 (s, 6H), 2.65 (s, 1H), 2.91 (s, 3H), 3.78 (d, 1H), 5.52 (dd, 1H), 6.54 (d, 1H), 7.67 (m, 2H), 7.86 (d, 1H), 8.54 (m, 2H).

I] (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-15-ethyloctahydro-8-methoxy-4,6,8,10,12,15a-hexamethyl-3-[[2-[3-(4-pyridinyl)-1H-pyrazol-1-yl]ethyl]thio]-2H-furo[2,3-c]oxacydotetradecin-2,5,11,13(3H,6H,12H)-tetrone; (VII-19):

Oxidation was done in analogy to example 1E with 98 mg VI-19 to give 80 mg of VII-19: $R_f$: 0.32 (1% NH$_4$OH in CH$_3$CN). MS (ISP): 857.4 (MH$^+$), 429.7 ([MH$_2$]$^{++}$). $^1$H-NMR (CDCl$_3$) diagnostic signals only: 1.52 (s, 3H), 2.05 (s, 3H), 2.25 (s, 6H), 2.63 (s, 1H), 2.67 (s, 3H), 4.82 (q, 1H), 4.27 (d, 1H), 4.36 (s, 1H), 4.55 (m, 2H), 4.66 (dd, 1H), 5.42 (dd, 1H), 6.56 (d, 1H), 7.67 (m, 2H), 7.79 (d, 1H), 8.61 (m, 2H).

K] (3S,3aR,4R,6R,8R,9R,10R,12R,15R,15aS)-15-Ethyloctahydro-8-methoxy-4,6,8,10,12,15a-hexamethyl-3-[[2-[3-(4-pyridinyl)-1H-pyrazol-1-yl]ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-19):

Final deprotection was done according to example 1F with 80 mg VII-19 to give the desired ketolide in quantitative yield: $R_f$: 0.32 (CHCl$_3$/MeOH/NH$_4$OH 9:1:0.1). MS (ISP): 815.4 (MH$^+$), 408.8 ([MH$_2$]$^{++}$). $^1$H-NMR (CDCl$_3$) diagnostic signals only: 0.86 (t, 3H), 1.15 (2d, 6H), 1.26 (d, 3H), 1.31 (d, 3H), 1.33 (s, 3H), 1.35 (d, 3H), 1.52 (s, 3H), 2.27 (s, 6H), 2.61 (s, 1H), 2.68 (s, 3H), 3.84 (q, 1H), 4.28 (s, 1H), 4.33 (s, 1H), 4.33 (d, 1H), 4.56 (m, 2H), 5.41 (dd, 1H), 6.57 (d, 1H), 7.66 (m, 2H), 7.79 (d, 1H), 8.60 (m, 2H).

EXAMPLE 20

Preparation of (3S,3aR,4R,6R,8R,9R,10R,12R,15R,15aS)-15-Ethyloctahydro-8-methoxy-4,6,8,10,12,15a-hexamethyl-3-[[2-[4-(3-pyridinyl)-1H-imidazol-1-yl]ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-20, Compound of Formula I, Where R$^1$ is [2-[4-(3-pyridinyl)-1H-imidazol-1-yl]-ethyl]thio)

A] 4-(3-Pyridinyl)-1H-imidazole was prepared according to Clemo et al. *J. Chem. Soc.* 1934, 753–755.

B] 1-(2-Hydroxyethyl)-4-(3-pyridinyl)-1H-imidazole:

According to example 14B, 3.4 g 4-(3-pyridinyl)-1H-imidazole gave 3.8 g (86%) of the desired compound as an oil. In this case, the product was purified by flash chromatography. $^1$H-NMR (CDCl$_3$): 3.92 (t, 2H), 4.05 (t, 2H), 7.18 (s, 1H), 7.24 (dd, 1H), 7.49 (s, 1H), 7.86 (m, 1H), 8.37 (m, 1H), 8.67 (d, 1H).

C] 1-(2-Chloroethyl)-4-(3-pyridinyl)-1H-imidazole:

In analogy to example 14C, 2.91 g 1-(2-hydroxyethyl)-4-(3-pyridinyl)-1H-imidazole were allowed to react with 2.8 ml SOCl$_2$. 543 mg (17%) of purified (flash chromatography) product were obtained. MS (ISP): 208 (MH$^+$). $^1$H-NMR (CDCl$_3$): 3.82 (t, 2H),4.34 (t, 2H), 7.32 (dd, 1H), 7.35 (s, 1H), 7.63 (s, 3H), 8.11 (m, 1H), 8.51 (m, 1H), 8.99 (d, 1H).

D] Ethanethioic acid, S-[[4-(3-pyridinyl)-1H-imidazol-1-yl]ethyl]ester:

According to example 14D, a solution of 540 mg (2.6 mmol) 1-(2-chloroethyl)-4-(3-pyridinyl)-1H-imidazole was treated with 370 mg (3.25 mmol) potassium thioacetate to give the corresponding thioester that was used without further purification. MS (ISP): 248.0 (MH$^+$).

E] [4-(3-Pyridinyl)-1H-imidazole]-1-ethanethiol:

As shown in example 14E, 532 mg ethanethioic acid, S-[2-[4-(3-pyridinyl)-1H-imidazol-1-yl]ethyl]ester were treated with NH$_3$ gas to give the crude thiol that was used without further purification (main impurity was acetamide). MS (ISP): 206.0 (MH$^+$). $^1$H-NMR (CDCl$_3$): 1.44 (broad t, 1H), 2.94 (broad q, 2H), 4.20 (t, 2H), 7.31 (dd, 1H), 7.32 (s, 1H), 7.62 (s, 1H), 8.11 (m, 1H), 8.49 (m, 1H), 8.97 (d, 1H).

F] (10E)-10,11-Didehydro-11-deoxy-6-O-methyl-erythromycin 2'-acetate 4"-(phenylmethyl carbonate)12-[[[2-[4-(3-pyridinyl)-1H-imidazol-1-yl]ethyl]-thio]acetate]; (IV-20):

According to example 14F, 300 mg IX-1 were treated with 125 mg [4-(3-pyridyl)-1H-imidazole]-1-ethanethiol to give 180 mg (51%) of IV-20. $R_f$: 0.40 (CHCl$_3$/MeOH/NH$_4$OH 9:1:0.1). MS (ISP): 1151.5 (MH$^+$), 576.9 ([MH$_2$]$^{++}$). $^1$H-NMR (CDCl$_3$) diagnostic signals only: 1.88 (s, 3H), 2.02 (s, 3H), 2.23 (s, 6H), 2.99 (t, 2H), 3.08 (s, 2H), 3.13 (s, 3H), 3.33 (s, 3H), 4.20 (t, 2H), 4.34 (m, 1H), 4.47 (d, 1H), 4.56 (d, 1H), 4.69 (dd, 1H), 4.98 (d, 1H), 5.13 (d, 1H), 5.27 (d, 1H), 5.72 (dd, 1H), 6.60 (s, 1H), 7.32 (m, 1H), 7.36 (s, 1H), 7.37 (s, 5H), 7.61 (s, 1H), 8.10 (m, 1H), 8.49 (m, 1H), 8.99 (d, 1H).

G] (3R or S,3aR,4R or S,6R,8R,9R,10S,11S,12R,15R,15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-3-[[2-[4-(3-pyridinyl)-1H-imidazol-1-yl]ethyl]thio]-2H-furo[2,3-c]oxacyclotetradecin-2,5,13(3H,6H)-trione; mixture of 2 diastereomers (V-20):

According to example 1C, 480 mg IV-20 were cyclized using KO$^t$Bu to give 168 mg of the desired product V-20 as a 9:1 mixture of two diastereomers. $R_f$: 0.33 (CHCl$_3$/MeOH/NH$_4$OH 9:1:0.1). MS (ISP): 1117.3 (MH$^+$), 660.3 ([MH$_2$]$^{++}$).

H] (3R or S,3aR,4R or S,6R,8R,9R,10S,11S,12R,15R,15aS)-9-[[2-O-Acetyl-3,4,6-trideoxy-3-(dimethylamino)-β-D-xylo-hexopyranosyl]oxy]-15ethyldecahydro-11-hydroxy-8-methoxy-4,6,8,10,12,15a-hexamethyl-3-[[2-[4-(3-pyridinyl)-1H-imidazol-1-yl]ethyl]thio]-2H-furo[2,3-c]oxacyclotetradecin-2,5,13 (3H,6H)-trione; mixture of 2 diastereomers (VI-20):

In analogy to example 14H, 184 mg V-20 were subjected to methanolysis to give 104 mg of product VI-20 as a 9:1 mixture of two diastereomers. $R_f$: 0.23 (CHCl$_3$/MeOH/NH$_4$OH 9:1:0.1). MS (ISP): 859.4 (MH$^+$). $^1$H-NMR (CDCl$_3$) diagnostic signals only: (main product) 2.07 (s, 3H), 2.27 (s, 6H), 2.67 (s, 1H), 3.03 (s, 3H), 3.73 (d, 1H), 4.58 (s, 1H), 5.53 (dd, 1H), 7.28 (m, 1H), 7.55 (s, 1H), 7.70 (s, 1H), 8.10 (m, 1H), 8.45 (m, 1H), 9.00 (d, 1H).

I] (3R or S,3aR,4R or S,6R,8R,9R,10R,12R,15R,15aS)-9-[[2-O-Acetyl-3,4,6-trideoxy-3-(dimethylamino)-β-D-xylo-hexopyranosyl]oxy]-15-ethyloctahydro-8-methoxy-4, 6,8,10,12,15a-hexamethyl-3-[[2-[4-(3-pyridinyl)-1H-imidazol-1-yl]ethyl]thio]-2H-furo[2,3-c]oxacyclotetradecin-2,5,11,13(3H,6H,12H)-tetrone; mixture of two diastereomers (VII-20):

According to example 1E, 104 mg VI-20 were oxidized to give 98 mg of the desired ketolide VII-20. $R_f$: 0.49 (CHCl$_3$/MeOH/NH$_4$OH 9:1:0.1). MS (ISP): 857.4 (MH$^+$), 429.7 ([MH$_2$]$^{++}$).

K] (3S,3aR,4R,6R,8R,9R,10R,12R,15R,15aS)-15-Ethyloctahydro-8-methoxy-4,6,8,10,12,15a-hexamethyl-3-[[2-[4-(3-pyridinyl)-1H-imidazol-1-yl]ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-20):

98 mg VII-20 were deprotected according to example 1F to give 42 mg of the desired ketolide. $R_f$: 0.58 (CHCl$_3$/MeOH/NH$_4$OH 9:1:0.1). MS (ISP): 815.3 (MH$^+$), 408.8 ([MH$_2$]$^{++}$). $^1$H-NMR (CDCl$_3$) diagnostic signals only: 0.87 (t, 3H), 1.14 (2 overlapping d, 6H), 1.53 (s, 3H), 2.32 (s, 6H), 2.61 (s, 1H), 2.64 (s, 3H), 3.83 (q, 3H), 4.24 (d, 1H), 4.30–4.40 (m, 4H), 5.43 (dd, 1H), 7.27 (m, 1H), 7.54 (s, 1H), 7.69 (s, 1H), 8.07 (m, 1H), 8.44 (m, 1H), 9.00 (d, 1H).

EXAMPLE 21

Preparation of (3S,3aR,4R,6R,8R,9R,10R,12R,15R,15aS)-15-Ethyloctahydro-8-methoxy-4,6,8,10,12,15a-hexamethyl-3-[[2-[1H-1,2,4-triazol-1-yl]ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-21, Compound of Formula I, Where R$^1$ is [2-[1H-1,2,4-triazol-1-yl]ethyl]thio)

A] 1-(2-Hydroxyethyl)-1H-1,2,4-triazole was obtained according to example 14B from 1H-1,2,4-triazole and ethylene carbonate. MS (EI): 113.1 (M$^+$). $^1$H-NMR (DMSO-d6): 3.7 s (q, 2H), 4.20 (t, 2H), 4.94 (t, 1H), 7.95 (s, 1H), 8.44 (s, 1H).

B] 1-(2-Chloroethyl)-1H-1,2,4-triazole was obtained according to example 14C from 1-(2-hydroxyethyl)-1H-1,2,4-triazole by treatment with SOCl$_2$. MS (EI): 131.1 (M$^+$). $^1$H-NMR (DMSO-d6): 4.01 (t, 2H), 4.54 (t, 2H), 8.01 (s, 1H), 8.57 (s, 1H).

C] Ethanethioic acid, S-[2-(1H-1,2,4-triazol-1-yl)-ethyl] ester was obtained according to example 14D from 1-(2-chloroethyl)-1H-1,2,4-triazole and potassium thioacetate. MS (EI): 129.1 (M$^+$). $^1$H-NMR (DMSO-d6): 2.33 (s, 3H), 3.28 (t, 2H), 4.35 (t, 2H), 7.97 (s, 1H), 8.51 (s, 1H).

D] 1H-1,2,4-Triazole-1-ethanethiol was obtained according to example 14E from ethanethioic acid, S-[2-(1H-1,2,4-triazol-1-yl)-ethyl]ester by treatment with gaseous NH$_3$. MS (EI): 129.1 (M$^+$). $^1$H-NMR (DMSO-d6): 2.41 (broad t, 1H), 2.90 (broad q, 2H), 4.33 (t, 2H), 7.98 (s, 1H), 8.52 (s, 1H).

E] (10E)-10,11-Didehydro-11-deoxy-6-O-methyl-erythromycin 2'-acetate 4"-(phenylmethyl carbonate)12-[[[2-[1H-1,2,4-triazol-1-yl]ethyl]thio]acetate]; (IV-21):

Was obtained according to example 14F from 300 mg IX-1 and 60 mg 1H-1,2,4-triazole-1-ethanethiol to give 328 mg of the desired product. $R_f$: 0.40 (ethyl acetate/methanol/NEt$_3$ 9:1:0.1). MS (ISP): 1075.5 (MH$^+$), 538.8 ([MH$_2$]$^{++}$). $^1$H-NMR (CDCl$_3$) diagnostic signals only: 1.61 (s, 3H), 1.88 (s, 3H), 2.00 (s, 3H), 2.23 (s, 6H), 3.08 (s, 2H), 3.15 (s, 3H), 3.32 (s, 3H), 4.36 (t, 2H), 4.46 (d, 1H), 4.57 (d, 1H), 4.68 (dd, 1H), 4.98 (d, 1H), 5.13 (d, 1H), 5.24 (d, 1H), 5.72 (dd, 1H), 6.60 (s, 1H), 7.95 (s, 1H), 8.13 (s, 1H).

F] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-3-[[2-[1H-1,2,4-triazol-1-yl]ethyl]thio]-2H-furo[2,3-c]oxacyclotetradecin-2,5,13 (3H,6H)-trione; (V-21):

According to example 6E, 295 mg IV-21 were treated with 20 mg NaH-dispersion (55%) to give 236 mg of V-21 as a single diastereomer. $R_f$: 0.63 (CHCl$_3$/MeOH/NH$_4$OH 9:1:0.1). MS (ISP): 1075.5 (MH$^+$), 538.7 ([MH$_2$]$^{++}$). $^1$H-NMR (CDCl$_3$) diagnostic signals only: 0.84 (t, 3H), 0.92 (d, 3H), 1.36 (s, 3H), 1.44 (s, 3H), 2.04 (s, 3H), 2.24 (s, 6H), 2.53 (s, 1H), 2.97 (s, 3H), 3.32 (s, 3H), 4.90 (d, 1H), 5.13 (d, 1H), 5.27 (d, 1H), 5.43 (dd, 1H), 7.91 (s, 1H), 8.54 (s, 1H).

G] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[[2-[1H-1,2,4-triazol-1-yl]ethyl]thio]-2H-furo[2,3-c]oxacyclotetradecin-2,5,13(3H,6H)-trione; (VI-21):

According to example 14H, 214 mg V-21 were subjected methanolysis to give 168 mg of VI-21. $R_f$: 0.23 (CHCl$_3$/MeOH/NH$_4$OH 9:1:0.1). MS (ISP): 783.4 (MH$^+$). $^1$H-NMR (CDCl$_3$) diagnostic signals only: 0.84 (t, 3H), 0.96 (d, 1H), 1.30 (s, 3H), 1.46 (s, 3H), 2.07 (s, 3H), 2.26 (s, 6H), 2.63 (s, 1H), 2.91 (s, 3H), 474 (d, 1H), 4.51 (s, 1H), 4.77 (dd, 1H), 5.42 (dd, 1H), 7.90 (s, 1H), 8.47 (s, 1H).

H] (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-15-ethyloctahydro-8-methoxy-4,6,8,10,12,15a-hexamethyl-3-[[2-[1H-1,2,4-triazol-1-yl]ethyl]thio]-2H-furo[2,3-c]oxacyclotetradecin-2,5,11,13(3H,6H,12H)-tetrone; (I-21):

According to example 1E, 168 mg VI-21 were oxidized to give 141 mg of VII-21: $R_f$: 0.44 (CHCl$_3$/MeOH/NH$_4$OH 9:1:0.1). MS (ISP): 781.3 (MH$^+$). $^1$H-NMR (CDCl$_3$) diagnostic signals only: 0.87 (t, 3H), 1.52 (s, 1H), 2.04 (s, 3H), 2.25 (s, 6H), 2.61 (s, 1H), 2.64 (s, 3H), 3.81 (q, 1H), 4.37 (d, 1H), 4.33 (s, 1H), 4.41 (d, 1H), 4.58 (m, 2H), 4.74 (dd, 1H), 5.35 (dd, 1H), 7.91 (s, 1H), 8.49 (s, 1H).

I] (3S,3aR,4R,6R,8R,9R,10R,12R,15R,15aS)-15-Ethyloctahydro-8-methoxy-4,6,8,10,12,15a-hexamethyl-3-[[2-[1H-1,2,4-triazol-1-yl]ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-21):

According to example 1F, 141 mg VII-21 were deprotected in methanol to give 116 mg of the desired product. MS (ISP): 739.2 (MH$^+$). $^1$H-NMR (CDCl$_3$) diagnostic signals only: 0.86 (t, 3H), 1.15 (2d, 6H), 1.25 (d, 3H), 1.32 (d, 3H), 1.34 (d, 3H), 1.35 (s, 1H), 1.52 (s, 3H), 2.26 (s, 6H), 2.61 (s, 1H), 2.64 (s, 3H), 3.83 (q, 1H), 4.29 (d, 1H), 4.32 (s, 1H), 4.34 (d, 1H), 4.58 (m, 2H), 5.34 (dd, 1H), 7.90 (s, 1H), 8.50 (s, 1H).

EXAMPLE 22

Preparation of (3S,3aR,4R,6R,8R,9R,10R,12R,15R,15aS)-15-Ethyloctahydro-8-methoxy-4,6,8,10,12,15a-hexamethyl-3-[[2-1H-imidazol-1-yl]ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-22, Compound of Formula I, Where $R^1$ is [2-[1H-imidazol-1-yl]-ethyl]thio)

A] 1H-Imidazole-1-ethanethiol was synthesized as described by Girijavallabhan et al. Eur. Pat. Appl. EP 118875 A1, 1984.

B] (10E)-10,11-Didehydro-11-deoxy-6-O-methyl-erythromycin 2'-acetate 4"-(phenylmethyl carbonate)12-[[[2-[1H-imidazol-1-yl]ethyl]thio]acetate]; (IV-22):

Was obtained as described in example 14E from 50 mg IX-1 and 75 mg 1H-Imidazole-1-ethanethiol. $R_f$: 0.64 (CHCl$_3$/MeOH/NH$_4$OH 9:1:0.1). MS (ISP): 1074.7 (MH$^+$), 538.3 ([MH$_2$]$^{++}$). $^1$H-NMR (CDCl$_3$) diagnostic signals only: 1.88 (s, 3H), 2.00 (s, 3H), 2.23 (s, 6H), 2.93 (t, 2H), 3.00 (s, 2H), 3.32 (s, 3H), 4.11 (t, 2H), 4.36 (m, 1H), 4.47 (d, 1H), 4.57 (d, 1H), 4.68 (dd, 1H), 4.98 (d, 1H), 5.14 (d, 1H), 5.27 (d, 1H), 4.72 (dd, 1H), 6.61 (s, 1H), 6.94 (s, 1H), 7.07 (s, 1H), 7.35 (s, 5H), 7.51 (s, 1H).

C] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-3-[[2-[1H-imidazol-1-yl]ethyl]thio]-2H-furo[2,3-c]oxacyclotetradecin-2,5,13 (3H,6H)-trione; (V-22):

283 mg IV-22 were subjected to cyclization with 305 µl KO$^t$Bu solution (1M) according to example 1C to give V-22 along with starting material. $R_f$: 0.59 (CHCl$_3$/MeOH/NH$_4$OH 9:1:0.1).

D] (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[[2-[1H-imidazol-1-yl]ethyl]thio]-2H-furo[2,3-c]oxacyclotetradecin-2,5,13 (3H,6H)-trione; (VI-22):

Methanolysis was performed as described in example 14G to give 18 mg of VI-22 as a single diasteromer. $R_f$: 0.12 (ethyl acetate/MeOH/NEt$_3$ 10:1:0.1). $^1$H-NMR (CDCl$_3$) diagnostic signals only: 2.07 (s, 3H), 2.27 (s, 6H), 2.67 (s, 1H), 2.93 (s, 3H), 3.78 (d, 1H), 4.56 (s, 1H), 5.51 (dd, 1H), 7.00 (s, 1H), 7.12 (s, 1H), 7.62 (s, 1H).

E] (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-15-ethyloctahydro-8-methoxy-4,6,8,10,12,15a-hexamethyl-3-[[2-[1H-imidazol-1-yl]ethyl]thio]-2H-furo[2,3-c]oxacyclotetradecin-2,5,11,13(3H,6H,12H)-tetrone; (VII-22):

18 mg VI-22 were oxidized according to example 1E to give 17 mg of the protected ketolide VII-22 as a single diastereomer. $R_f$: 0.41 (CHCl$_3$/MeOH/NH$_4$OH 9:1:0.1). MS (ISP): 780.4 (MH$^+$), 390.8 ([MH$_2$]$^{++}$).

F] (3S,3aR,4R,6R,8R,9R,10R,12R,15R,15aS)-15-Ethyloctahydro-8-methoxy-4,6,8,10,12,15a-hexamethyl-3-[[2-[1H-imidazol-1-yl]ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-22):

Final deprotection of 17 mg VII-22 was accomplished according to example 1F to give 10 mg of the desired ketolide. MS (ISP): 738.4 (MH$^+$), 369.5 ([MH$_2$]$^{++}$). $^1$H-NMR (CDCl$_3$) diagnostic signals only: 0.87 (t, 3H), 1.14 (2d, 6H), 1.25 (d, 3H), 1.31 (d, 3H), 1.34 (s, 3H), 1.36 (d, 3H), 1.52 (s, 3H), 2.27 (s, 6H), 2.62 (s, 1H), 2.70 (s, 3H), 4.20–4.38 (m, 5H), 5.41 (dd, 1H), 7.02 (s, 2H), 7.67 (s, 1H).

EXAMPLE 23

Preparation of (3R,3aS,4R,6R,8R,9R,10R,12R,15R,15aS)-15-Ethyltetradecahydro-8-methoxy-4,6,8,10,12,15a-hexamethyl-2,5,11,13-tetraoxo-9-[[3,4,6-trideoxy-3-(dimethylamino)-β-D-xylo-hexopyranosyl]oxy]-2H-furo[2,3-c]oxacyclotetradecin-3-carbonitrile; (I-23, Compound of Formula I, Where $R^1$ is Cyano)

A] (10E)-10,11-Didehydro-11-deoxy-6-O-methyl-erythromycin 2'-acetate 12-[bromoacetate]4"-(phenylmethyl carbonate) (Scheme 2, formula IX-2) was prepared as described in example 14A by replacing chloroacetic acid with bromoacetic acid.

B] (10E)-10,11-Didehydro-11-deoxy-6-O-methyl-erythromycin 2'-acetate 4"-(phenylmethyl carbonate)12-[cyanoacetate]; (IV-23):

To a solution of 50 mg (49 µmol) IX-2 dissolved in 0.5 ml CH$_2$Cl$_2$ was added a solution of 9.5 mg (60 µmol) tetraethylammonium cyanide in 0.5 ml CH$_2$Cl$_2$ at 0° C. over 30 minutes. The resulting mixture was stirred at 0° C. for 60 minutes and then concentrated to 0.5 ml. This solution was loaded onto a silica gel column and eluted with CH$_3$CN/CH$_2$Cl$_2$/NH$_4$OH 1:1:0.01. The appropriate fractions were combined and evaporated to give 34 mg (72%) of the desired product IV-23, contaminated with approx. 20% of already cyclized product V-23. $R_f$: 0.6 (CH$_3$CN/CH$_2$Cl$_2$/NH$_4$OH 1:1:0.01). $^1$H-NMR (CDCl$_3$), diagnostic signals only: 0.90 (t, 3H), 0.92 (d, 3H), 1.20 (s, 3H), 1.67 (s, 3H), 1.89 (s, 3H), 2.01 (s, 3H), 2.24 (s, 6H), 3.10 (s, 3H), 3.33 (s, 3H), 3.40 (s, 2H), 4.12 (broad d, 1H), 4.34 (m, 1H), 4.46 (d, 1H), 4.57 (d, 1H), 4.96 (dd, 1H), 4.98 (d, 1H), 5.13 (d, 1H), 5,27 (d, 1H), 5.71 (dd, 1H), 6.57 (s, 1H).

C] (3R or S,3aS,4R or S,6R,8R,9R,10S,11S,12R,15R,15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethylhexadecahydro-8-methoxy-4,6,8,10,12,15a-hexamethyl-2,5,13-trioxo-2H-furo[2,3-c]oxacyclotetradecin-3-carbonitrile; mixture of 2 diastereomers (V-23):

To a solution of 34 mg IV-23 in 1.0 ml benzene was added DBU (10.4 µl, 70 µmol) and the mixture was heated to reflux for 12 hours. The reaction mixture was cooled, diluted with CH$_2$Cl$_2$ and washed with 5% NaHCO$_3$ solution. The combined organic extracts were dried (MgSO$_4$) and evaporated to give a crude product that was purified by silica gel chromatography (5 g) using CH$_3$CN/MeOH/NH$_4$OH 1:1:0.01 as an eluent. The product V-23 was obtained as a colorless glass. Yield: 19 mg (56%), 4:1 mixture of two diastereomers. MS (ISP): 973.5 (MH$^+$).

D] (3R or S,3aS,4R or S,6R,8R,9R,10S,11S,12R,15R,15aS)-9-[[2-O-Acetyl-3,4,6-trideoxy-3-(dimethylamino)-β-D-xylo-hexopyranosyl]oxy]-15-ethylhexadecahydro-11-hydroxy-8-methoxy-4,6,8,10,12,15a-hexamethyl-2,5,13-trioxo-2H-furo[2,3-c]oxacyclotetradecin-3-carbonitrile; (VI-23):

Removal of the cladinose moiety was performed as described in example 1D using 118 mg (121 μmol) V-23. The desired product was obtained as a foam. Yield: 57 mg (69%). MS (ISP): 681.3 (MH$^+$). $^1$H-NMR (CDCl$_3$), diagnostic signals only: 0.89 (t, 3H), 0.97 (d, 3H), 1.03 (d, 3H), 1.10 (d, 3H), 1.24 (d, 3H), 1.28 (s, 3H), 1.29 (d, 3H), 1.51 (s, 3H), 2.07 (s, 3H), 2.27 (s, 6H), 3.02 (s, 3H), 3.18 (s, 1H), 3.42–3.58 (m, 2H), 3.74 (d, 1H), 4.62 (d, 1H), 4.76 (dd, 1H), 4.84 (s, 1H), 5.38 (dd, 1H).

E] (3R or S,3aS,4R or S,6R,8R,9R,10R,12R,15R,15aS)-9-[[2-O-Acetyl-3,4,6-trideoxy-3-(dimethylamino)-β-D-xylo-hexopyranosyl]oxy]-15-ethyltetradecahydro-8-methoxy-4,6,8,10,12,15a-hexamethyl-2,5,11,13-tetraoxo-2H-furo[2,3-c]oxacyclotetradecin-3-carbonitrile; (VII-23):

Oxidation was performed as described in example 1E with 57 mg VI-23 to give 23 mg (40%) of VII-23. R$_f$: 0.4 (CHCl$_3$MeOH/NH$_4$OH 9:1:0.1). $^1$H-NMR (CDCl$_3$), diagnostic signals only: 0.92 (t, 3H), 1.06 (d, 3H), 1.14 (d, 3H), 1.18 (d, 3H), 1.26 (d, 3H), 1.30 (s, 3H), 1.39 (d, 3H), 1.56 (s, 3H), 2.05 (s, 3H), 2.25 (s, 6H), 2.77 (s, 3H), 3.00–3.12 (m, 2H), 3.15 (s, 1H), 3.56 (m, 1H), 3.85 (q, 1H), 4.26 (d, 1H), 4.41 (d, 1H), 4.63 (s, 1H), 4.74 (dd, 1H), 5.26 (dd, 1H).

F] (3R,3aS,4R,6R,8R,9R,10R,12R,15R,15aS)-15-Ethyltetradecahydro-8-methoxy-4,6,8,10,12,15a-hexamethyl-2,5,11,13-tetraoxo-9-[[3,4,6-trideoxy-3-(dimethylamino)-β-D-xylo-hexopyranosyl]oxy]-2H-furo[2,3-c]oxacyclotetradecin-3-carbonitrile; (I-23):

Deprotection of 23 mg VII-23 was performed as described in example 1F to give product I-23 as a colorless glass. Yield 18 mg (83%). MS (ISP): 637.3 (MH$^+$). $^1$H-NMR (CDCl$_3$), diagnostic signals only: 0.92 (t, 3H), 1.06 (d, 3H), 1.13 (d, 3H), 1.25 (d, 3H), 1.29 (d, 3H), 1.30 (s, 3H), 1.40 (d, 3H), 1.56 (s, 3H), 2.27 (s, 6H), 2.77 (s, 3H), 3.01–3.24 (m, 4H), 3.58 (m, 2H), 3.87 (q, 1H), 4.26 (d, 1H), 4.34 (d, 1H), 4.60 (d, 1H), 5.26 (dd, 1H).

Scheme 6:

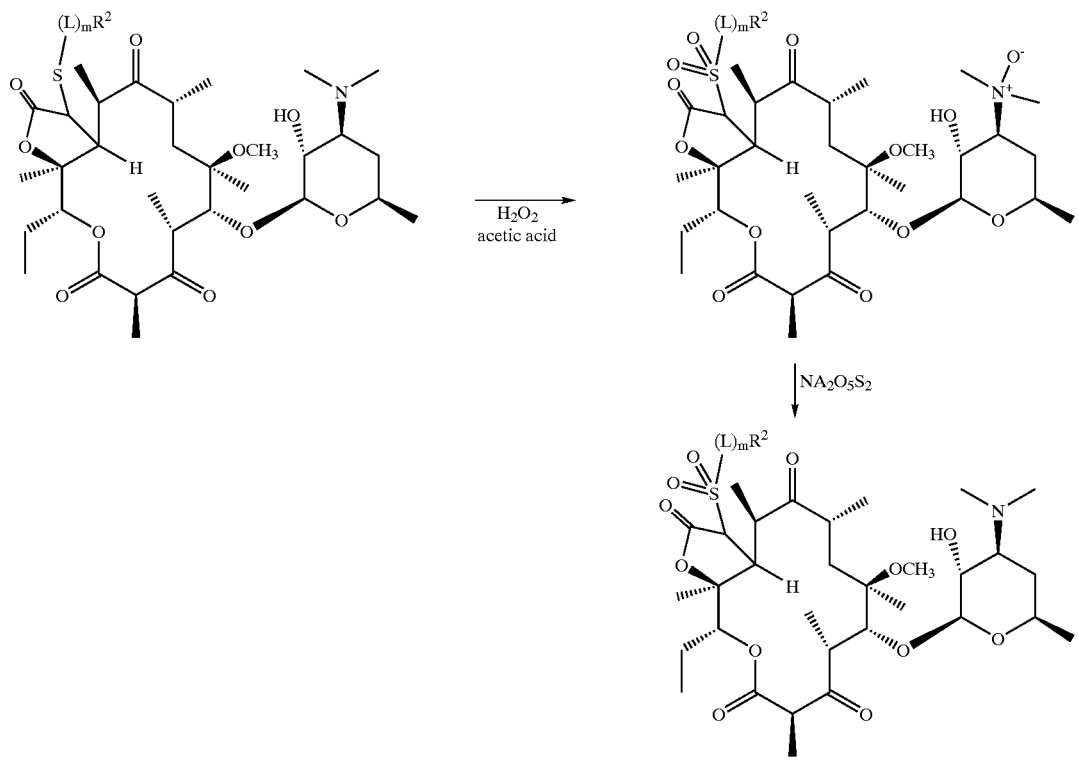

EXAMPLE 24

Preparation of (3S,3aR,4R,6R,8R,9R,10R,12R,15R,15aS)-15-Ethyloctahydro-8-methoxy-4,6,8,10,12,15a-hexamethyl-3-[(3-phenylpropyl)sulfonyl]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-24, Compound of Formula I, Where R$^1$ is [3-phenylpropyl]sulfonyl)

A] (3S,3aR,4R,6R,8R,9R,10R,12R,15R,15aS)-15-Ethyloctahydro-8-methoxy-4,6,8,10,12,15a-hexamethyl-3-[(3-phenylpropyl)sulfonyl]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-24):

Synthesis of this compound from sulfide I-2 (example 2) is outlined in Scheme 6, above. In a micro vial, 9.5 mg (12.5 μmol) I-2 was dissolved in acetic acid (500 μl) and 25 μl H$_2$O$_2$ were added. The mixture was stirred at 40° C. for 4 hours. Another 25 μl H$_2$O$_2$ were added and stirring was continued for 48 hours. The reaction mixture was poured into saturated NaHCO$_3$-solution and extracted with CH$_2$Cl$_2$. The combined organic extracts were dried over Na$_2$SO$_4$ and evaporated to give 8.5 mg of a glass. This was dissolved in CH$_2$Cl$_2$ (25 ml) and washed with diluted sodium pyrosulfite solution. The organic layer was dried (Na$_2$SO$_4$) and evaporated. The crude product was purified by flash chromatography (CHCl$_3$/MeOH/NH$_4$OH 9:1:0.1). The appropriate fractions were combined and evaporated to give 5.6 mg (57%) of a glass. MS (ISP): 794.4 (MH$^+$). $^1$H-NMR (CDCl$_3$), diagnostic signals only: 0.87 (t, 3H), 1.11 (2 overlapping d, 6H), 1.24 (d, 3H), 1.29 (s, 3H), 1.34 (d, 3H), 1.36 (d, 3H), 1.60 (s, 6H), 2.29 (s, 6H), 2.82 (s, 3H), 3.12–3.26 (m, 4H), 3.31 (s, 1H), 3.86 (q, 1H), 4.38 (m, 2H), 4.86 (s, 1H), 5.75 (dd, 1H), 7.18–7.36 (m, 5H).

EXAMPLE 25

Preparation of (3aR,4R,6R,8R,9R,10R,12R,15R,15aS)-15-Ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c]oxacyclotetradecin-2,5,11,13 (3H,6H,12H)-tetrone; (I-25, Compound of Formula I, Where R$^1$ is H)

A] (3aR,4R,6R,8R,9R,10R,12R,15R,15aS)-15-Ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-25):

To a solution of 20 mg (26.7 μmol) (I-1 (3S,3aR,4R,6R,8R,9R,10R,12R,15R,15aS)-15-Ethyloctahydro-8-methoxy-4,6,8,10,12,15a-hexamethyl-3-[[2-phenylethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone) in 1.0 ml ethyl acetate was added Raney nickel (previously washed successively with water, methanol and ethyl acetate). The mixture was stirred vigorously for 12 hours and filtered. Removal of the solvent gave a colorless solid. Yield: 15 mg (92%). MS (ISP): 612.3 (MH$^+$). $^1$H-NMR (CDCl$_3$), diagnostic signals only: 0.86 (t, 3H), 1.06 (d, 3H), 1.13 (d, 3H), 1.24 (d, 3H), 1.31 (s, 3H), 1.32 (d, 3H), 1.37 (d, 3H), 1.49 (s, 3H), 2.27 (s, 6H), 2.62 (s, 3H), 3.02 (broad q, 1H), 3.49 (broad s, 1H), 3.56 (m, 1H), 3.88 (q, 1H), 4.25 (d, 1H), 4.32 (d, 1H), 4.88 (dd, 1H).

EXAMPLE 26

Preparation of (3S,3aR,4R,6R,8R,9R,10R,12R,15R,15aS)-3-[[3-[6-Amino-9H-purine-9-yl]propyl]thio]-15-ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-26, Compound of Formula I, Where R$^1$ is [3-[6-amino-9H-purine-9-yl]propyl]thio)

This compound is prepared in analogy to compound I-14, Example 14; the side chain used for this macrolide is prepared from 9-(3-chloropropyl)-6-amino-9H-purine (J. Am. Chem. Soc. 1994, 116, 6089) according to Scheme 5.

MS (ISP): 819.4 (MH$^+$).

EXAMPLE 27

Preparation of (3S,3aR,4R,6R,8R,9R,10R,12R,15R,15aS)-3-[[2-[6-N,N-Dimethylamino-9H-purine-9-yl]ethyl]thio]-15-ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-27, Compound of Formula I, Where R$^1$ is [2-[6-N,N-dimethylamino-9H-purine-9-yl]ethyl]thio).

This compound is prepared in analogy to compound I-14, Example 14; the side chain used for this macrolide is prepared from 6-dimethylaminopurine according to Scheme 5.

MS (ISP): 833.5 (MH$^+$).

EXAMPLE 28

Preparation of I-28, Compound of Formula I, Where R$^1$ is [3-[2,4-1H,3H-pyrimidinedione-1-yl]propyl]thio.

A] 1-(3-chloropropyl)-2,4-1H,3H-pyrimidinedione

Uracil (11.2 g, 99.9 mmol) was dissolved in acetonitrile (150 ml) and N,O-bis(trimethylsilyl)-acetamide (55.2 ml, 219.8 mmol) was added. The reaction mixture was stirred over night at room temperature and subsequently the solvent was evaporated under reduced pressure. Now 1-bromo-3-chloropropane (178.9 ml, 1.82 mol) was added and the mixture was stirred at room temperature. After 6 days water was added to the reaction and the emulsion was extracted with CH$_2$Cl$_2$. The organic layer was dried over Na$_2$SO$_4$ and partially evaporated in vacuo. Upon addition of hexane the product precipitated. MS (ISP): 189.2 (MH$^+$). $^1$H-NMR (DMSO-d6): 2.04 (m, 2H), 3.65 (t, 2H), 3.78 (t, 2H), 5.55 (d, 1H), 7.61 (d, 1H) 11.23 (broad s, 1H).

EXAMPLE 29

Preparation of I-29, Compound of Formula I, Where R$^1$ is [3-[5-methyl-2,4-1H,3H-pyrimidinedione-1-yl]propyl]thio.

A] 1-(3-chloropropyl)-5-methyl-2,4-1H,3H-pyrimidinedione 1-(3-chloropropyl)-5-methyl-2,4-1H,3H-pyrimidinedione was prepared according to example 28 step A from thymine. MS (ISP): 189.2 (MH$^+$). $^1$H-NMR (DMSO-d6): 1.75 (s, 3H), 2.04 (m, 2H), 3.65 (t, 2H), 3.75 (t, 2H), 7.49 (s, 1H), 11.22 (s, 1H).

The title compound (I-29) was prepared according to example 14 steps D–K starting from 1-(3-chloropropyl)-5-methyl-2,4-1H,3H-pyrimidinedione and IX-1. MS (ISP): 796.4 (MH$^+$). $^1$H-NMR (CDCl$_3$), diagnostic signals only: 0.89 (t, 3H), 1.12 (d, 3H), 1.15 (d, 3H), 1.24 (d, 3H), 1.32 (s, 3H), 1.33 (d, 3H), 1.38 (d, 3H), 1.52 (s, 3H), 1.93 (s, 3H), 2.10–2.18 (m, 2H), 2.26 (s, 6H), 2.45 (m, 1H), 2.51–2.60 (m 1H), 2.61 (s, 1H), 2.78 (s, 3H), 3.02–3.21 (m, 4H), 3.48 (broad s, 1H), 3.51–3.61 (m, 1H), 3.77–3.98 (m, 3H), 4.23 (s, 1H), 4.28 (d, 1H), 4.33 (d, 1H), 5.41 (dd, 1H), 7.45 (s, 1H), 7.95 (broad, 1H).

EXAMPLE 30

Preparation of I-30, Compound of Formula I, Where R$^1$ is [3-[4-(4-methoxyphenyl)-1H-pyrazol-1-yl]propyl]thio.

A] 1-(3-chloropropyl)-4-iodo-1H-pyrazole

4-Iodopyrazole (6.0 g, 30.9 mmol) was dissolved in DMF (50 ml) and KO$^t$Bu (3.64 g, 32.5 mmol) was added. The mixture was stirred at room temperature for 1 hour and subsequently 1-bromo-3-chloropropane (3.14 ml, 32.5 mmol) was added. A white precipitate formed. The reaction mixture was poured into water and extracted twice with hexane. The combined organic layers were dried over MgSO$_4$. The solvent was removed in vacuo to give 7.32 g of a colorless liquid. The compound was used without further purification.

MS (EI): 208.1, 270.1 (M$^+$, 73%), 272.1 (M$^+$, 23%). $^1$H-NMR (CDCl$_3$): 2.30 (m, 2H), 3.47 (t, 2H), 4.32 (t, 2H), 7.48 (s, 1H), 7.53 (s, 1H).

B] 1-(3-chloropropyl)-4-(4-methoxyphenyl)-1H-pyrazole 1-(3-chloropropyl)-4-iodo-1H-pyrazole (508 mg, 1.88 mmol) was dissolved in dioxane (10 ml) and 4-methoxyphenylboronic acid (423 mg, 2.78 mmol), tetrakis (triphenylphosphine)-palladium(0) (106.8 mg, 0.092 mmol) and 3 ml of aqueous $K_3PO_4$ (2M) were added to the solution. This mixture was degassed and heated under argon for 2 hours to 60° C. The reaction mixture was then poured into water (100 ml) and extracted twice with ethyl acetate. The combined organic layers were dried over $Na_2SO_4$ and evaporated under reduced pressure. The residue was purified by flash chromatography (silica gel, gradient of 30% to 50% of ethyl acetate in hexane) to give the desired compound (370 mg) as a yellow solid. MS (EI): 250.2 ($M^+$, 100%), 252.2 ($M^+$, 30%). $^1$H-NMR (CDCl$_3$): 2.35 (m, 2H), 3.52 (t, 2H), 3.82 (s, 3H), 4.33 (t, 2H), 6.91 (m, 2H), 7.40 (m, 2H), 7.60 (s, 1H), 7.73 (s, 1H).

The title compound (I-30) was prepared according to example 14 steps D–K from 1-(3-chloropropyl)-4-(4-methoxyphenyl)-1H-pyrazole and IX-1. MS (ISP): 858.5 ($MH^+$). $^1$H-NMR (CDCl$_3$), diagnostic signals only: 0.89 (t, 3H), 1.11 (d, 3H), 1.14 (d, 3H), 1.24 (d, 3H), 1.33 (d, 3H), 1.33 (s, 3H), 1.38 (d, 3H), 1.51 (s, 3H), 1.89–2.00 (m, 1H), 2.26 (s, 6H), 2.33 (m, 2H), 2.46 (m, 1H), 2.52–2.63 (m, 1H), 2.62 (s, 1H), 2.65–2.74 (m, 1H), 2.81 (s, 3H), 3.05–3.22 (m, 4H), 3.48 (broad s, 1H), 3.55 (m, 1H), 3.82 (s, 3H), 3.86 (q, 1H), 4.25 (s, 1H), 4.28 (d, 1H), 4.30–4.38 (m, 3H), 5.45 (dd, 1H), 6.89 (d, 2H), 7.41 (d, 2H), 7.70 (s, 1H), 7.72 (s, 1H).

EXAMPLE 31

Preparation of I-31, Compound of Formula I, Where $R^1$ is [3-[4-(4-acetylphenyl)-1H-pyrazol-1-yl]propyl]thio.

A] 1-(3-chloropropyl)-4-(4-acetylphenyl)-1H-pyrazole 1-(3-chloropropyl)-4-(4-acetylphenyl)-1H-pyrazole was prepared according to example 30 steps A and B using 4-acetylphenylboronic acid instead of 4-methoxyphenylboronic acid. MS (EI): 262.2 ($M^+$, 100%), 264.2 ($M^+$, 30%). $^1$H-NMR (CDCl$_3$): 2.37 (m, 2H), 2.61 (s, 3H), 3.52 (t, 2H), 4.37 (t, 2H), 7.56 (d, 2H), 7.77 (s, 1H), 7.87 (s, 1H), 7.96 (d, 2H).

The title compound (I-31) was prepared according to example 14 steps D–K from 1-(3-chloropropyl)-4-(4-acetylphenyl)-1H-pyrazole and IX-1. MS (ISP): 870.5 ($MH^+$). $^1$H-NMR (CDCl$_3$), diagnostic signals only: 0.89 (t, 3H), 1.11 (d, 3H), 1.15 (d, 3H), 1.24 (d, 3H), 1.33 (s, 3H), 1.38 (d, 3H), 1.51 (s, 3H), 2.28 (s, 6H), 2.42–2.52 (m, 1H), 2.60 (s, 3H), 2.82 (s, 3H), 2.99–3.23 (m, 4H), 3.45–3.60 (m, 2H), 3.86 (q, 1H), 4.22–4.42 (m, 5H), 5.45 (dd, 1H), 7.59 (d, 2H), 7.85 (s, 1H), 7.91–7.98 (m, 3H).

EXAMPLE 32

Preparation of (3S,3aR,4R,6R,8R,9R,10R,12R,15R,15aS)-3-[[4-[6-Amino-9H-purine-9-yl]butyl]thio]-15-ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-32, Compound of Formula I, Where $R^1$ is [4-[6-amino-9H-purine-9-yl]butyl]thio)

32D

Ethanethioic acid, S-[[6-amino-9H-purine-9-yl]butyl] ester was obtained according to example 14D from 9-(bromobutyl)-6-amino-9H-purine (J. Chem. Soc. Perkin Trans. 2, 1998, 1455–1462) and potassium thioacetate. MS (EI): 265.1 ($M^+$, 5%), 222.1 (100%).

32E

[6-amino-9H-purine]-1-butanethiol was obtained according to example 14E from Ethanethioic acid, S-[[6-amino-9H-purine-9-yl]butyl]ester. MS (ISP): 224.2 ($MH^+$).

32F (10E)-10,11-didehydro-11-deoxy-6-O-methyl-erythromycin 2'-acetate 12-[[[4-[6-amino-9H-purine-9-yl]butyl]thio]acetate] 4"-(phenylmethyl carbonate) IV-32 was obtained according to example 14F from (10E)-10,11-Didehydro-11-deoxy-6-O-methyl-erythromycin 2'-acetate 12-[chloroacetate] 4"-(phenylmethyl carbonate) (Scheme 2, formula IX-1) and [6-amino-9H-purine]-1-butanethiol. MS (ISP): 1169.6 ($MH^+$), 585.7 ($[MH2]^{++}$)

32G (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-3-[[4-[6-amino-9H-purine-9-yl]butyl]thio]-11-[[2,6-dideoxy-3-C-methyl-3-O-methyl-4-O-[(phenylmethoxy)-carbonyl]-α-L-ribo-hexopyranosyl]oxy]-15-ethyldecahydro-8-methoxy-4,6,8,10,12,15a-hexamethyl-2H-furo[2,3-c]oxacyclotetradecin-2,5,13(3H,6H)-trione; (V-32) was obtained according to example 6E by cyclisation of IV-32. MS (ISP): 1169.6 ($MH^+$), 585.4 ($[MH_2]^{++}$).

32H (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-3-[[4-[6-amino-9H-purine-9-yl]butyl]thio]-15-ethyldecahydro-11-hydroxy-8-methoxy-4,6,8,10,12,15a-hexamethyl-2H-furo[2,3-c]oxacyclotetradecin-2,5,13(3H,6H)-trione; (VI-32) was obtained from V-32 according to example 1D. MS (ISP): 877.4 ($MH^+$), 439.6 ($[MH_2]^{++}$).

32I (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-3-[[4-[6-amino-9H-purine-9-yl]butyl]thio]-15-ethyloctahydro-8-methoxy-4,6,8,10,12,15a-hexamethyl-2H-furo[2,3-c]oxacyclotetradecin-2,5,11,13(3H,6H,12H)-tetrone; (VII-32):

To a solution of 106 mg (121 μmol) VI-32 in 3.5 ml $CH_2Cl_2$ under argon was added dropwise 1.1 g of a 15 wt % solution of (1,1,1-triacetoxy)-1,1-dihydro-1,2-benziodoxol-3(1H)one (Dess-Martin reagent) in $CH_2Cl_2$ over 15 minutes. The resulting yellow solution was stirred for 3 hours. After dilution with 1.2 ml of diethylether, the mixture was then poured into 10 ml of 10% $Na_2S_2O_3$ and 1 ml of saturated $NaHCO_3$ solution and stirred for 1 hour. The mixture was extracted three times with 20 ml ether. The organic phases were washed successively with 20 ml 5% $NaHCO_3$, 20 ml water and 20 ml brine, dried over $Na_2SO_4$ and evaporated. Flash chromatography with $MeCl_2$/MeOH/$NH_3$ on silica gel gave the protected ketolide VII-32 as a mixture of two diastereomers in quantitative yield. MS (ISP): 875.4 ($MH^+$).

32K (3S,3aR,4R,6R,8R,9R,10R,12R,15R,15aS)-3-[[4-[6-Amino-9H-purine-9-yl]butyl]thio]-15-ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-32) was obtained from VII-32 according to example 1F. MS (ISP): 833.4 (MH$^+$), 417.5 ([MH$_2$]$^{++}$). $^1$H-NMR (CDCl$_3$) diagnostic signals only: 0.86 (t, 3H), 1.16 (2×d, 6H), 1.26 (d, 3H), 1.32 (d, 3H), 1.34 (d, 3H), 1.38 (s, 3H), 1.53 (s, 3H), 1.58–1.84 (m, 6H), 2.21–1.88 (m, 3 H), 2.26 (s, 6H), 2.46 (m, 1H), 2.62–2.54 (m, 1 H), 2.63 (s, 1H), 2.75 (s, 3H), 2.78–2.73 (m, 1H), 3.05–3.24 (m, 4H), 3.48 (broad s, 1H), 3.62–3.51 (m, 1H), 3.84 (q, 1H), 4.20–4.32 (m, 4H), 4.35 (d, 1H), 5.46 (s, 2H), 5.48 (dd, 1H), 7.91 (s, 1H), 8.36 (s, 1H).

EXAMPLE 33

Preparation of (3S,3aR,4R,6R,8R,9R,10R,12R,15R,15aS)-3-[[2-[4-Amino-pyrazolo[3,4-d]pyrimidin-1-yl]ethyl]thio]-15-ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-33, Compound of Formula I, Where R$^1$ is [2-[4-amino-pyrazolo[3,4-d]pyrimidin-1-yl]ethyl]thio)

33C 4-amino-1-(2-chloroethyl)-1H-Pyrazolo[3,4-d]pyrimidine was prepared according to example 14c from 2-(4-amino-pyrazolo[3,4-d]pyrimidin-1-yl)-ethanol (*J. Org. Chem.* 1956, 21, 1240–1252). MS (EI): 197.2 (M$^+$, 41%), 148.2 (19%), 135.2 (100%).

33D

Ethanethioic acid, S-[[4-amino-pyrazolo[3,4-d]pyrimidin-1-yl]ethyl]ester was obtained according to example 14D from 4-amino-1-(2-chloroethyl)-1H-pyrazolo[3,4-d]pyrimidine and potassium thioacetate. MS (EI): 237.1 (M$^+$), 194.2 (100%).

33E 2-(4-Amino-pyrazolo[3,4-d]pyrimidin-1-yl)-ethanethiol was obtained according to example 14E from Ethanethioic acid, S-[[4-amino-pyrazolo[3,4-d]pyrimidin-1-yl]ethyl] ester. MS (EI): 196.2 (MH$^+$100%).

33F (10E)-10,11-didehydro-11-deoxy-6-O-methyl-erythromycin 2'-acetate 12-[[[2-[4-Amino-Pyrazolo[3,4-d]pyrimidin-1-yl]ethyl]thio]acetate]4"-(phenylmethyl carbonate) IV-33 was obtained according to example 14F from (10E)-10,11-Didehydro-11-deoxy-6-O-methyl-erythromycin 2'-acetate 12-[chloroacetate] 4"-(phenylmethyl carbonate) (Scheme 2, formula IX-1) and 2-(4-amino-pyrazolo[3,4-d]pyrimidin-1-yl)-ethanethiol. MS (ISP): 1141.5 (MH$^+$), 571.6([MH2]$^{++}$)

33G (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-3-[[2-[4-amino-pyrazolo[3,4-d]pyrimidin-1-yl]ethyl]thio]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-2H-furo[2,3-c]oxacyclotetradecin-2,5,13(3H,6H)-trione; (V-33) was obtained according to example 6E by cyclisation of IV-33. MS (ISP): 1141.5 (MH$^+$), 571.6 ([MH$_2$]$^{++}$).

33H (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-3-[[2-[4-amino-pyrazolo[3,4-d]pyrimidin-1-yl]ethyl]thio]-15-ethyldecahydro-11-hydroxy-8-methoxy-4,6,8,10,12,15a-hexamethyl-2H-furo[2,3-c]oxacyclotetradecin-2,5,13(3H,6H)-trione; (VI-33) was obtained from V-33 according to example 1D. MS (ISP): 849.4 (MH$^+$), 425.6 ([MH$_2$]$^{++}$).

33I (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-3-[[2-[4-amino-pyrazolo[3,4-d]pyrimidin-1-yl]ethyl]thio]-15-ethyloctahydro-8-methoxy-4,6,8,10,12,15a-hexamethyl-2H-furo[2,3-c]oxacyclotetradecin-2,5,11,13(3H,6H,12H)-tetrone; (VII-33) according to example 32I.MS (ISP): 847.4 (MH$^+$).

33K (3S,3aR,4R,6R,8R,9R,10R,12R,15R,15aS)-3-[[2-[4-amino-pyrazolo[3,4-d]pyrimidin-1-yl]ethyl]thio]-15-ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-33) was obtained from VII-33 according to example 1F. MS (ISP): 805.4 (MH$^+$), 403.6 ([MH$_2$]$^{++}$). $^1$H-NMR (CDCl$_3$) diagnostic signals only: 0.86 (t, 3H), 1.16 (d, 3H), 1.17 (d, 3H), 1.26 (d, 3H), 1.32 (d, 3H), 1.33 (d, 3H), 1.38 (s, 3H), 1.53 (s, 3H), 2.26 (s, 6H), 2.45 (m, 1H), 2.62 (s, 1H), 2.66 (s, 3H), 3.05–3.25 (m, 4H), 3.42–3.65 (m, 4H), 3.84 (q, 1H), 4.29 (d, 1H), 4.25–4.32 (m, 1H), 4.34 (d, 1H), 4.39 (s, 1H), 4.61–4.75 (m, 3H), 5.42 (dd, 1H), 5.38 (s, 2H), 7.92 (s, 1H), 8.38 (s, 1H).

EXAMPLE 34

Preparation of (3S,3aR,4R,6R,8R,9R,10R,12R,15R,15aS)-3-[[2-[2,6-diamino-9H-purine-9-yl]ethyl]thio]-15-ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-34, Compound of Formula I, Where R$^1$ is [2-[2,6-diamino-9H-purine-9-yl]ethyl]thio)

34D

Ethanethioic acid, S-[[2,6-diamino-9H-purine-9-yl]ethyl] ester was obtained according to example 14D from 9-(2-bromoethyl)-2,6-diamino-9H-purine (J. Amer. Chem. Soc. 1993, 115, 9952–9959). MS (ISP): 253.1 (MH$^+$).

34E

[2,6-diamino-9H-purine]-1-ethanethiol was obtained according to example 14E from Ethanethioic acid, S-[[2,6-diamino-9H-purine-9-yl]ethyl]ester. MS (EI): 211.2 (MH$^+$).

34F (10E)-10,11-didehydro-11-deoxy-6-O-methyl-erythromycin 2'-acetate 12-[[[2-[2,6-diamino-9H-purine-9-yl]ethyl]thio]acetate] 4"-(phenylmethyl carbonate) IV-34 was obtained according to example 14F from (10E)-10,11-Didehydro-11-deoxy-6-O-methyl-erythromycin 2'-acetate 12-[chloroacetate] 4"-(phenylmethyl carbonate) (Scheme 2, formula IX-1) and [2,6-diamino-9H-purine]-1-ethanethiol. MS (ISP): 1156.6 (MH$^+$), 578.9 ([MH2]$^{++}$)

34G (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-3-[[2-[2,6-diamino-9H-purine-9-yl]ethyl]thio]-11-[[2,6-dideoxy-3-C-methyl-3-O-methyl-4-O-[(phenylmethoxy)-carbonyl]-α-L-ribo-hexopyranosyl]oxy]-15-ethyldecahydro-8-methoxy-4,6,8,10,12,15a-hexamethyl-2H-furo[2,3-c]oxacyclotetradecin-2,5,13(3H,6H)-trione; (V-34) was obtained according to example 6E by cyclisation of IV-34. MS (ISP): 1156.6 (MH$^+$), 578.9 ([MH$_2$]$^{++}$).

34H (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-3-[[2-[2,6-diamino-9H-purine-9-yl]ethyl]thio]-15-ethyldecahydro-11-hydroxy-8-methoxy-4,6,8,10,12,15a-hexamethyl-2H-furo[2,3-c]oxacyclotetradecin-2,5,13(3H,6H)-trione; (VI-34) was obtained from V-34 according to example 1D. MS (ISP): 864.5 (MH$^+$), 433.0 ([MH$_2$]$^{++}$).

34I (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-3-[[2-[2,6-diamino-9H-purine-9-yl]ethyl]thio]-15-ethyloctahydro-8-methoxy-4,6,8,10,12,15a-hexamethyl-2H-furo[2,3-c]oxacyclotetradecin-2,5,11,13(3H,6H,12H)-tetrone; (VII-34) was obtained from VI-34 according to example 32I. MS (ISP): 862.5 (MH$^+$), 431.8 ([MH$_2$]$^{++}$).

34K (3S,3aR,4R,6R,8R,9R,10R,12R,15R,15aS)-3-[[2-[2,6-diamino-9H-purine-9-yl]ethyl]thio]-15-ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-34) was obtained from VII-34 according to example 1F. MS (ISP): 820.5 (MH$^+$), 411.2 ([MH$_2$]$^{++}$). $^1$H-NMR (CDCl$_3$) diagnostic signals only: 0.86 (t, 3H), 1.16 (2xd, 6H), 1.26 (d, 3H), 1.32 (d, 3H), 1.34 (d, 3H), 1.38 (s, 3H), 1.53 (s, 3H), 1.58–1.84 (m, 2H), 2.01–1.88 (m, 2H), 2.39 (s, 6H), 2.62–2.54 (m, 2 H), 2.71 (s, 3H), 3.08–3.22 (m, 4H), 3.31 (m, 2H), 3.48 (broad s, 1H), 3.62–3.51 (m, 2H), 3.85 (q, 1H), 4.31 (d, 1H), 4.30–4.52 (m, 3H), 4.68 (broad s, 2H), 5.42 (dd, 1H), 5.55(broad s, 2H), 7.91 (s, 1H).

EXAMPLE 35

Preparation of (3S,3aR,4R,6R,8R,9R,10R,12R,15R,15aS)-15-Ethyloctahydro-8-methoxy-4,6,8,10,12,15a-hexamethyl-3-[[3-[3-(3-pyridinyl)-1H-pyrazol-1-yl]propyl]thio]-9-[[3,4,6-trideoxy-3-(dimethylamino)-β-D-xylo-hexopyranosyl]oxy]-2H-furo[2,3-c]oxacydotetradecin-2,5,11,13(3H,6H,12H)-tetrone; (I-35, Compound of Formula I, Where R$^1$ is [3-[3-(3-pyridinyl)-1H-pyrazol-1-yl]propyl]thio)

35C 1-(3-chloropropyl)-3-(3-pyridinyl)-1H-pyrazole was obtained as a colourless oil from 3-(3-pyridinyl)-1H-pyrazole (Arch. Pharmaz. 1973, 306, 934), 3-bromo-1-chloropropane and potassium t-butoxide in DMF at room temperature. MS (EI): 222.2 (MH$^+$, 100%).

35D

Ethanethioic acid, S-[3-[3-(3-pyridinyl)-1H-pyrazol-1-yl]propyl]ester: According to example 14D from 1-(3-chloropropyl)-3-(3-pyridyl)-1H-pyrazole and potassium thioacetate. MS (EI): 262.1 (MH$^+$, 100%).

35E

[3-(3-pyridinyl)-1H-pyrazole]-1-propanethiol was obtained according to example 14E from ethanethioic acid, S-[3-[3-(3-pyridyl)-1H-pyrazol-1-yl]propyl]ester. MS (EI): 219.2 (M$^+$, 57%), 158.2 (100%).

35F (10E)-10,11-Didehydro-11-deoxy-6-O-methyl-erythromycin 2'-acetate 4"-(phenylmethyl carbonate)12-[[[3-[3-(3-pyridinyl)-1H-pyrazol-1-yl]propyl]thio]acetate] 4"-(phenylmethyl carbonate); (IV-35) was obtained according to example 14F from IX-1 and [3-(3-pyridinyl)-1H-pyrazole]propanethiol. MS (ISP): 1166.0 (MH$^+$), 584.4 ([MH$_2$]$^{++}$).

35G (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyl-decahydro-8-methoxy-4,6,8,10,12,15a-hexamethyl-3-[[3-[3-(3-pyridinyl)-1H-pyrazol-1-yl]propyl]thio]-2H-furo[2,3-c]oxacyclotetradecin-2,5,13(3H,6H)-trione; (V-35) was prepared according to example 6E by cyclisation of IV-35. MS (ISP): 1165.5 (MH$^+$), 583.4 ([MH$_2$]$^{++}$).

35H (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[[3-[3-(3-pyridinyl)-1H-pyrazol-1-yl]propyl]thio]-2H-furo[2,3-c]oxacyclotetradecin-2,5,13(3H,6H)-trione; (VI-35) was prepared according to example 1D from V-35. MS (ISP): 873.4 (MH$^+$), 437.6 ([MH$_2$]$^{++}$).

35I (3S,3aR,4R,6R,8R,9R,10R,12R,15R,15aS)-9-[[2-O-Acetyl-3,4,6-trideoxy-3-(dimethylamino)-β-D-xylohexopyranosyl]oxy]-15-ethyloctahydro-8-methoxy-4,6,8,
10,12,15a-hexamethyl-3-[[3-[3-(3-pyridinyl)-1H-pyrazol-1-
yl]propyl]thio]-2H-furo[2,3-c]oxacyclotetradecin-2,5,11,13
(3H,6H,12H)-tetrone; (VII-35) was obtained from VI-35
according to example 33E. MS (ISP): 871.4 (MH$^+$), 436.2
([MH$_2$]$^{++}$).

35K (3S,3aR,4R,6R,8R,9R,10R,12R,15R,15aS)-15-
Ethyloctahydro-8-methoxy-4,6,8,10,12,15a-hexamethyl-3-
[[3-[3-(3-pyridinyl)-1H-pyrazol-1-yl]propyl]thio]-9-[[3,4,6-
trideoxy-3-(dimethylamino)-β-D-xylo-hexopyranosyl]oxy]-
2H-furo[2,3-c]oxacyclotetradecin-2,5,11,13(3H,6H,12H)-
tetrone; (I-35) was prepared according to example 1F. MS
(ISP): 829.5 (MH$^+$), 415.7 ([MH$_2$]$^{++}$). $^1$H-NMR (CDCl3)
diagnostic signals only: 0.89 (t, 3H), 1.15 (2d, 6H), 1.27 (d,
3H), 1.32 (d, 3H), 1.33 (s, 3H), 1.34 (d, 3H), 1.52 (s, 3H),
2.25 (s, 6H), 2.63 (s, 1H), 2.65 (s, 3H), 3.86 (q, 1H), 4.28 (s,
1H), 4.30 (m, 5H), 5.46 (dd, 1H), 6.56 (d, 1H), 7.29 (m, 1H),
7.78 (d, 1H), 8.08 (m, 1H), 8.52 (m, 1H), 8.99 (d, 1H).

EXAMPLE 36

Preparation of (3S,3aR,4R,6R,8R,9R,10R,12R,15R,15aS)-
3-[[2-[3H-imidazo[4,5-b]pyridin-3-yl]ethyl]thio]-15-
ethyloctahydro-8-methoxy-4,6,8,10,12,15a-hexamethyl-9-
[[3,4,6-trideoxy-3-(dimethylamino)-β-D-xylo-
hexopyranosyl]oxy]-2H-furo[2,3-c]oxacyclotetradecin-2,5,
11,13(3H,6H,12H)-tetrone; (I-36), Compound of Formula I,
Where R$^1$ is [2-[3H-imidazolo[4.5-b]pyridinyl-3-ethyl]thio)

36B 2-(3H-imidazo[4,5-b]pyridin-3-yl)-ethanol was prepared
according to example 14b from 1H-imidazo[4,5-b]pyridine
and ethylene carbonate. MS (EI): 163.2 (M$^+$, 43%), 132.1
(58%), 119.1 (100%).

36C 3-(2-Chloro-ethyl)-3H-imidazo[4,5-b]pyridine was prepared
according to example 14c from 2(3H-imidazo[4,5-b]
pyridin-3-yl)-ethanol. MS (ISP): 181.6 (MH$^+$).

36D

Ethanethioic acid, S-[[2-imidazo[4,5-b]pyridin-3-yl]-
ethyl]ester was obtained according to example 14D from
3-(2-Chloro-ethyl)-3H-imidazo[4,5-b]pyridine and potassium thioacetate. MS (EI): 222.2 (M$^+$, 100%).

36E

2-Imidazo[4,5-b]pyridin-3-yl-ethanethiol was obtained
according to example 14E from Ethanethioic acid, S-[[2-
imidazo[4,5-b]pyridin-3-yl]-ethyl]ester. MS (EI): 179.2
(MH$^+$, 56%), 146.2 (54%), 120.2 (100%).

36F (10E)-10,11-didehydro-11-deoxy-6-O-methyl-
erythromycin 2'-acetate 12-[[[2-[3H-imidazo[4,5-b]pyridin-
3-yl]ethyl]thio]acetate] 4"-(phenylmethyl carbonate) IV-36
was obtained according to example 14F from (10E)-10,11-
Didehydro-11-deoxy-6-O-methyl-erythromycin 2'-acetate
12-[chloroacetate] 4"-(phenylmethyl carbonate) (Scheme 2,
formula IX-1) and 2-Imidazo[4,5-b]pyridin-3-yl-
ethanethiol. MS (ISP): 1125.6 (MH$^+$), 567.7([MH2]$^{++}$).

36G (3S,3aR,4R,6R,8R,9R,10S,11S,12R,15R,15aS)-9-[[2-O-
Acetyl-3,4,6-trideoxy-3-(dimethylamino)-β-D-xylo-
hexopyranosyl]oxy]-3-[[2-[-[3H-imidazo[4,5-b]pyridin-3-
yl]ethyl]thio]-11-[[2,6-dideoxy-3-C-methyl-3-O-methyl-4-
O-[(phenylmethoxy)carbonyl]-α-L-ribo-hexopyranosyl]
oxy]-15-ethyldecahydro-8-methoxy-4,6,8,10,12,15a-
hexamethyl-2H-furo[2,3-c]oxacyclotetradecin-2,5,13 (3H,
6H)-trione; (V-36) was obtained according to example 6E by
cyclisation of IV-36. MS (ISP): 1125.6 (MH$^+$), 563.6
([MH$_2$]$^{++}$).

36H (3S,3aR,4R,6R,8R,9R,10S,11S,12R,15R,15aS)-9-[[2-O-
Acetyl-3,4,6-trideoxy-3-(dimethylamino)-β-D-xylo-
hexopyranosyl]oxy]-3-[[2-[3H-imidazo[4,5-b]pyridin-3-yl]
thio]-15-ethyldecahydro-11-hydroxy-8-methoxy-4,6,8,10,
12,15a-hexamethyl-2H-furo[2,3-c]oxacyclotetradecin-2,5,
13(3H,6H)-trione; (VI-36) was obtained from V-36
according to example 1D. MS (ISP): 833.4 (MH$^+$), 417.3
([MH$_2$]$^{++}$).

36I (3S,3aR,4R,6R,8R,9R,10R,12R,15R,15aS)-9-[[2-O-
Acetyl-3,4,6-trideoxy-3-(dimethylamino)-β-D-xylo-
hexopyranosyl]oxy]-3-[[2-[3H-imidazo[4,5-b]pyridin-3-yl]
ethyl]thio]-15-ethyloctahydro-8-methoxy-4,6,8,10,12,15a-
hexamethyl-2H-furo[2,3-c]oxacyclotetradecin-2,5,11,13
(3H,6H,12H)-tetrone; (VII-36) was obtained from VI-36
according to example 32I.MS (ISP): 831.5 (MH$^+$), 416.4
([MH$_2$]$^{++}$).

36K (3S,3aR,4R,6R,8R,9R,10R,12R,15R,15aS)-3-[[2-[3H-
imidazo[4,5-b]pyridin-3-yl]ethyl]thio]-15-ethyloctahydro-
8-methoxy-4,6,8,10,12,15a-hexamethyl-9-[[3,4,6-trideoxy-
3-(dimethylamino)-β-D-xylo-hexopyranosyl]oxy]-2H-furo
[2,3-c] oxacyclotetradecin-2,5,11,13(3H,6H,12H)-tetrone;
(I-36) was obtained from VII-36 according to example 1F.
MS (ISP): 789.3 (MH$^+$), 395.7 ([MH$_2$]$^{++}$). $^1$H-NMR
(CDCl$_3$) diagnostic signals only: 0.87(t, 3H), 1.16 (d, 3H),
1.17 (d, 3H), 1.26 (d, 3H), 1.32 (d, 3H), 1.33 (d, 3H), 1.38
(s, 3H), 1.53 (s, 3H), 2.26 (s, 6H), 2.40–2.50 (m, 1H), 2.62
(s, 1H), 2.66 (s, 3H), 3.05–3.25 (m, 4H), 3.42–3.65 (m, 3H),
3.84 (q, 1H), 4.28 (d, 1H), 4.34 (d, 1H), 4.42 (s, 1H),
4.55–4.64 (m, 1H), 4.81 (dt, 1H), 5.40 (dd, 1H), 7.21 (dd,
1H), 8.03 (dd, 1H), 8.35 (dd, 1H), 8.49 (s, 1H).

EXAMPLE 37

Preparation of (3S,3aR,4R,6R,8R,9R,10R,12R,15R,15aS)-
3-[3-[3H-imidazo[4,5-b]pyridin-3-yl]propyl]-1-thio]-15-
ethyloctahydro-8-methoxy-4,6,8,10,12,15a-hexamethyl-9-
[[3,4,6-trideoxy-3-(dimethylamino)-β-D-xylo-
hexopyranosyl]oxy]-2H-furo[2,3-c) oxacyclotetradecin-2,5,
11,13(3H,6H,12H)-tetrone; (I-37), Compound of Formula I,
Where R$^1$ is [3-[3H-imidazolo[4.5-b]pyridinyl-3-propyl]
thio)

37D

Ethanethioic acid, S-[[3-imidazo[4,5-b]pyridin-3-yl]-
propyl]ester was obtained according to example 14D from 3-(3-Chloro-propyl)-3H-imidazo[4,5-b]pyridine. (Eur. Pat. Appl. EP 393574 (1990)) and potassium thioacetate. MS (ISP): 236.2 (MH⁺).

37E

3-Imidazo[4,5-b]pyridin-3-yl-propane-1-thiol was obtained according to example 14E from Ethanethioic acid, S-[[2-imidazo[4,5-b]pyridin-3-yl]-propyl]ester. MS (EI): 193.1 (M⁺, 52%), 146.2 (95%), 133.2 (100%).

37F (10E)-10,11-didehydro-11-deoxy-6-O-methyl-erythromycin 2'-acetate 12-[[[3-[3H-imidazo[4,5-b]pyridin-3-yl]propyl]thio]acetate] 4"-(phenylmethyl carbonate) IV-37 was obtained according to example 14F from (10E)-10,11-Didehydro-11-deoxy-6-O-methyl-erythromycin 2'-acetate 12-[chloroacetate] 4"-(phenylmethyl carbonate) (Scheme 2, formula IX-1) and 3-Imidazo[4,5-b]pyridin-3-yl-propane-1-thiol. MS (ISP): 1140.0 (MH⁺), 570.5 ([MH2]⁺⁺).

37G (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-3-[[3-[-[3H-imidazo [4,5-b]pyridin-3-yl]propyl]thio]-11-[[2,6-dideoxy-3-C-methyl-3-O-methyl-4-O-[(phenylmethoxy)carbonyl]-α-L-ribo-hexopyranosyl]oxy]-15-ethyldecahydro-8-methoxy-4,6,8,10,12,15a-hexamethyl-2H-furo[2,3-c]oxacyclotetradecin-2,5,13(3H,6H)-trione; (V-37) was obtained according to example 6E by cyclisation of IV-37. MS (ISP): 1139.6 (MH⁺), 570.6 ([MH₂]⁺⁺).

37H (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-3-[[3-[3H-imidazo[4,5-b]pyridin-3-yl]propyl]thio]-15-ethyldecahydro-11-hydroxy-8-methoxy-4,6,8,10,12,15a-hexamethyl-2H-furo[2,3-c]oxacyclotetradecin-2,5,13(3H,6H)-trione; (VI-37) was obtained from V-37 according to example 1D. MS (ISP): 847.4 (MH⁺), 424.5 ([MH₂]⁺⁺).

37I (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-3-[[3-[3H-imidazo [4,5-b]pyridin-3-yl]propyl]thio]-15-ethyloctahydro-8-methoxy-4,6,8,10,12,15a-hexamethyl-2H-furo[2,3-c]oxacyclotetradecin-2,5,11,13(3H,6H,12H)-tetrone; (VII-37) was obtained from VI-37 according to example 32I. MS (ISP): 845.3 (MH⁺), 423.2 ([MH₂]⁺⁺).

37K (3S,3aR,4R,6R,8R,9R,10R,12R,15R,15aS)-3-[[3-[3H-imidazo[4,5-b]pyridin-3-yl]propyl]thio]-15-ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-37) was obtained from VII-37 according to example 1F. MS (ISP): 803.4 (MH⁺), 402.8 ([MH₂]⁺⁺). ¹H-NMR (CDCl₃) diagnostic signals only: 0.87(t, 3H), 1.16 (d, 3H), 1.17 (d, 3H), 1.26 (d, 3H), 1.32 (d, 3H), 1.33 (d, 3H), 1.38 (s, 3H), 1.53 (s, 3H), 2.26 (s, 6H), 2.35–2.50 (m, 3H), 2.61 (s, 1H), 2.77 (m, 1H), 2.81 (s, 3H), 3.05–3.25 (m, 4H), 3.42–3.62 (m, 2H), 3.86 (q, 1H), 4.29 (d, 1H), 4.31 (s, 1H), 4.43 (d, 1H), 4.65–4.55 (m, 2H), 5.46 (dd, 1H), 7.22 (dd, 1H), 8.06 (d, 1H), 8.37 (s, 1H), 8.38 (dd, 1H).

EXAMPLE 38

Preparation of (3S,3aR,4R,6R,8R,9R,10R,12R,15R,15aS)-3-[[2-[9H-purine-9-yl]ethyl]thio]-15-ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-38, Compound of Formula I, Where R¹ is [2-[9H-purine-9-yl]ethyl]thio)

38B

9-H-purine-9-ethanol was prepared according to example 14b from purine and ethylene carbonate. MS (EI): 164.2 (M⁺, 27%), 133.1 (32%), 121.2 (100%).

38C 9-(2-Chloro-ethyl)-9H-purine was prepared according to example 14c from 9-H-purine-9-ethanol. MS (EI): 182.1 (M⁺, 58%), 147.2 (23%), 120.1 (100%).

38D

Ethanethioic acid, S-[[9H-purine-9-yl]ethyl]ester was obtained according to example 14D from 9-(2-Chloro-ethyl)-9H-purine and potassium thioacetate. MS (EI): 222.2 (M⁺, 4%), 179.1 (100%).

38E

[Purin-9-yl]-1-ethanethiol was obtained according to example 14E from Ethanethioic acid, S-[[9H-purine-9-yl]ethyl]ester. MS (ISP): 181.1 (MH⁺).

38F (10E)-10,11-didehydro-11-deoxy-6-O-methyl-erythromycin 2'-acetate 12-[[[2-[9H-purine-9-yl]ethyl]thio]acetate] 4"-(phenylmethyl carbonate) IV-38 was obtained according to example 14F from (10E)-10,11-Didehydro-11-deoxy-6-O-methyl-erythromycin 2'-acetate 12-[chloroacetate] 4"-(phenylmethyl carbonate) (Scheme 2, formula IX-1) and [Purin-9-yl]-1-ethanethiol. MS (ISP): 1126.6 (MH⁺), 563.8 ([MH2]⁺⁺)

38G (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-3-[[2-[9H-purine-9-yl]ethyl]thio]-11-[[2,6-dideoxy-3-C-methyl-3-O-methyl-4-O-[(phenylmethoxy)-carbonyl]-α-L-ribo-hexopyranosyl]oxy]-15-ethyldecahydro-8-methoxy-4,6,8,10,12,15a-hexamethyl-2H-furo[2,3-c]oxacyclotetradecin-2,5,13(3H,6H)-trione; (V-38) was obtained according to example 6E by cyclisation of IV-38. MS (ISP): 1126.5 (MH⁺), 564.1 ([MH₂]⁺⁺).

38H (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-3-[[2-[9H-purine-9-yl]ethyl]thio]-15-ethyldecahydro-11-hydroxy-8-methoxy-4,6,8,10,12,15a-hexamethyl-2H-furo[2,3-c]oxacyclotetradecin-2,5,13(3H,6H)-trione; (VI-38) was obtained from V-38 according to example 1D. MS (ISP): 834.4 (MH$^+$), 418.0 ([MH$_2$]$^{++}$).

38I (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-3-[[2-[9H-purine-9-yl]ethyl]thio]-15-ethyloctahydro-8-methoxy-4,6,8,10,12,15a-hexamethyl-2H-furo[2,3-c]oxacyclotetradecin-2,5,11,13(3H,6H,12H)-tetrone; (VII-38) was obtained from VI-38 according to example 32I. MS (ISP): 832.5 (MH$^+$), 417.1 ([MH$_2$]$^{++}$).

38K (3S,3aR,4R,6R,8R,9R,10R,12R,15R,15aS)-3-[[2-[9H-purine-9-yl]ethyl]thio]-15-ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-38) was obtained from VII-38 according to example 1F. MS (ISP): 790.3 (MH$^+$), 396.1 ([MH$_2$]$^{++}$). $^1$H-NMR (CDCl$_3$) diagnostic signals only: 0.86 (t, 3H), 1.16 (2xd, 6H), 1.26 (d, 3H), 1.32 (d, 3H), 1.34 (d, 3H), 1.38 (s, 3H), 1.53 (s, 3H), 1.74–192 (m, 4H), 2.26 (s, 6H), 2.54–2.42 (m, 1 H), 2.63 (s, 1H), 2.68 (s, 3H), 2.78–2.73 (m, 1H), 3.08–3.25 (m, 4H), 3.48 (broad s, 1H), 3.68–3.50 (m, 2H), 3.84 (q, 1H), 4.29 (d, 1H), 4.34 (d, 1H), 4.42 (s, 1H), 4.68–4.56 (m, 1H), 4.81 (dt, 1H), 5.38 (dd, 1H), 8.59 (s, 1H), 8.95 (s, 1H), 9.11 (s, 1H).

EXAMPLE 39

Preparation of (3S,3aR,4R,6R,8R,9R,10R,12R,15R,15aS)-3-[[3-[9H-purine-9-yl]propyl]thio]-15-ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone; (I-39, Compound of Formula I, Where R$^1$ is [3-[9H-purine-9-yl]propyl]thio)

39C 9-(3-Chloro-propyl)-9H-purine was obtained as a colourless oil from purine, 1-bromo-3-chloropropane and potassium t-butoxyde in DMF at room temperature. MS (EI): 196.1 (MH$^+$, 35%), 161.2 (58%), 134.2 (100%).

39D

Ethanethioic acid, S-[[9H-purine-9-yl]propyl]ester was obtained according to example 14D from 9-(3-Chloro-propyl)-9H-purine and potassium thioacetate. MS (ISP): 237.2 (MH$^+$).

39E 3-(Purin-9-yl)-propanethiol was obtained according to example 14E from Ethanethioic acid, S-[[9H-purine-9-yl]ethyl]ester. MS (ISP): 195.1 (MH$^+$).

39F (10E)-10,11-didehydro-11-deoxy-6-O-methyl-erythromycin 2'-acetate 12-[[[3-[9H-purine-9-yl]propyl]thio]acetate] 4"-(phenylmethyl carbonate) IV-39 was obtained according to example 14F from (10E)-10,11-Didehydro-11-deoxy-6-O-methyl-erythromycin 2'-acetate 12-[chloroacetate] 4"-(phenylmethyl carbonate) (Scheme 2, formula IX-1) and 3-(Purin-9-yl)-propanethiol. MS (ISP): 1140.6 (MH$^+$), 571.1 ([MH2]$^{++}$).

39G (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-3-[[3-[9H-purine-9-yl]propyl]thio]-11-[[2,6-dideoxy-3-C-methyl-3-O-methyl-4-O-[(phenylmethoxy)-carbonyl]-α-L-ribo-hexopyranosyl]oxy]-15-ethyldecahydro-8-methoxy-4,6,8,10,12,15a-hexamethyl-2H-furo[2,3-c]oxacyclotetradecin-2,5,13(3H,6H)-trione; (V-39) was obtained according to example 6E by cyclisation of IV-39. MS (ISP): 1140.5 (MH$^+$), 571.0 ([MH$_2$]$^{++}$).

39H (3S,3aR,4R,6R,8R,9R,10S,11S,12R,15R,15aS)-9-[[2-O-Acetyl-3,4,6-trideoxy-3-(dimethylamino)-β-D-xylo-hexopyranosyl]oxy]-3-[[3-[9H-purine-9-yl]propyl]thio]-15-ethyldecahydro-11-hydroxy-8-methoxy-4,6,8,10,12,15a-hexamethyl-2H-furo[2,3-c]oxacyclotetradecin-2,5,13(3H,6H)-trione; (VI-39) was obtained from V-39 according to example 1D. MS (ISP): 848.5 (MH$^+$).

39I (3S,3aR,4R,6R,8R,9R,10R,12R,15R,15aS)-9-[[2-O-Acetyl-3,4,6-trideoxy-3-(dimethylamino)-β-D-xylo-hexopyranosyl]oxy]-3-[[3-[9H-purine-9-yl]propyl]thio]-15-ethyloctahydro-8-methoxy-4,6,8,10,12,15a-hexamethyl-2H-furo[2,3-c]oxacydotetradecin-2,5,11,13(3H,6H,12H)-tetrone; (VII-39) was obtained from VI-39 according to example 1E. MS (ISP): 846.4 (MH$^+$).

39K (3S,3aR,4R,6R,8R,9R,10R,12R,15R,15aS)-3-[[3-[9H-purine-9-yl]propyl]thio]-15-ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c] oxacyclotetradecin-2,5,11,13(3H,6H,12H)-tetrone; (I-39) was obtained from VII-39 according to example 1F. MS (ISP): 804.5 (MH$^+$), 403.3 ([MH$_2$]$^{++}$). $^1$H-NMR (CDCl$_3$) diagnostic signals only: 0.87 (t, 3H), 1.16 (2xd, 6H), 1.26 (d, 3H), 1.32 (d, 3H), 1.34 (d, 3H), 1.38 (s, 3H), 1.53 (s, 3H), 1.54–192 (m, 4H), 2.29 (s, 6H), 2.62 (s, 1H), 2.78–2.70 (m, 1H), 2.81 (s, 3H), 3.30–3.05 (m, 5H), 3.62–3.50 (m, 2H), 3.84 (q, 1H), 4.30–4.24(m, 2H), 4.32 (d, 1H), 4.60–4.40 (m, 2H), 5.42 (dd, 1H), 8.45 (s, 1H), 8.98 (s, 1H), 9.14 (s, 1H).

Below some examples for the manufacture of medicaments are given

EXAMPLE A

Tablets of the following composition are manufactured in the usual manner:

|  | mg/tablet |
|---|---|
| Active substance | 500–1000 |
| Lactose | |
| Corn starch | |
| Microcrystalline cellulose | |
| Magnesium stearate | |
| Tablet weight | 1000–1500 |

EXAMPLE B

Capsules of the following composition are manufactured:

|  | mg/capsule |
|---|---|
| Active substance | 500–1000 |
| Lactose | |
| Corn starch | |
| Talc | |
| Capsule fill weight | 1000–1500 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
|---|---|
| Active substance | 500 |
| Suppository mass | |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

What is claimed is:

1. A compound of formula I:

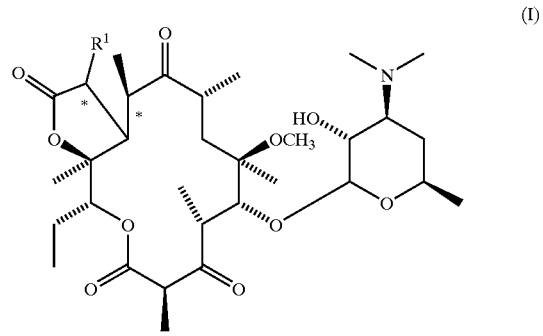

(I)

wherein
R$^1$ is hydrogen, cyano, —S(L)$_m$R$^2$, —S(O)(L)$_m$R$^2$, or —S(O)$_2$(L)$_m$R$^2$;
L represents —(CH$_2$)$_n$— or —(CH$_2$)$_n$Z(CH$_2$)$_{n'}$—;
m is 0 or 1;
n is 1, 2, 3, or 4;
n' is 0, 1, 2, 3, or 4;
Z is O, S or NH;
R$^2$ is hydrogen, alkyl, heterocyclyl or aryl; which heterocyclyl and the aryl groups may be further substituted;
* indicates a chiral center which is in the (R) or (S) form,
or a pharmaceutically acceptable acid addition salts or in vivo cleavable esters thereof.

2. The compound according to claim 1, wherein L is —(CH$_2$)$_n$ and n is 0, 1, 2 or 3.

3. The compound according to claim 1, wherein R$^1$ is one of the groups:

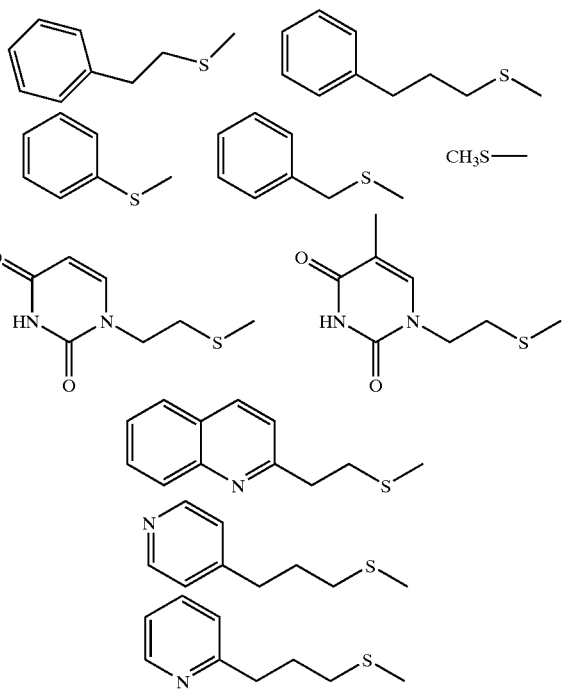

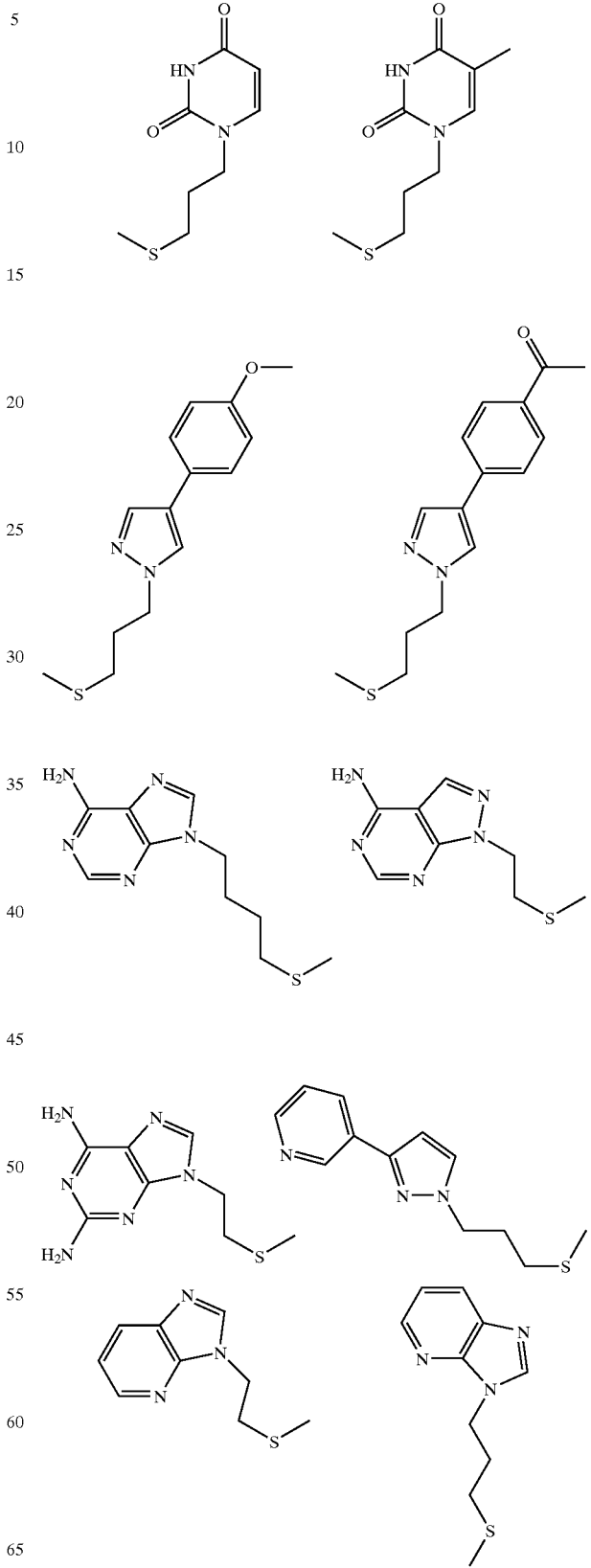
4. The compound according to claim 1, wherein $R^1$ is one of the groups:

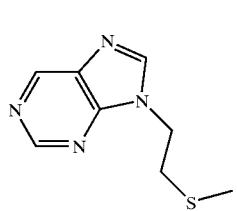 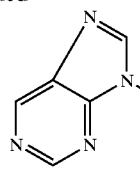

5. The compound according to claim 1 (3S,3aR,4R,6R,8R,9R,10R,12R,15R,15aS)-3-[[3-[6-Amino-9H-purine-9-yl]ethyl]thio]-15-ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c]oxacyclotetradecin-2,5,11,13 (3H,6H,12R)-tetrone.

6. The compound according to claim 1 (3S,3aR,4R,6R,8R,9R,10R,12R,15R,15aS)-15-Ethyloctahydro-8-methoxy-4,6,8,10,12,15a-hexamethyl-3-[[2-[3-(3-pyridinyl)-1H-pyrazol-1-yl]ethyl]thio]-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone.

7. The compound according to claim 1 (3S,3aR,4R,6R,8R,9R,10R,12R,15R,15aS)-3-[[2-[6-Amino-9H-purine-9-yl]propyl]thio]-15-ethyloctahydro-8-methoxy-4,6,8,10,12,15a-hexamethyl-9-[[3,4,6-trideoxy-3-(dimethylamino)-β-D-xylo-hexopyranosyl]oxy]-2H-furo[2,3-c]oxacyclotetradecin-2,5,11,13(3H,6H,12H)-tetrone.

8. A compound of the general formula:

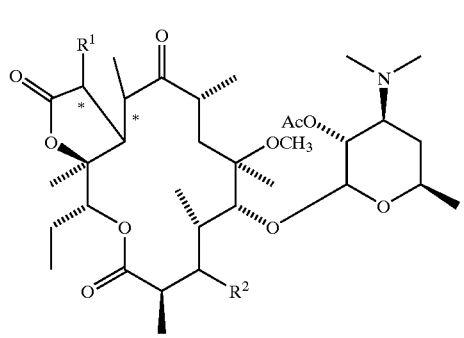

VIIA wherein
R¹ is hydrogen, cyano, —S(L)$_m$R², —S(O)(L)$_m$R², or —S(O)$_2$(L)$_m$R²
Ac is acetyl;
R² is oxo,

••••ııOH or the group

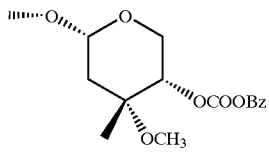

Bz is benzyl; and
* indicates a chiral center which is in the (R) or (S) form.

9. A compound of the general formula:

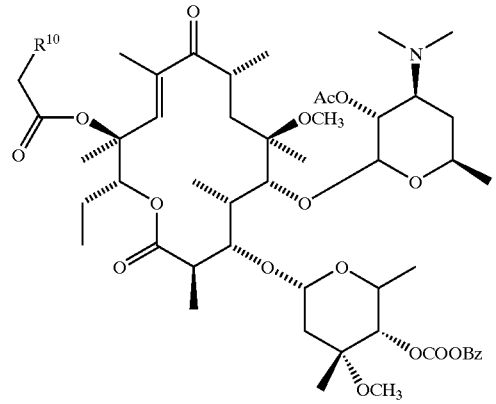

IVA wherein
R¹⁰ is hydrogen, cyano, —S(L)$_m$R², —S(O)(L)$_m$R², wherein R₂ is as defined in claim 1, or —S(O)$_2$(L)$_m$R²;
Ac is acetyl; and
Bz is benzyl.

10. Process for the manufacture of the compound of claim 1, which process comprises deacylating a compound of the formula:

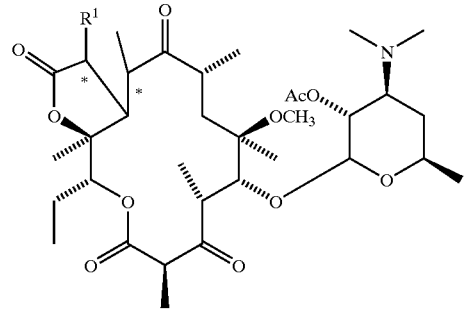

VII wherein Ac is acetyl;
R¹ is hydrogen, cyano, —S(L)$_m$R², —S(O)(L)$_m$R², or —S(O)$_2$(L)$_m$R² wherein R₂ is as defined in claim 1; and
* indicates a chiral center which is in the (R) or (S) form.

11. The compound according to claim 1, wherein R² is aryl or heterocyclyl.

12. The compound according to claim 1, wherein R² is phenyl dialkoxyphenyl, 6-amino-9H-purin-9-yl or pyridinyl-1H-pyrazol-1-yl.

13. The process according to claim 10, further comprising converting the compound of formula I obtained into a pharmaceutically acceptable acid addition salt or into an in vivo cleavable ester thereof.

14. A pharmaceutical composition comprising a compound according to claim 1 and a pharmaceutically acceptable excipient.

* * * * *